Figure 2:
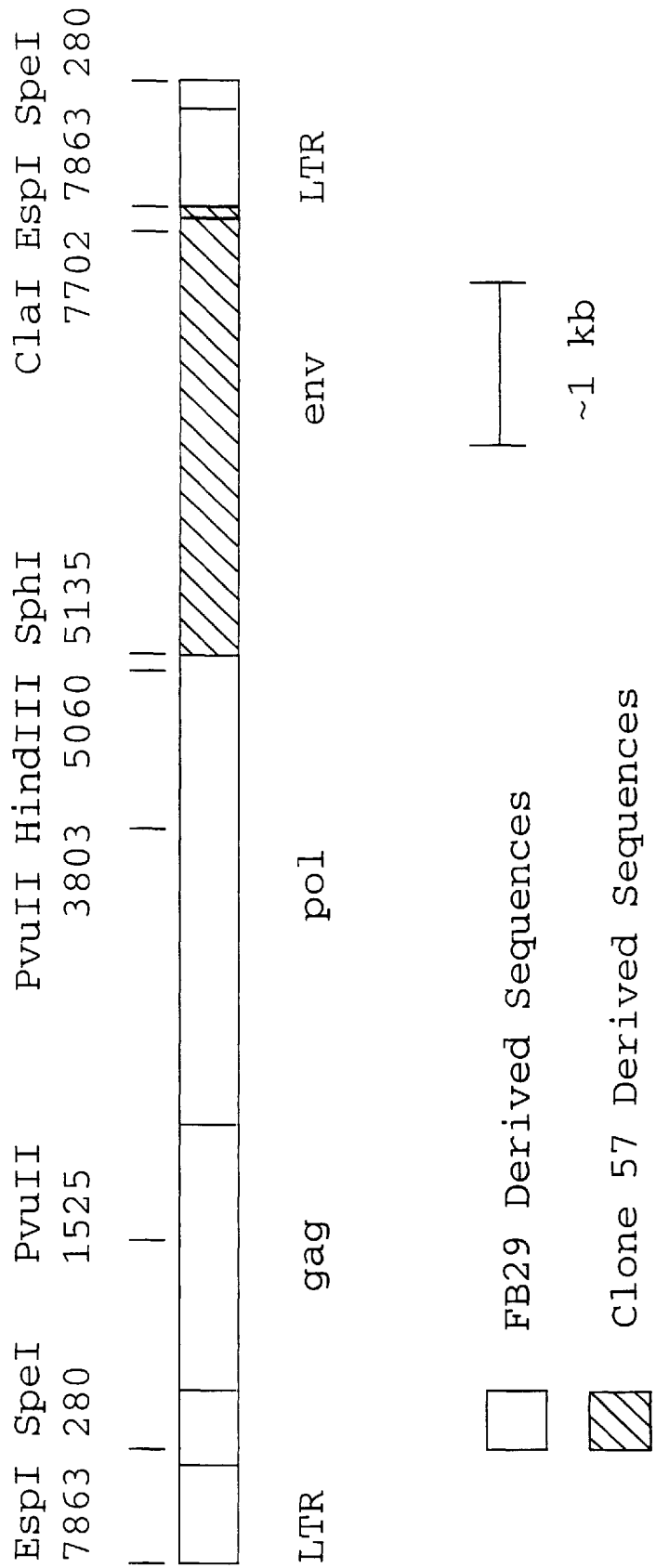

US005952474A

United States Patent [19]
Kayman et al.

[11] Patent Number: 5,952,474
[45] Date of Patent: Sep. 14, 1999

[54] FUSION GLYCOPROTEINS

[75] Inventors: Samuel Kayman, New York; Abraham Pinter, Brooklyn, both of N.Y.

[73] Assignee: The Public Health Research Institute of the City of New York, Inc., New York, N.Y.

[21] Appl. No.: 08/886,642

[22] Filed: Jul. 1, 1997

Related U.S. Application Data

[60] Division of application No. 08/110,300, Aug. 20, 1993, Pat. No. 5,643,756, which is a continuation-in-part of application No. 07/938,100, Aug. 28, 1992, abandoned.

[51] Int. Cl.$^6$ .................. C07K 14/16; C07K 14/435; C12P 21/02; C12N 15/85
[52] U.S. Cl. .................. 530/395; 435/69.7; 435/320.1; 530/350
[58] Field of Search .................. 530/350, 395; 435/69.7, 320.1, 325, 357; 536/23.4

[56] References Cited

U.S. PATENT DOCUMENTS

| | | | |
|---|---|---|---|
| 4,701,416 | 10/1987 | Nunberg | 435/320.1 |
| 5,266,478 | 11/1993 | Chang et al. | 435/328 |
| 5,643,756 | 7/1997 | Kayman et al. | 435/69.7 |

FOREIGN PATENT DOCUMENTS

| | | |
|---|---|---|
| 0 356 409 A2 | 2/1990 | European Pat. Off. . |
| WO 93/14188 | 7/1993 | WIPO . |
| WO 93/20221 | 10/1993 | WIPO . |
| WO 94/05780 | 3/1994 | WIPO . |
| WO 94/11524 | 5/1994 | WIPO . |
| WO 94/27643 | 12/1994 | WIPO . |

OTHER PUBLICATIONS

Alberts et al., "Molecular Biology of The Cell," Garland Publishing, Inc., New York, p. 172 (1983).
Battini, J. et al., "Receptor Choice Determinants in the Envelope Glycoproteins of Amphotropic, Xenotropic, And Polytropic Murine Leukemia Viruses," Journal of Virology, vol. 66, No. 3, pp. 1468–1475 (1992).
Benjouad, A., et al., "Influence of Carbohydrate Moieties On The Immunogenicity of Human Immunodeficiency Virus Type I Recombinant gp160," Journal of Virology, vol. 66, No. 4, pp. 2473–2483 (1992).
Buchbinder, A., et al., "Synergy Between Human Monoclonal Antibodies To HIV Extends Their Effective Biologic Activity Against Homologous And Divergent Strains," AIDS Research And Human Retroviruses, vol. 8, No. 4, pp. 425–427 (1992).
Fenouillet, E., et al., "Role of N–Linked Glycans In The Interaction Between The Envelope Glycoprotein of Human Immunodeficiency Virus And Its CD4 Cellular Receptor." J. Exp. Med. vol. 169, pp. 807–822 (1989).
Fenouillet, E., et al., "Role of N–Linked Glycans of Envelope Glycoproteins In Infectivity of Human Immunodeficiency Virus Type 1," Journal of Virology, vol. 64, No. 6, pp. 2841–2848 (1990).

Fung, M.S.C., et al., "Identification And Characterization of A Neutralization Site Within The Second Variable Region of Human Immunodeficiency Virus Tuype 1 gp120," Journal of Virology, vol. 66, No. 2, pp. 848–856 (1992).
Haigwood, N.L., et al., "Native But Not Denatured Recombinant Human Immunodeficiency Virus Type 1 gp120 Generates Broad–Spectrum Neutralizing Antobodies In Baboons," Journal of Virology, vol. 66, No. 1, pp. 172–182 (1992).
Heard, J.M., et al., "An Amino–Terminal Fragment of The Friend Murine Leukemia Virus Envelope Glycoprotein Binds The Ecotropic Receptor," Journal of Virology, vol. 65, No. 8, pp. 4026–4032 (1992).
Ho, D.D., et al., "Another Discontinuous Epitode On Glycoprotein gp120 That Is Important In Human Immunodeficiency Virus Type 1 Neutralization Is Identified By A Monoclonal Antibody," Proc. Natl. Acad. Sci., U.S.A., vol. 88, pp. 8949–8952 (1991).
Ho, D.D., et al., "Human Immunodeficiency Virus Neutralizing Antibodies Recognize Several Conserved Domains On The Envelope Glycoproteins," Journal of Virology, vol. 61, pp. 2024–2028 (1987).
Kayman, S.C., et al., "Mutational Analysis of N–Linked Glycosylation Sites of Friend Murine Leukemia Virus Envelope Protein," Journal of Virology, vol. 65, No. 10, pp. 5323–5232 (1991).
Kennedy, M.S., et al., "Analysis of Synergism/Antagonism Between HIV–1 Antibidy–Positive Human Sera And Soluble CD4 In Blocking HIV–1 Binding And Infectivity," AIDS Research And Human Retroviruses, vol. 7, No. 12, pp. 975–981 (1991).
Leonard, C.K., et al., "Assignment of Intrachain Disulfide Bonds And Characterization of Potential Glycosylation Sites of The Type 1 Recombinant Human Immunodeficiency Virus Envelope Glycoprotein (gp120) Expressed In Chinese Hamster Ovary Cells," Journal of Biological Chemistry, vol. 265, No. 18, pp. 10373–10382 (1990).
Lynch, C.M., et al., "Production of High–Titer Helper Virus–Free Retroviral Vectors By Cocultivation of Packaging Cells With Different Host Ranges," Journal of Virology, vol. 65, No. 7, pp. 3887–3890 (1991).
Mace, et al., "Retroviral Envelope Protein Fusions To Secreted And Menbrane markers," Virology, vol. 188, pp. 869–874 (1992).
Matthews, T.J., et al., "Interaction Between The Human T–Cell Lymphotropic Virus III$^B$ Envelope Glycoprotein gp120 And The Surface Antigen CD4: Role of Carbohydrate In Binding And Cell Fusion," Proc. Natl. Acad. Sci., U.S.A., vol. 84, pp. 5424–5428 (1987).

(List continued on next page.)

*Primary Examiner*—Nancy Degen
*Attorney, Agent, or Firm*—Fish & Richardson P.C.

[57] ABSTRACT

Novel expression vectors are provided for expressing a fusion glycoprotein. The fusion glycoprotein contains the N-terminal globular domain of a retroviral env surface protein linked to a selected glycopeptide. Truncation glycoproteins as well as insertion glycoproteins are expressed using the vectors.

**19 Claims, 19 Dr

OTHER PUBLICATIONS

Ott, D., et al., "Basis For Receptor Specificity of Nonecotropic Murine Leukemia Virus Surface Gluycoprotein gp70$^{su}$," Journal of Virology, vol. 66, No. 8, pp. 4632–4638 (1992).

Pollard, S.R., et al., "Truncated Varaint of gp120 Bind CD4 With High Affinity And Suggest A Minimum CD4 Binding Region," The EMBO Journal, vol. 11, No. 2, pp. 585–591 (1992).

Posner, M., et al., "Development of An IgG–1 Human Monoclonal Antibody That Neutralizes HIV–1 Infectivity And Binding And Reacts With A Cell Surface Antigen Expressed By HIV–1 Infected Cells," VI Int'l. Conf. on AIDS, San Francisco, CA, Abstract Th.A.77 (1990).

Russell, S.J., et al., "Retroviral Vectors Displaying Functional Antibody Fragments," Nucleic Acids Research, vol. 21, No. 5, pp. 1081–1085 (1993).

Stephens, D.M., et al., "The Second Variable region of HIV–1 External Envelope Glycoprotein Contains A Neutralizing Epitope," VII Int'l Conf. on AIDS, Florence, Italy, Abstract TH.A.66 (1991).

Tilley, S.A., et al., "Human Monoclonal Antibodies Against The Putative CD4 Binding Site And The V3 Loop of HIV gp120 Act In Concert To Neutralize Virus," VIII Int'l Conf. On Aids, Florence, Italy, Abstract MA.70 (1991).

Tilley, S.A., et al., "Very Broadly Neutralizing Human Monoclonal Antibody (HuMAb) Against The CD4–Binding Site Of HIV–1 gp120," VIII Int'l. Conf. On AIDS/III STD World Congress, Amsterdam, The Netherlands, Abstract.

Tilley, S.A., et al., "Synergistic Neutralization of HIV–1 By Human Monoclonal Antibodies Against The V3 Loop And The CD4–Binding Site of gp120," AIDS Research And Human Retroviruses, vol. 8, No. 4, pp. 461–467 (1992).

Tilley, S.A., et al., "Potent Neutralization of HIV–1 By Human And Chimpanzee Monoclonal Antibodies Directed Against Three Distinct Epitope Clusters of gp120," Sixieme Coloque Des Cent Gardes, pp. 211–216 (1991).

Young, J.A.T., et al., "Efficient Incorporation of Human CD4 Protein Into Avian Leukosis Virus Particles," Science, vol. 250, pp. 1421–1423 (1990).

Wills, J.W., "Retro–Secretion of Recombinant Proteins," Nature, vol. 340, pp. 323–324 (1989).

Wu et al.; J. Virol. Apr. 1995; v. 69; p.. 2271–2278; Characterization of Neutralization Epitopes in the V2 Region of Human Immunodeficiency Virus Type 1, grp 120: Role of Glycosylation in the Correct Folding of the V1/V2 Domain.

Albert et al.; Molecular Biology of the Cell (Garland Publishing, Inc., New York, 1983) p. 172.

FIG. 1A

```
              |       10         |       20         |       30         |       40
     1    GCGCCAGTCC   TCCGATAGAC   TGAGTCGCCC   GGGTACCCGT
    41    GTATCCAATA   AATCCTCTTG   CTGTTGCATC   CGACTCGTGG
    81    TCTCGCTGTT   CCTTGGGAGG   GTCTCCTCAG   AGTGATTGAC
   121    TACCCGTCTC   GGGGGTCTTT   CATTTGGGGG   CTCGTCCGGG
   161    ATCTGGAGAC   CCCTGCCCAG   GGACCACCGA   CCCACCACCG
   201    GGAGGTAAGC   TGGCCAGCAA   TTGTTCTGTG   TCTGTCCATT
   241    GTCCTGTGTC   TTTGATTGAT   TTTATGCGCC   TGTGTCTGTA
   281    CTAGTTGGCC   GACTAGATTG   GTATCTGGCG   GATCCGTGGT
   321    GGAACTGACG   AGTTCGAGAC   ACCCGGCCGC   AACCCTGGGA
   361    GACGTCCAG    GGACTTCGGG   GGCCATTTTT   GTGGCCCGGC
   401    CAGAGTCCAA   CCATCCCGAT   CGTTTTGGAC   TCTTTGGTGC
   441    ACCCCCTTA    GAGGAGGGGT   ATGTGGTTCT   GGTAGGAGAC
   481    AGAGGGCTAA   AACGGTTTCC   GCCCCCGTCT   GAGTTTTTGC
   521    TTTCGGTTTG   GAACCGAAGC   CGCGCCGCGC   GTCTTGTCTG
   561    CTGCAGCATC   GTTCTGTGTT   GTCTCTGTTT   GACTGTTTTT
   601    CTGTATTTGT   CTGAAAACAT   GGGCCAGGCT   GTTACCACCC
   641    CCTTAAGTTT   GACTTTAGAC   CACTGGAAGG   ATGTCGAACG
   681    GACAGCCCAC   AACCTGTCGG   TAGAGGTTAG   AAAAAGGCGC
   721    TGGGTTACAT   TCTGCTCTGC   AGAATGGCCA   ACCTTCAACG
   761    TCGGATGGCC   ACGAGACGGC   ACTTTTAACC   CAGACATTAT
   801    TACACAGGTT   AAGATCAAGG   TCTTCTCACC   TGGCCCACAT
   841    GGACATCCGG   ATCAGGTCCC   CTACATCGTG   ACCTGGGAAG
   881    CTATAGCAGT   AGACCCCCCT   CCCTGGGTCA   GACCCTTCGT
   921    GCACCCTAAA   CCTCCCTCT    CTCTTCCCCC   TTCAGCCCCC
   961    TCTCTCCCAC   CTGAACCCCC   ACTCTCGACC   CCGCCCCAGT
  1001    CCTCCCTCTA   TCCGGCTCTC   ACTTCTCCTT   TAAACACCAA
  1041    ACCTAGGCCT   CAAGTCCTTC   CTGATAGCGG   AGGACCACTC
  1081    ATTGATCTAC   TCACGGAGGA   CCCTCCGCCT   TACCGGGACC
  1121    CAGGGCCACC   CTCTCCTGAC   GGGAACGGCG   ATAGCGGAGA
  1161    AGTGGCCCCT   ACAGAAGGAG   CCCCTGACCC   TTCCCCAATG
  1201    GTATCCCGCC   TGCGGGGAAG   AAAAGAACCC   CCCGTGGCGG
  1241    ATTCTACTAC   CTCTCAGGCG   TTCCCCCTTC   GCCTGGGAGG
  1281    GAATGGACAG   TATCAATACT   GGCCATTTTC   CTCCTCTGAC
  1321    CTCTATAACT   GGAAAAATAA   CAACCCCTCT   TTCTCCGAGG
  1361    ACCCAGCTAA   ATTGACAGCT   TTGATCGAGT   CCGTTCTCCT
  1401    TACTCATCAG   CCCACTTGGG   ATGACTGCCA   ACAGCTATTA
  1441    GGGACCCTGC   TGACGGGAGA   AGAAAAACAG   CGAGTGCTCC
  1481    TAGAGGCCCG   AAAGGCGGTT   CGAGGGGAGG   ACGGACGCCC
  1521    AACTCAGCTG   CCCAATGACA   TTAATGATGC   TTTTCCCTTG
  1561    GAACGTCCCG   ACTGGACTA    CAACACCCAA   CGAGGTAGGA
  1601    ACCACCTAGT   CCACTATCGC   CAGTTGCTCC   TAGCGGGTCT
```

FIG. 1B

```
           |  10       |  20       |  30       |  40
1641   CCAAAACGCG GGCAGAAGCC CCACCAATTT GGCCAAGGTA
1681   AAAGGGATAA CCCAGGGACC TAATGAGTCT CCCTCAGCCT
1721   TTTTAGAGAG ACTCAAGGAG GCCTATCGCA GATACACTCC
1761   TTATGACCCT GAGGACCCAG GGCAAGAAAC CAATGTGGCC
1801   ATGTCATTCA TCTGGCAGTC CGCCCCGGAT ATCGGGCGAA
1841   AGTTAGAGCG GTTAGAAGAT TGAAGAGTA AGACCTTAGG
1881   AGACTTAGTG AGGGAAGCTG AAAAGATCTT TAATAAACGA
1921   GAAACCCCGG AAGAAAGAGA GGAACGTATT AGGAGAGAAA
1961   CAGAGGAAAA GGAAGAACGC CGTAGGGCAG AGGATGTGCA
2001   GAGAGAGAAG GAGAGGGACC GCAGAAGACA TAGAGAAATG
2041   AGTAAGTTGC TGGCTACTGT CGTTAGCGGG CAGAGACAGG
2081   ATAGACAGGG AGGAGAGCGA AGGAGGCCCC AACTCGACCA
2121   CGACCAGTGT GCCTACTGCA AAGAAAGGG ACATTGGCT
2161   AGAGATTGCC CCAAGAAGCC AAGAGGACCC CGGGGACCAC
2201   GACCCCAGGC CTCCCTCCTG ACCTTAGACG ATTAGGGAGG
2241   TCAGGGTCAG GAGCCCCCCC CTGAACCCAG GATAACCCTC
2281   AGAGTCGGGG GGCAACCCGT CACCTTCCTA GTGGATACTG
2321   GGGCCCAACA CTCCGTGCTG ACCCAAAATC CTGGACCCCT
2361   AAGTGACAAG TCTGCCTGGG TCCAAGGGGC TACTGGAGGG
2401   AAGCGGTATC GCTGGACCAC GGATCGCCGA GTGCACCTAG
2441   CCACCGGTAA GGTCACCCAT TCTTTCCTCC ATGTACCAGA
2481   TTGCCCCTAT CCTCTGCTAG GAAGAGATTT GCTGACTAAA
2521   CTAAAAGCCC AAATTCACTT TGAGGGATCA GGAGCTCAGG
2561   TTGTGGGACC AATGGGACAG CCCCTGCAAG TGCTGACCCT
2601   AAACATAGAA GATGAGTATC GGCTACATGA GACCTCAAAA
2641   GGGCCAGATG TGCCTCTAGG GTCCACATGG CTCTCTGATT
2681   TTCCCCAGGC CTGGGCAGAA ACCGGGGGCA TGGGGCTGGC
2721   CGTTCGCCAA GCTCCTCTGA TCATACCTCT GAAGGCAACC
2761   TCTACCCCCG TGTCCATAAA ACAATACCCC ATGTCACAAG
2801   AAGCCAGACT GGGGATCAAG CCCCACATAC AGAGACTGCT
2841   GGATCAGGGA ATTCTGGTAC CCTGCCAGTC CCCCTGGAAC
2881   ACGCCCTGC TACCCGTTAA GAAACCGGGG ACTAATGATT
2921   ATAGGCCTGT CCAGGATCTG AGAGAAGTCA ACAAGCGGGT
2961   GGAAGACATC CACCCCACCG TGCCCAACCC TTACAACCTC
3001   TTGAGCGGGC TCCCACCGTC CCACCAGTGG TACACTGTGC
3041   TTGACTTAAA AGATGCTTTT TTCTGCCTGA GACTCCACCC
3081   CACCAGTCAG TCTCTCTTCG CCTTTGAGTG GAGAGATCCA
3121   GAGATGGAA TCTCAGGACA ATTAACCTGG ACCAGACTCC
3161   CGCAGGGTTT CAAAAACAGT CCCACCCTGT TTGATGAAGC
3201   CCTGCACAGG GACCTCGCAG ACTTCCGGAT CCAGCACCCA
3241   GACCTGATTC TGCTCCAGTA TGTAGATGAC TTACTGCTGG
3281   CCGCCACTTC TGAGCTTGAC TGTCAACAAG GTACGCGGGC
3321   CCTGTTACAA ACCCTAGGGG ACCTCGGATA TCGGGCCTCG
3361   GCCAAGAAAG CCCAAATTTG CCAGAAACAG GTCAAGTATC
```

FIG. 1C

```
              |    10       |    20       |    30       |    40
3401    TGGGGTATCT   TCTAAAAGAG   GGTCAGAGAT   GGCTGACTGA
3441    GGCCAGAAAA   GAGACTGTGA   TGGGGCAGCC   TACTCCGAAG
3481    ACCCCTCGAC   AACTAAGGGA   GTTCCTAGGG   ACGGCAGGCT
3521    TCTGTCGCCT   CTGGATCCCT   GGGTTTGCAG   AAATGGCAGC
3561    CCCCTTGTAC   CCTCTCACCA   AAACGGGGAC   TCTGTTTGAG
3601    TGGGGCCCAG   ACCAGCAAAA   GGCCTACCAA   GAGATCAAGC
3641    AGGCTCTCTT   AACTGCCCCT   GCCCTGGGAT   TGCCAGACTT
3681    GACTAAGCCC   TTCGAACTTT   TTGTTGACGA   GAAGCAGGGC
3721    TACGCCAAAG   GTGTCCTAAC   GCAAAACTG    GGGCCTTGGC
3761    GTCGGCCGGT   GGCCTACCTG   TCCAAAAAGC   TAGACCCAGT
3801    GGCAGCTGGG   TGGCCCCCTT   GCCTACGGAT   GGTAGCAGCC
3841    ATCGCCGTTC   TGACCAAAGA   CGCTGGCAAG   CTCACCATGG
3881    GACAGCCACT   AGTCATTCTG   GCCCCCATG    CAGTAGAGGC
3921    ACTAGTTAAG   CAACCCCCTG   ATCGCTGGCT   CTCCAACGCC
3961    CGAATGACCC   ACTACCAGGC   TCTGCTTCTG   GACACGGACC
4001    GAGTCCAGTT   CGGACCAATA   GTGGCCCTAA   ACCCAGCTAC
4041    GCTGCTCCCT   CTACCTGAGG   AGGGGCTGCA   ACATGACTGC
4081    CTTGACATCT   TGGCTGAAGC   CCACGGAACT   AGACCAGATC
4121    TTACGGACCA   GCCTCTCCCA   GACGCTGACC   ACACCTGGTA
4161    CACAGATGGG   AGCAGCTTCC   TGCAAGAGGG   GCAGCGCAAG
4201    GCCGGAGCAG   CAGTAACCAC   CGAGACCGAG   GTAGTCTGGG
4241    CCAAAGCACT   GCCAGCCGGG   ACATCGGCCC   AAAGAGCTGA
4281    GTTGATAGCG   CTCACCCAAG   CCTTAAAAAT   GGCAGAAGGT
4321    AAGAAGCTGA   ATGTTTACAC   CGATAGCCGT   TATGCTTTTG
4361    CCACTGCCCA   TATTCACGGA   GAAATATATA   GAAGGCGCGG
4401    GTTGCTCACA   TCAGAAGGAA   AAGAAATCAA   AAATAAGGAC
4441    GAGATCTTGG   CCCTACTGAA   GGCTCTCTTC   CTGCCCAAAA
4481    GACTTAGCAT   AATTCATTGC   CCGGGACATC   AGAAGGGAAA
4521    CCGCGCGGAG   GCAAGGGGCA   ACAGGATGGC   CGACCAAGCG
4561    GCCCGAGAAG   TAGCCACTAG   AGAAACTCCA   GAGACTTCCA
4601    CACTTCTGAT   AGAAAATTCA   GCCCCTATA    CTCATGAACA
4641    TTTTCACTAT   ACGGTGACTG   ACATAAAAGA   TCTGACTAAA
4681    CTAGGGGCCA   CTTATGACGA   TGCAAAGAAG   TGTTGGGTTT
4721    ATCAGGGAAA   GCCTGTAATG   CCTGATCAAT   TCACCTTTGA
4761    ACTATTAGAT   TTTCTTCATC   AATTGACCCA   CCTCAGTTTC
4800    TCAAAAACAA   AGGCTCTTCT   AGAAGGAAC    TACTGTCCTT
4841    ATTACATGCT   GAACCGGGAT   CGAACGCTCA   AAGACATCAC
4881    TGAGACTTGC   CAAGCCTGTG   CACAGGTCAA   TGCCAGCAAG
4921    TCTGCCGTCA   AACAAGGGAC   TAGAGTTCGA   GGGCACCGAC
4961    CCGGCACCCA   CTGGGAAATT   GATTTCACTG   AGGTAAAACC
5001    TGGCCTGTAT   GGGTATAAAT   ATCTTTTAGT   TTTCATAGAC
5041    ACTTTCTCTG   GATGGGTAGA   AGCTTTCCCA   ACCAAGAAAG
5081    AAACTGCCAA   AGTTGTAACC   AAGAAGCTAC   TAGAAGAAAT
5121    CTTCCCCAGA   TTCGGCATGC   CACAGGTATT   GGGAACCGAC
```

FIG. 1D

```
             |   10       |   20       |   30       |   40
 5161    AATGGGCCTG   CCTTCGTCTC   CAAGGTAAGT   CAGACAGTAG
 5201    CCGATTTACT   GGGGGTTGAT   TGGAAACTAC   ATTGTGCTTA
 5241    CAGACCCCAG   AGTTCAGGTC   AGGTAGAAAG   AATGAATAGG
 5281    ACAATCAAGG   AGACTTTAAC   TAAATTGACG   CTTGCAACTG
 5321    GCTCTAGGGA   CTGGGTGCTC   CTGCTTCCCC   TAGCCCTGTA
 5361    TCGAGCCCGC   AACACGCCGG   GCCCCATGG    TCTCACCCCA
 5401    TATGAAATCT   TATATGGGC    ACCCCCGCCC   CTTGTAAACT
 5441    TCCCTGATCC   TGACATGGCA   AAGGTTACTC   ATAACCCCTC
 5481    TCTCCAAGCC   CATTTACAGG   CACTCTACCT   GGTCCAGCAC
 5521    GAAGTCTGGA   GACCGTTGGC   GGCAGCTTAC   CAAGAACAAC
 5561    TGGACCGGCC   GGTAGTGCCT   CACCCTTTCC   GAGTCGGTGA
 5601    CACAGTGTGG   GTCCGCAGAC   ACCAAACTAA   AAATCTAGAA
 5641    CCCCGCTGGA   AAGGACCTTA   TACCGTCCTA   CTGACTACCC
 5681    CCACCGCTCT   CAAAGTGGAC   GGCATTGCAG   CGTGGATCCA
 5721    CGCTGCCCAC   GTAAAGGCTG   CCGACACCAG   GATTGAGCCA
 5761    CCATCGGAAT   CGACATGGCG   TGTTCAACGC   TCTCAAAATC
 5801    CCCTAAAGAT   AAGATTGACC   CGCGGGACCT   CCTAATCCCC
 5841    TTAATTCTCT   TCCTGTCTCT   CAAAGGGCC    AGATCCGCAG
 5881    CACCCGGCTC   CAGCCCTCAC   CAGGTCTACA   ACATTACCTG
 5921    GGAAGTGACC   AATGGGGATC   GGGAGACAGT   ATGGGCAATA
 5961    TCAGGCAACC   ACCCTCTGTG   GACTTGGTGG   CCAGTCCTCA
 6001    CCCCAGATTT   GTGTATGTTA   GCTCTCAGTG   GGCCGCCCCA
 6041    CTGGGGGCTA   GAGTATCAGG   CCCCCTATTC   CTCGCCCCCG
 6081    GGGCCCCCTT   GTTGCTCAGG   GAGCAGCGGG   AACGTTGCAG
 6121    GCTGTGCCAG   AGACTGCAAC   GAGCCCTTGA   CCTCCCTCAC
 6161    CCCTCGGTGC   AACACTGCCT   GGAACAGACT   TAAGCTGGAC
 6201    CAGGTAACTC   ATAAATCAAG   TGAGGGATTT   TATGTCTGCC
 6241    CCGGGTCACA   TCGCCCCCGG   GAAGCCAAGT   CCTGTGGGGG
 6281    TCCAGACTCC   TTCTACTGTG   CCTCTTGGGG   CTGCGAGACA
 6321    ACCGGTAGAG   TATACTGGAA   GCCCTCCTCT   TCTTGGGACT
 6361    ACATCACAGT   AGACAACAAT   CTCACCTCTA   ACCAGGCTGT
 6401    TCAGGTATGC   AAAGACAATA   AGTGGTGCAA   TCCCTTGGCT
 6441    ATCCGGTTTA   CAAACGCCGG   GAAACAGGTC   ACCTCATGGA
 6481    CAACTGGACA   CTATTGGGGT   CTACGTCTTT   ATGTCTCTGG
 6521    ACAGGACCCA   GGGCTTACTT   TCGGGATCCG   ACTCAGTTAT
 6561    CAAAATCTAG   GACCTCGGAT   CCCAATAGGA   CCAAACCCCG
 6601    TCCTGGCAGA   CCAACTTTCG   TTCCCGCTAC   CTAATCCCCT
 6641    ACCCAAACCT   GCCAAGTCTC   CCCCGCCTC    TAGTTCGACT
 6681    CCCACATTGA   TTTCCCCGTC   CCCCACTCCC   ACTCAGCCCC
 6721    CGCCAGCAGG   AACGGGAGAC   AGATTACTAA   ATCTAGTACA
 6761    GGGAGCTTAC   CAGGCACTCA   ACCTTACCAA   CCCTGATAAA
 6801    ACTCAAGAGT   GCTGGTTATG   CCTAGTGTCT   GGACCCCCCT
 6841    ATTACGAGGG   GGTTGCCGTC   CTAGGTACTT   ATTCCAACCA
 6881    TACCTCTGCC   CCAGCTAACT   GCTCCGTGGC   CTCCCAACAC
```

FIG. 1E

```
             |   10       |   20       |   30       |   40
6921    AAGCTGACCC   TGTCCGAAGT   GACTGGACGG   GGACTCTGCA
6961    TAGGAACAGT   CCCAAAAACT   CACCAGGCCC   TGTGCAACAC
7001    TACCCTTAAG   GCAGGCAAAG   GGTCTTACTA   TCTAGTTGCC
7041    CCCACAGGAA   CTATGTGGGC   ATGTAACACT   GGACTCACTC
7081    CATGCCTATC   TGCCACCGTG   CTTAATCGCA   CCACTGACTA
7121    TTGCGTTCTC   GTGGAATTAT   GGCCCAGGGT   CACCTACCAT
7161    CCTCCCAGTT   ACGTCTATAG   CCAGTTTGAA   AAATCCCATA
7201    GACATAAAAG   AGAACCAGTG   TCCTTAACCT   TGGCCTTATT
7241    ATTAGGTGGG   CTAACTATGG   GTGGCATCGC   CGCGGGAGTA
7281    GGGACAGGAA   CTACCGCCCT   GGTCGCCACC   CAGCAGTTTC
7321    AGCAGCTCCA   TGCTGCCGTA   CAAGATGATC   TCAAAGAAGT
7361    CGAAAAGTCA   ATTACTAACC   TAGAAAAGTC   TCTTACTTCG
7401    TTGTCTGAGG   TTGTACTGCA   GAATCGACGA   GGCCTAGACC
7441    TGTTGTTCCT   AAAAGAGGGA   GGACTGTGTG   CTGCCCTAAA
7481    AGAAGAATGT   TGTTTCTATG   CTGACCATAC   AGGCCTAGTA
7521    AGAGATAGTA   TGGCCAAATT   AAGAGAGAGA   CTCTCTCAGA
7561    GACAAAAACT   ATTTGAGTCG   AGCCAAGGAT   GGTTCGAAGG
7601    ATGGTTTAAC   AGATCCCCCT   GGTTTACCAC   GTTGATATCC
7641    ACCATCATGG   GGCCTCTCAT   TATACTCCTA   CTAATTCTGC
7681    TTTTTGGACC   CTGCATTCTT   AATCGATTAG   TTCAATTTGT
7721    TAAAGACAGG   ATCTCAGTAG   TCCAGGCTTT   AGTCCTGACT
7761    CAACAATACC   ACCAGCTAAA   ACCACTAGAA   TACGAGCCAC
7801    AATAAATAAA   AGATTTTATT   TAGTTTCCAG   AAAAAGGGGG
7841    GAATGAAAGA   CCCCACCAAA   TTGCTTAGCC   TGATAGCCGC
7881    AGTAACGCCA   TTTTGCAAGG   CATGGAAAAA   TACCAAACCA
7921    AGAATAGAGA   AGTTCAGATC   AAGGGCGGGT   ACACGAAAAC
7961    AGCTAACGTT   GGGCCAAACA   GGATATCTGC   GGTGAGCAGT
8001    TTCGGCCCCG   GCCCGGGGCC   AAGAACAGAT   GGTCACCGCG
8041    GTTCGGCCCC   GGCCCGGGGC   CAAGAACAGA   TGGTCCCCAG
8081    ATATGGCCCA   ACCCTCAGCA   GTTTCTTAAG   ACCCATCAGA
8121    TGTTTCCAGG   CTCCCCCAAG   GACCTGAAAT   GACCCTGTGC
8161    CTTATTTGAA   TTAACCAATC   AGCCTGCTTC   TCGCTTCTGT
8201    TCGCGCGCTT   CTGCTTCCCG   AGCTCTATAA   AAGAGCTCAC
8241    AACCCCTCAC   TCGGCGCGCC   AGTCCTCCGA   TAGACTGAGT
8281    CGCCCGGGTA   CCCGTGTATC   CAATAAATCC   TCTTGCTGTT
8321    GCA   (SEQ ID NO: 8)
```

FIG. 3A

```
            |    10       |    20       |    30       |    40
   1   gaactcgagc   agggCTAGTA   CAGACACAGG   CGCATAAAAT
  41   CAATCAAAGA   CACAGGACAA   TGGACAGACA   CAGAACAATT
  81   GCTGGCCAGC   TTACCTCCCG   GTGGTGGGTC   GGTGGTCCCT
 121   GGGCAGGGGT   CTCCAGATCC   CGGACGAGCC   CCCAAATGAA
 161   AGACCCCCGA   GACGGGTAGT   CAATCACTCT   GAGGAGACCC
 201   TCCCAAGGAA   CAGCGAGACC   ACGAGTCGGA   TGCAACAGCA
 241   AGAGGATTTA   TTGGATACAC   GGGTACCCGG   GCGACTCAGT
 281   CTATCGGAGG   ACTGGCGCGC   CGAGTGAGGG   GTTGTGAGCT
 321   CTTTTATAGA   GCTCGGGAAG   CAGAAGCGCG   CGAACAGAAG
 361   CGAGAAGCAG   GCTGATTGGT   TAATTCAAAT   AAGGCACAGG
 401   GTCATTTCAG   GTCCTTGGGG   GAGCCTGGAA   ACATCTGATG
 441   GGTCTTAAGA   AACTGCTGAG   GGTTGGGCCA   TATCTGGGA
 481   CCATCTGTTC   TTGGCCCCGG   GCCGGGGCCG   AACCGCGGTG
 521   ACCATCTGTT   CTTGGCCCCG   GGCCGGGGCC   GAAACTGCTC
 561   ACCGCAGATA   TCCTGTTTGG   CCCAACGTTA   GCTGTTTTCG
 601   TGTACCCGCC   CTTGATCTGA   ACTTCTCTAT   TCTTGGTTTG
 641   GTATTTTTCC   ATGCCTTGCA   AAATGGCGTT   ACTGCGGCTA
 681   TCAGGCTAAG   CAACTTGGTG   GGGTCTTTCA   TTCCCCCCTT
 721   TTTCTGGAAA   CTAAATAAAA   TCTTTTATTT   ATCATGGCTC
 761   GTATTCTAGT   GGTTTTAGCT   GGTGGTATTG   TTGAGTCAGG
 801   ACTAAAGCCT   GGACTACTGA   GATCCTGTCT   TTAACAAATT
 841   GAACTAATCG   ATtcattagc   tagcTCCTGC   TGGCGGGGC
 881   TGAGTGGGAG   TGGGGGACGG   GGAAATCAAT   GTGGGAGTCG
 921   AATTAGAGGC   GGGGGGAGAC   TTGGCAGGTT   TGGGTAGGGG
 961   ATTAGGTCGC   GGGAGCGAAA   GTTGGTCTGC   CAGGACGGGG
1001   TTCGGTCCTA   TCGGGACCCG   AGGTCCTAGA   TTTTGATATC
1041   TGAGTCGGAT   CCCGAAAGTA   AGCCCCGGGT   CCCGCCCAGA
1081   GACATAAAGA   CGTAGACCCC   AATAGTGTCC   AGTTGTCCAT
1121   GAGGTGACCT   GTTTCCCGGC   GTTTGTAAAC   TGGATAGCCA
1161   AGGGATTGCA   CCACTTATTG   TCTTTGCATA   CCTGGACAGC
1201   CTGGCTAGTG   GTGAGATTGT   TGTCCACTGT   GATGTAGTCC
1241   CAAGAGGAGG   AGGGCTTCCA   GTATACTCTA   CCGGTTGTCT
1281   CGCAGCCCCA   AGAGGCACAG   TAGAAGGAGT   CTGGACCTCC
1321   ACAGGACTTG   GCTTCCCGGG   GGCGATGTGA   CCCGGGGCAG
1361   ACATAAAATC   CCTCACTTGA   TTTATGAGTT   ACCTGGTCTA
1401   GCTTAAGTCT   GTTCCAGGCA   GTGTTGCACC   GAGGGGTGAG
1441   GGAGGTCAAG   GGCTCGTCGC   AGTCTCTGGA   ACAGCCTGCA
1481   CTGCTCCCGC   TGCTCCCTGA   GCAACAAGGG   GGCCCCGGGG
1521   GCGAGGAATA   GGGGGCCTGA   TACTCTAGCC   CCCAGTGGGG
1561   CGGCCCACTG   AGAGCTAACA   TACACAAATC   TGGGGTGAGG
1601   ACTGGCCACC   AAGTCCACAG   AGGGTGGTTG   CCTGATATTG
```

FIG. 3B

```
             |   10       |   20       |   30       |   40
1641    CCCATACTGT  CTCCCGATCC  CCATTGGTCA  CTTCCCAGGT
1681    AATGTTGTAG  ACCTGGTGAG  GGCTGGAGCC  GGGTGCTGCG
1721    GATCTGGCCC  CTTTGAGAGA  CAGGAAGAGA  ATTAAGGGGA
1761    TTAGGAGGTC  CCGCGGGTCA  ATCTTATCTT  TAGGGGATTT
1801    TGGGAGCGTT  GAACACGCCA  TGTCGATTCT  GCTGGTGGCT
1841    CAATCCTGGT  GTCGGCAGCC  TTTACGTGGG  CAGCGTGGAT
1881    CCACGCTGCA  ATGCCGTCTA  CTTTGAGAGC  GGTGGGGGTA
1921    GTCAGTAGGA  CGGTATAGGG  TCCTTTCCAG  CGGGGTTCTA
1961    GATTTTTAGT  TTGGTGTCTG  CGGACCCACA  CTGTGTCACC
2001    GACCCGGAAA  GGGTGAGGTA  CTACCGGCCG  GTCTAGTTGC
2041    TCTTGGTAAG  CTGCCGCCAA  CGGTCTCCAG  ACTTCGTGCT
2081    GGACCAGGTA  GAGTGCCTGT  AAATGAGCTT  GGAGAGAGGG
2121    GTTATGAGTA  ACCTTTGCCA  TGTCAGGATC  AGGGAAGTTT
2161    ACAAGGGGCG  GGGGTGCCCC  ATATAAGATT  TCATATGGGG
2201    TGAGACCGTG  GGGGCCCGGC  GTGTTGCGGG  CTCGATACAG
2241    GGCAAGGGGA  AGCAGGAGCA  CCCAGTCCCT  AGAGCCAGTT
2281    GCAAGCGTCA  ATTTAGTTAA  AGTCTCCTTG  ATTGTCCTAT
2321    TCATTCTTTC  TACCTGACCT  GAACTCTGGG  GTCTGTAAGC
2361    ACAATGTAGT  TTCCAATCAA  CCCCAATAA   ATCGGCTACT
2401    GTCTGACTTA  CCTTGGAGAC  GAAGGCAGGC  CCATTGTCGG
2441    TTCCCAATAC  CTGTGGCATG  CCGAATCTGG  GGAAGATTTC
2481    TTCTAGTAGC  TTCTTGGTTA  CAACTTTGGC  AGTTTCTTTC
2521    TTGGTTGGGA  AAGCTTCTAC  CCATCCAGAG  AAAGTGTCTA
2561    TGAAAACTAA  AAGATATTTA  TACCCATACA  GGCCAGGTTT
2601    TACCTCAGTG  AAATCAATTT  CCCAGTGGGT  GCCGGGTCGG
2641    TGCCCTCGAA  CTCTAGTCCC  TTGTTTGACG  GCAGACTTGC
2681    TGGCATTGAC  CTGTGCACAG  GCTTGGCAAG  TCTCAGTGAT
2721    GTCTTTGAGC  GTTCGATCCC  GGTTCAGCAT  GTAATAAGGA
2761    CAGTAGTTCC  TTTCTAGAAG  AGCCTTTGTT  TTTGAGAAAC
2801    TGAGGTGGGT  CAATTGATGA  AGAAAATCTA  ATAGTTCAAA
2841    GGTGAATTGA  TCAGGCATTA  CAGGCTTTCC  CTGATAAACC
2881    CAACACTTCT  TTGCATCGTC  ATAAGTGGCC  CCTAGTTTAG
2921    TCAGATCTTT  TATGTCAGTC  ACCGTATAGT  GAAAATGTTC
2961    ATGAGTATAG  GGGGCTGAAT  TTTCTATCAG  AAGTGTGGAA
3001    GTCTCTGGAG  TTTCTCTAGT  GGCTACTTCT  CGGGCCGCTT
3041    GGTCGGCCAT  CCTGTTGCCC  CTTGCCTCCG  CGCGGTTTCC
3081    CTTCTGATGT  CCCGGGCAAT  GAATTATGCT  AAGTCTTTTG
3121    GGCAGGAAGA  GAGCCTTCAG  TAGGGCCAAG  ATCTCGTCCT
3161    TATTTTTGAT  TTCTTTTCCT  TCTGATGTGA  GCAACCCGCG
3201    CCTTCTATAT  ATTTCTCCGT  GAATATGGGC  AGTGGCAAAA
3241    GCATAACGGC  TATCGGTGTA  AACATTCAGC  TTCTTACCTT
3281    CTGCCATTTT  TAAGGCTTGG  GTGAGCGCTA  TCAACTCAGC
3321    TCTTTGGGCC  GATGTCCCGG  CTGGCAGTGC  TTTGGCCCAG
```

FIG. 3C

```
             |       10         |       20         |       30         |       40
3361    ACTACCTCGG   TCTCGGTGGT   TACTGCTGCT   CCGGCCTTGC
3401    GCTGCCCCTC   TTGCAGGAAG   CTGCTCCCAT   CTGTGTACCA
3441    GGTGTGGTCA   GCGTCTGGGA   GAGGCTGGTC   CGTAAGATCT
3481    GGTCTAGTTC   CGTGGGCTTC   AGCCAAGATG   TCAAGGCAGT
3521    CATGTTGCAG   CCCCTCCTCA   GGTAGAGGGA   GCAGCGTAGC
3561    TGGGTTTAGG   GCCACTATTG   GTCCGAACTG   GACTCGGTCC
3601    GTGTCCAGAA   GCAGAGCCTG   GTAGTGGGTC   ATTCGGGCGT
3641    TGGAGAGCCA   GCGATCAGGG   GGTTGCTTAA   CTAGTGCCTC
3681    TACTGCATGG   GGGGCCAGAA   TGACTAGTGG   CTGTCCCATG
3721    GTGAGCTTGC   CAGCGTCTTT   GGTCAGAACG   GCGATGGCTG
3761    CTACCATCCG   TAGGCAAGGG   GGCCACCCAG   CTGCCACTGG
3801    GTCTAGCTTT   TTGGACAGGT   AGGCCACCGG   CCGACGCCAA
3841    GGCCCCAGTT   TTTGCGTTAG   GACACCTTTG   GCGTAGCCCT
3881    GCTTCTCGTC   AACAAAAAGT   TCGAAGGGCT   TAGTCAAGTC
3921    TGGCAATCCC   AGGGCAGGGG   CAGTTAAGAG   AGCCTGCTTG
3961    ATCTCTTGGT   AGGCCTTTTG   CTGGTCTGGG   CCCCACTCAA
4001    ACAGAGTCCC   CGTTTTGGTG   AGAGGGTACA   AGGGGGCTGC
4041    CATTTCTGCA   AACCCAGGGA   TCCAGAGGCG   ACAGAAGCCT
4081    GCCGTCCCTA   GGAACTCCCT   TAGTTGTCGA   GGGGTCTTCG
4121    GAGTAGGCTG   CCCCATCACA   GTCTCTTTTC   TGGCCTCAGT
4161    CAGCCATCTC   TGACCCTCTT   TTAGAAGATA   CCCCAGATAC
4201    TTGACCTGTT   TCTGGCAAAT   TTGGGCTTTC   TTGGCCGAGG
4241    CCCGATATCC   GAGGTCCCCT   AGGGTTTGTA   ACAGGGCCCG
4281    CGTACCTTGT   TGACAGTCAA   GCTCAGAAGT   GGCGGCCAGC
4321    AGTAAGTCAT   CTACATACTG   GAGCAGAATC   AGGTCTGGGT
4361    GCTGGATCCG   GAAGTCTGCG   AGGTCCCTGT   GCAGGGCTTC
4401    ATCAAACAGG   GTGGGACTGT   TTTTGAAACC   CTGCGGGAGT
4441    CTGGTCCAGG   TTAATTGTCC   TGAGATTCCC   ATCTCTGGAT
4481    CTCTCCACTC   AAAGGCGAAG   AGAGACTGAC   TGGTGGGGTG
4521    GAGTCTCAGG   CAGAAAAAAG   CATCTTTTAA   GTCAAGCACA
4561    GTGTACCACT   GGTGGGACGG   TGGGAGCCCG   CTCAAGAGGT
4601    TGTAAGGGTT   GGGCACGGTG   GGGTGGATGT   CTTCCACCCG
4641    CTTGTTGACT   TCTCTCAGAT   CCTGGACAGG   CCTATAATCA
4681    TTAGTCCCCG   GTTTCTTAAC   GGGTAGCAGG   GGCGTGTTCC
4721    AGGGGGACTG   GCAGGGTACC   AGAATTCCCT   GATCCAGCAG
4761    TCTCTGTATG   TGGGGCTTGA   TCCCCAGTCT   GGCTTCTTGT
4801    GACATGGGGT   ATTGTTTTAT   GGACACGGGG   GTAGAGGTTG
4841    CCTTCAGAGG   TATGATCAGA   GGAGCTTGGC   GAACGGCCAG
4881    CCCCATGCCC   CCGGTTTCTG   CCCAGGCCTG   GGGAAAATCA
4921    GAGAGCCATG   TGGACCCTAG   AGGCACATCT   GGCCCTTTTG
4961    AGGTCTCATG   TAGCCGATAC   TCATCTTCTA   TGTTTAGGGT
5001    CAGCACTTGC   AGGGGCTGTC   CCATTGGTCC   CACAACCTGA
5041    GCTCCTGATC   CCTCAAAGTG   AATTTGGGCT   TTTAGTTTAG
5081    TCAGCAAATC   TCTTCCTAGC   AGAGGATAGG   GGCAATCTGG
```

FIG. 3D

```
            |    10      |    20      |    30      |    40
    5121    TACATGGAGG   AAAGAATGGG   TGACCTTACC   GGTGGCTAGG
    5161    TGCACTCGGC   GATCCGTGGT   CCAGCGATAC   CGCTTCCCTC
    5201    CAGTAGCCCC   TTGGACCCAG   GCAGACTTGT   CACTTAGGGG
    5241    TCCAGGATTT   TGGGTCAGCA   CGGAGTGTTG   GGCCCAGTA
    5281    TCCACTAGGA   AGGTGACGGG   TTGCCCCCCG   ACTCTGAGGG
    5321    TTATCCTGGG   TTCAGGGGGG   GGCTCCTGAC   CCTGACCTCC
    5361    CTAATCGTCT   AAGGTCAGGA   GGGAGGCCTG   GGTCGTGGT
    5401    CCCCGGGGTC   CTCTTGGCTT   CTTGGGGCAA   TCTCTAGCCC
    5441    AATGTCCCTT   TTCTTTGCAG   TAGGCACACT   GGTCGTGGTC
    5481    GAGTTGGGGC   CTCCTTCGCT   CTCCTCCCTG   TCTATCCTGT
    5521    CTCTGCCCGC   TAACGACAGT   AGCCAGCAAC   TTACTCATTT
    5561    CTCTATGTCT   TCTGCGGTCC   CTCTCCTTCT   CTCTCTGCAC
    5601    ATCCTCTGCC   CTACGGCGTT   CTTCCTTTTC   CTCTGTTTCT
    5641    CTCCTAATAC   GTTCCTCTCT   TTCTTCCGGG   GTTTCTCGTT
    5681    TATTAAAGAT   CTTTTCAGCT   TCCCTCACTA   AGTCTCCTAA
    5721    GGTCTTACTC   TTCAAATCTT   CTAACCGCTC   TAACTTTCGC
    5761    CCGATATCCG   GGGCGGACTG   CCAGATGAAT   GACATGGCCA
    5801    CATTGGTTTC   TTGCCCTGGG   TCCTCAGGGT   CATAAGGAGT
    5841    GTATCTGCGA   TAGGCCTCCT   TGAGTCTCTC   TAAAAAGGCT
    5881    GAGGGAGACT   CATTAGGTCC   CTGGGTTATC   CCTTTTACCT
    5921    TGGCCAAATT   GGTGGGGCTT   CTGCCCGCGT   TTTGGAGACC
    5961    CGCTAGGAGC   AACTGGCGAT   AGTGGACTAG   GTGGTTCCTA
    6001    CCTCGTTGGG   TGTTGTAGTC   CCAGTCGGGA   CGTTCCAAGG
    6041    GAAAAGCATC   ATTAATGTCA   TTGGGCAGCT   GAGTTGGGCG
    6081    TCCGTCCTCC   CCTCGAACCG   CCTTTCGGGC   CTCTAGGAGC
    6121    ACTCGCTGTT   TTTCTTCTCC   CGTCAGCAGG   GTCCCTAATA
    6161    GCTGTTGGCA   GTCATCCCAA   GTGGGCTGAT   GAGTAAGGAG
    6201    AACGGACTCG   ATCAAAGCTG   TCAATTTAGC   TGGGTCCTCG
    6241    GAGAAAGAGG   GGTTGTTATT   TTTCCAGTTA   TAGAGGTCAG
    6281    AGGAGGAAAA   TGGCCAGTAT   TGATACTGTC   CATTCCCTCC
    6321    CAGGCGAAGG   GGGAACGCCT   GAGAGGTAGT   AGAATCCGCC
    6361    ACGGGGGGTT   CTTTTCTTCC   CCGCAGGCGG   GATACCATTG
    6401    GGGAAGGGTC   AGGGGCTCCT   TCTGTAGGGG   CCACTTCTCC
    6441    GCTATCGCCG   TTCCCGTCAG   GAGAGGGTGG   CCCTGGGTCC
    6481    CGGTAAGGCG   GAGGGTCCTC   CGTGAGTAGA   TCAATGAGTG
    6521    GTCCTCCGCT   ATCAGGAAGG   ACTTGAGGCC   TAGGTTTGGT
    6561    GTTTAAAGGA   GAAGTGAGAG   CCGGATAGAG   GGAGGACTGG
    6601    GGCGGGGTCG   AGAGTGGGGG   TTCAGGTGGG   AGAGAGGGGG
    6641    CTGAAGGGGG   AAGAGAGAGG   GGAGGTTTAG   GGTGCACGAA
    6681    GGGTCTGACC   CAGGGAGGGG   GGTCTACTGC   TATAGCTTCC
    6721    CAGGTCACGA   TGTAGGGGAC   CTGATCCGGA   TGTCCATGTG
    6761    GGCCAGGTGA   GAAGACCTTG   ATCTTAACCT   GTGTAATAAT
    6801    GTCTGGGTTA   AAAGTGCCGT   CTCGTGGCCA   TCCGACGTTG
    6841    AAGGTTGGCC   ATTCTGCAGA   GCAGAATGTA   ACCCAGCGCC
```

FIG. 3E

```
             |         10  |         20  |         30  |         40
     6881    TTTTTCTAAC    CTCTACCGAC    AGGTTGTGGG    CTGTCCGTTC
     6921    GACATCCTTC    CAGTGGTCTA    AAGTCAAACT    TAAGGGGGTG
     6961    GTAACAGCCT    GGCCCATGTT    TTCAGACAAA    TACAGAAAAA
     7001    CAGTCAAACA    GAGACAACAC    AGAACGATGC    TGCAGCAGAC
     7041    AAGACGCGCG    GCGCGGCTTC    GGTTCCAAAC    CGAAAGCAAA
     7081    AACTCAGACG    GGGGCGGAAA    CCGTTTTAGC    CCTCTGTCTC
     7121    CTACCAGAAC    CACATACCCC    TCCTCTAAGG    GGGGTGCACC
     7161    AAAGAGTCCA    AAACGATCGG    GATGGTTGGA    CTCTGGCCGG
     7201    GCCACAAAAA    TGGCCCCCGA    AGTCCCTGGG    ACGTCTCCCA
     7241    GGGTTGCGGC    CGGGTGTCTC    GAACTCGTCA    GTTCCACCAC
     7281    GGATCCGCCA    GATACCAATC    TAGTCGGCCA    ACTAGTACAG
     7321    ACACAGGCGC    ATAAAATCAA    TCAAAGACAC    AGGACAATGG
     7361    ACAGACACAG    AACAATTGCT    GGCCAGCTTA    CCTCCCGGTG
     7401    GTGGGTCGGT    GGTCCCTGGG    CAGGGGTCTC    CAGATCCCGG
     7441    ACGAGCCCCC    AAATGAAAGA    CCCCCGAGAC    GGGTAGTCAA
     7481    TCACTCTGAG    GAGACCCTCC    CAAGGAACAG    CGAGACCACG
     7521    AGTCGGATGC    AACAGCAAGA    GGATTTATTG    GATACACGGG
     7561    TACCCGGGCG    ACTCAGTCTA    TCGGAGGACT    GGCGCGCCGA
     7601    GTGAGGGGTT    GTGAGCTCTT    TTATAGAGCT    CGGGAAGCAG
     7641    AAGCGCGCGA    ACAGAAGCGA    GAAGCAGGCT    GATTGGTTAA
     7681    TTCAAATAAG    GCACAGGGTC    ATTTCAGGTC    CTTGGGGGAG
     7721    CCTGGAAACA    TCTGATGGGT    CTTAAGAAAC    TGCTGAGGGT
     7761    TGGGCCATAT    CTGGGGACCA    TCTGTTCTTG    GCCCCGGGCC
     7801    GGGGCCGAAC    CGCGGTGACC    ATCTGTTCTT    GGCCCCGGGC
     7841    CGGGGCCGAA    ACTGCTCACC    GCAGATATCC    TGTTTGGCCC
     7881    AACGTTAGCT    GTTTTCGTGT    ACCCGCCCTT    GATCTGAACT
     7921    TCTCTATTCT    TGGTTTGGTA    TTTTTCCATG    CCTTGCAAAA
     7961    TGGCGTTACT    GCGGCTATCA    GGCTAAatca    gatctgccgg
     8001    tctccctata    gtgagtcgta    ttaatttcga    taagccaggt
     8041    taacctgcat    taatgaatcg    gccaacgcgc    ggggagaggc
     8081    ggtttgcgta    ttgggcgctc    ttccgcttcc    tcgctcactg
     8121    actcgctgcg    ctcggtcgtt    cggctgcggc    gagcggtatc
     8161    agctcactca    aaggcggtaa    tacggttatc    cacagaatca
     8201    ggggataacg    caggaaagaa    catgtgagca    aaaggccagc
     8241    aaaaggccag    gaaccgtaaa    aaggccgcgt    tgctggcgtt
     8281    tttccatagg    ctccgccccc    ctgacgagca    tcacaaaaat
     8321    cgacgctcaa    gtcagaggtg    gcgaaacccg    acaggactat
     8361    aaagatacca    ggcgtttccc    cctggaagct    ccctcgtgcg
     8401    ctctcctgtt    ccgacctgc    cgcttaccgg    atacctgtcc
     8441    gcctttctcc    cttcgggaag    cgtggcgctt    tctcaatgct
     8481    cacgctgtag    gtatctcagt    tcggtgtagg    tcgttcgctc
     8521    caagctgggc    tgtgtgcacg    aaccccccgt    tcagcccgac
     8561    cgctgcgcct    tatccggtaa    ctatcgtctt    gagtccaacc
     8601    cggtaagaca    cgacttatcg    ccactggcag    cagccactgg
```

FIG. 3F

```
             |       10        |       20        |       30        |       40
 8641   taacaggatt agcagagcga ggtatgtagg cggtgctaca
 8681   gagttcttga agtggtggcc taactacggc tacactagaa
 8721   ggacagtatt tggtatctgc gctctgctga agccagttac
 8761   cttcggaaaa agagttggta gctcttgatc cggcaaacaa
 8801   accaccgctg gtagcggtgg ttttttttgtt tgcaagcagc
 8841   agattacgcg cagaaaaaaa ggatctcaag aagatccttt
 8881   gatcttttct acggggtctg acgctcagtg gaacgaaaac
 8921   tcacgttaag ggattttggt catgagatta tcaaaaagga
 8961   tcttcaccta gatccttta aattaaaaat gaagttttaa
 9001   atcaatctaa agtatatatg agtaaacttg gtctgacagt
 9041   taccaatgct taatcagtga ggcacctatc tcagcgatct
 9081   gtctatttcg ttcatccata gttgcctgac tccccgtcgt
 9121   gtagataact acgatacggg agggcttacc atctggcccc
 9161   agtgctgcaa tgataccgcg agacccacgc tcaccggctc
 9201   cagatttatc agcaataaac cagccagccg aagggccga
 9241   gcgcagaagt ggtcctgcaa ctttatccgc ctccatccag
 9281   tctattaatt gttgccggga agctagagta agtagttcgc
 9321   cagttaatag tttgcgcaac gttgttgcca ttgctacagg
 9361   catcgtggtg tcacgctcgt cgtttggtat ggcttcattc
 9401   agctccggtt cccaacgatc aaggcgagtt acatgatccc
 9441   ccatgttgtg caaaaaagcg gttagctcct tcggtcctcc
 9481   gatcgttgtc agaagtaagt tggccgcagt gttatcactc
 9521   atggttatgg cagcactgca taattctctt actgtcatgc
 9561   catccgtaag atgcttttct gtgactggtg agtactcaac
 9601   caagtcattc tgagaatagt gtatgcggcg accgagttgc
 9641   tcttgcccgg cgtcaatacg ggataatacc gcgccacata
 9681   gcagaacttt aaaagtgctc atcattggaa aacgttcttc
 9721   ggggcgaaaa ctctcaagga tcttaccgct gttgagatcc
 9761   agttcgatgt aacccactcg tgcacccaac tgatcttcag
 9801   catcttttac tttcaccagc gtttctgggt gagcaaaaac
 9841   aggaaggcaa aatgccgcaa aaaagggaat aagggcgaca
 9881   cggaaatgtt gaatactcat actcttcctt tttcaatatt
 9921   attgaagcat ttatcagggt tattgtctca tgagcggata
 9961   catatttgaa tgtatttaga aaataaaca aatagggggtt
10001   ccgcgcacat ttccccgaaa agtgccacct gacgtctaag
10041   aaaccattat tatcatgaca ttaacctata aaaataggcg
10081   tatcacgagg cccttttcgtc tcgcgcgttt cggtgatgac
10121   ggtgaaaacc tctgacacat gcagctcccg gagacggtca
10161   cagcttgtct gtaagcggat gccgggagca gacaagcccg
10201   tcagggcgcg tcagcgggtg ttggcgggtg tcggggctgg
10241   cttaactatg cggcatcaga gcagattgta ctgagagtgc
10281   accatatgga catattgtcg ttagaacgcg gctacaatta
10321   atacataacc ttatgtatca tacacatacg atttaggtga
10361   cactata (SEQ ID NO: 9)
```

```
            |    10         |    20         |    30         |    40
  1   MACSTLPKSP     KDKIDPRDLL     IPLILFLSLK     GARSAAPGSS
 41   PHQVYNITWE     VTNGDRETVW     AISGNHPLWT     WWPVLTPDLC
 81   MLALSGPPHW     GLEYQAPYSS     PPGPPCCSGS     SGSSAGCSRD
121   CDEPLTSLTP     RCNTAWNRLK     LDQVTHKSSE     GFYVCPGSHR
161   PREAKSCGGP     DSFYCASWGC     ETTGRVYWKP     SSSWDYITVD
201   NNLTTSQAVQ     VCKDNKWCNP     LAIQFTNAGK     QVTSWTTGHY
241   WGLRLYVSGR     DPGLTFGIRL     RYQNLGPRVP     IGPNPVLADQ
281   LSLPRPNPLP     KPAKSPPASN     STPTLISPSP     TPTQPPPAGA
321   SZZ  (SEQ ID NO: 10)
```

FIG. 3G

```
            |    10         |    20         |    30         |    40
  1   AAPGSSPHQV     YNITWEVTNG     DRETVWAISG     NHPLWTWWPV
 41   LTPDLCMLAL     SGPPHWGLEY     QAPYSSPPGP     PCCSGSSGSS
 81   AGCSRDCDEP     LTSLTPRCNT     AWNRLKLDQV     THKSSEGFYV
121   CPGSHRPREA     KSCGGPDSFY     CASWGCETTG     RVYWKPSSSW
161   DYITVDNNLT     TSQAVQVCKD     NKWCNPLAIQ     FTNAGKQVTS
201   WTTGHYWGLR     LYVSGRDPGL     TFGIRLRYQN     LGPRVPIGPN
241   PVLADQLSLP     RPNPLPKPAK     SPPASNSTPT     LISPSPTPTQ
281   PPPAGASZZ (SEQ ID NO: 11)
```

FIG. 3H

Secreted truncated fusion protein

Viral chimeric insertion protein

HIV insert AS
263

HIV insert AS GA
263 gp70 (SU) | p15E (TM)

FIG. 4B

Structure of MuLV/HIV chimeric glycoproteins

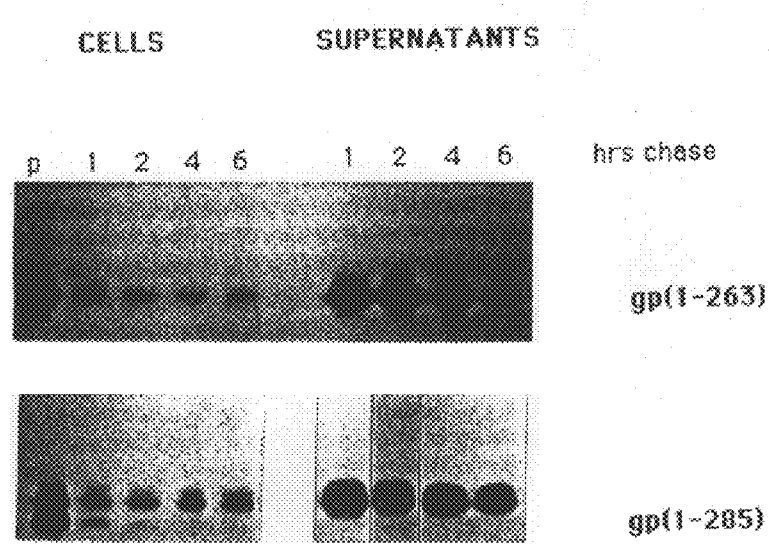
FIG. 5
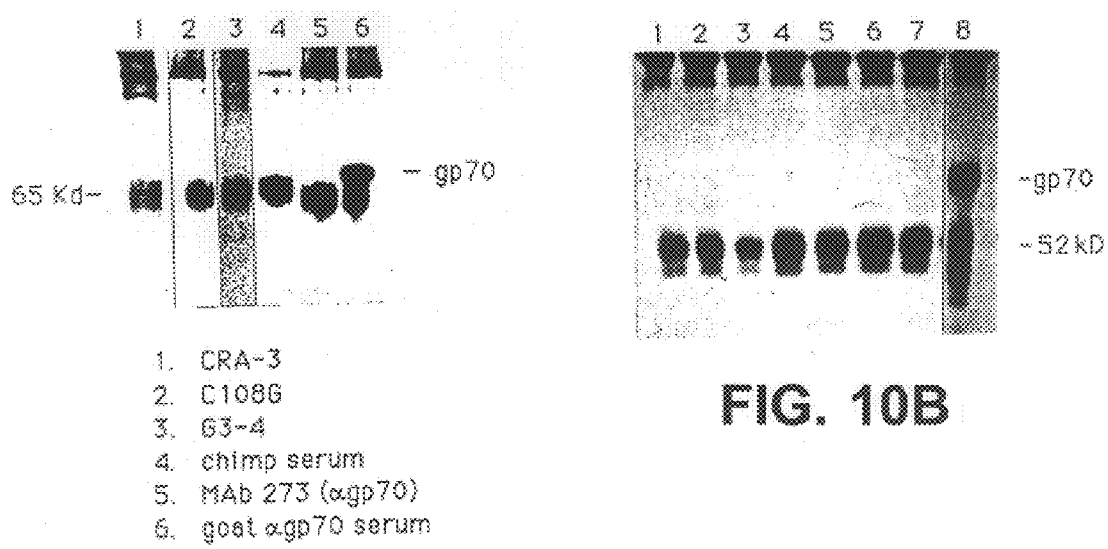
1. CRA-3
2. C108G
3. 63-4
4. chimp serum
5. MAb 273 (αgp70)
6. goat αgp70 serum
FIG. 6B
FIG. 10B Immunoprecipitation of gp(1-263)-V1/V2 fusion glycoprotein
by sera of a group of HIV-seropositive hemophiliacs A - goat anti-gp70
B - C108G
C - CRA3

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:1:

CTCAGCCCCC GCCAGCAGGA GCTAGCTAAT GAATCGATAA CC          42

(2) INFORMATION FOR SEQ ID NO:2:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:2:

GGTTATCGAT TCATTAGCTA GCGGGGGGAG ACTTGGCAGG TT          42

(2) INFORMATION FOR SEQ ID NO:3:

(i) SEQUENCE CHARACTERISTICS:
      (A) LENGTH: 21 base pairs
      (B) TYPE: nucleic acid (C) STRANDEDNESS: single
            (D) TOPOLOGY: linear (ii) MOLECULE TYPE: Genomic DNA (xi) SEQUENCE DESCRIPTION: SEQ ID NO:3:

CCAAGAAGCT TCTAGAAGAA A                                                        21

(2) INFORMATION FOR SEQ ID NO:4:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:4:

CATCGCTAGC CTAAAGCCAT GTGTAAAATT A                                             31

(2) INFORMATION FOR SEQ ID NO:5:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:5:

ACTGATCGAT TCATTAGGAT ACCTTTGGAC AGGCC                                         35

(2) INFORMATION FOR SEQ ID NO:6:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:6:

CGGTGCTAGC TCTGTAGAAA TTAATTGT                                                 28

(2) INFORMATION FOR SEQ ID NO:7:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:7:

CTAGATCGAT CTATTAGGCG CCTGCTCTAC TAATGTTACA                                    40

(2) INFORMATION FOR SEQ ID NO:8:

(i) SEQUENCE CHARACTERISTICS:
            (A) LENGTH: 8323 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:8:

```
GCGCCAGTCC TCCGATAGAC TGAGTCGCCC GGGTACCCGT GTATCCAATA AATCCTCTTG      60
CTGTTGCATC CGACTCGTGG TCTCGCTGTT CCTTGGGAGG GTCTCCTCAG AGTGATTGAC     120
TACCCGTCTC GGGGGTCTTT CATTTGGGGG CTCGTCCGGG ATCTGGAGAC CCCTGCCCAG     180
GGACCACCGA CCCACCACCG GGAGGTAAGC TGGCCAGCAA TTGTTCTGTG TCTGTCCATT     240
GTCCTGTGTC TTTGATTGAT TTTATGCGCC TGTGTCTGTA CTAGTTGGCC GACTAGATTG     300
GTATCTGGCG GATCCGTGGT GGAACTGACG AGTTCGAGAC ACCCGGCCGC AACCCTGGGA     360
GACGTCCCAG GGACTTCGGG GGCCATTTTT GTGGCCCGGC CAGAGTCCAA CCATCCCGAT     420
CGTTTTGGAC TCTTTGGTGC ACCCCCCTTA GAGGAGGGGT ATGTGGTTCT GGTAGGAGAC     480
AGAGGGCTAA AACGGTTTCC GCCCCCGTCT GAGTTTTTGC TTTCGGTTTG GAACCGAAGC     540
CGCGCCGCGC GTCTTGTCTG CTGCAGCATC GTTCTGTGTT GTCTCTGTTT GACTGTTTTT     600
CTGTATTTGT CTGAAAACAT GGGCCAGGCT GTTACCACCC CCTTAAGTTT GACTTTAGAC     660
CACTGGAAGG ATGTCGAACG GACAGCCCAC AACCTGTCGG TAGAGGTTAG AAAAAGGCGC     720
TGGGTTACAT TCTGCTCTGC AGAATGGCCA ACCTTCAACG TCGGATGGCC ACGAGACGGC     780
ACTTTTAACC CAGACATTAT TACACAGGTT AAGATCAAGG TCTTCTCACC TGGCCCACAT     840
GGACATCCGG ATCAGGTCCC CTACATCGTG ACCTGGGAAG CTATAGCAGT AGACCCCCCT     900
CCCTGGGTCA GACCCTTCGT GCACCCTAAA CCTCCCCTCT CTCTTCCCCC TTCAGCCCCC     960
TCTCTCCCAC CTGAACCCCC ACTCTCGACC CCGCCCAGT CCTCCCTCTA TCCGGCTCTC    1020
ACTTCTCCTT TAAACACCAA ACCTAGGCCT CAAGTCCTTC CTGATAGCGG AGGACCACTC    1080
ATTGATCTAC TCACGGAGGA CCCTCCGCCT TACCGGGACC CAGGGCCACC CTCTCCTGAC    1140
GGGAACGGCG ATAGCGGAGA AGTGGCCCCT ACAGAAGGAG CCCCTGACCC TTCCCCAATG    1200
GTATCCCGCC TGCGGGAAG AAAAGAACCC CCCGTGGCGG ATTCTACTAC CTCTCAGGCG    1260
TTCCCCCTTC GCCTGGGAGG GAATGGACAG TATCAATACT GGCCATTTTC CTCCTCTGAC    1320
CTCTATAACT GGAAAAATAA CAACCCCTCT TTCTCCGAGG ACCCAGCTAA ATTGACAGCT    1380
TTGATCGAGT CCGTTCTCCT TACTCATCAG CCCACTTGGG ATGACTGCCA ACAGCTATTA    1440
GGGACCCTGC TGACGGGAGA AGAAAAACAG CGAGTGCTCC TAGAGGCCCG AAAGGCGGTT    1500
CGAGGGGAGG ACGGACGCCC AACTCAGCTG CCCAATGACA TTAATGATGC TTTTCCCTTG    1560
GAACGTCCCG ACTGGGACTA CAACACCCAA CGAGGTAGGA ACCACCTAGT CCACTATCGC    1620
CAGTTGCTCC TAGCGGGTCT CCAAAACGCG GGCAGAAGCC CCACCAATTT GGCCAAGGTA    1680
AAAGGGATAA CCCAGGGACC TAATGAGTCT CCCTCAGCCT TTTTAGAGAG ACTCAAGGAG    1740
GCCTATCGCA GATACACTCC TTATGACCCT GAGGACCCAG GGCAAGAAAC CAATGTGGCC    1800
ATGTCATTCA TCTGGCAGTC CGCCCCGGAT ATCGGGCGAA AGTTAGAGCG GTTAGAAGAT    1860
TTGAAGAGTA AGACCTTAGG AGACTTAGTG AGGGAAGCTG AAAAGATCTT TAATAAACGA    1920
GAAACCCCGG AAGAAAGAGA GGAACGTATT AGGAGAGAAA CAGAGGAAAA GGAAGAACGC    1980
CGTAGGGCAG AGGATGTGCA GAGAGAGAAG GAGAGGGACC GCAGAAGACA TAGAGAAATG    2040
AGTAAGTTGC TGGCTACTGT CGTTAGCGGG CAGAGACAGG ATAGACAGGG AGGAGAGCGA    2100
AGGAGGCCCC AACTCGACCA CGACCAGTGT GCCTACTGCA AAGAAAAGGG ACATTGGGCT    2160
AGAGATTGCC CCAAGAAGCC AAGAGGACCC CGGGGACCAC GACCCCAGGC CTCCCTCCTG    2220
ACCTTAGACG ATTAGGAGG TCAGGGTCAG GAGCCCCCCC CTGAACCCAG GATAACCCTC    2280
AGAGTCGGGG GGCAACCCGT CACCTTCCTA GTGGATACTG GGCCCAACA CTCCGTGCTG    2340
```

```
ACCCAAAATC CTGGACCCCT AAGTGACAAG TCTGCCTGGG TCCAAGGGGC TACTGGAGGG    2400

AAGCGGTATC GCTGGACCAC GGATCGCCGA GTGCACCTAG CCACCGGTAA GGTCACCCAT    2460

TCTTTCCTCC ATGTACCAGA TTGCCCCTAT CCTCTGCTAG GAAGAGATTT GCTGACTAAA    2520

CTAAAAGCCC AAATTCACTT TGAGGGATCA GGAGCTCAGG TTGTGGGACC AATGGGACAG    2580

CCCCTGCAAG TGCTGACCCT AAACATAGAA GATGAGTATC GGCTACATGA GACCTCAAAA    2640

GGGCCAGATG TGCCTCTAGG GTCCACATGG CTCTCTGATT TTCCCCAGGC CTGGGCAGAA    2700

ACCGGGGGCA TGGGGCTGGC CGTTCGCCAA GCTCCTCTGA TCATACCTCT GAAGGCAACC    2760

TCTACCCCCG TGTCCATAAA ACAATACCCC ATGTCACAAG AAGCCAGACT GGGGATCAAG    2820

CCCCACATAC AGAGACTGCT GGATCAGGGA ATTCTGGTAC CCTGCCAGTC CCCCTGGAAC    2880

ACGCCCCTGC TACCCGTTAA GAAACCGGGG ACTAATGATT ATAGGCCTGT CCAGGATCTG    2940

AGAGAAGTCA ACAAGCGGGT GGAAGACATC CACCCCACCG TGCCCAACCC TTACAACCTC    3000

TTGAGCGGGC TCCCACCGTC CCACCAGTGG TACACTGTGC TTGACTTAAA AGATGCTTTT    3060

TTCTGCCTGA GACTCCACCC CACCAGTCAG TCTCTCTTCG CCTTTGAGTG GAGAGATCCA    3120

GAGATGGGAA TCTCAGGACA ATTAACCTGG ACCAGACTCC CGCAGGGTTT CAAAAACAGT    3180

CCCACCCTGT TTGATGAAGC CCTGCACAGG GACCTCGCAG ACTTCCGGAT CCAGCACCCA    3240

GACCTGATTC TGCTCCAGTA TGTAGATGAC TTACTGCTGG CCGCCACTTC TGAGCTTGAC    3300

TGTCAACAAG GTACGCGGGC CCTGTTACAA ACCCTAGGGG ACCTCGGATA TCGGGCCTCG    3360

GCCAAGAAAG CCCAAATTTG CCAGAAACAG GTCAAGTATC TGGGGTATCT TCTAAAAGAG    3420

GGTCAGAGAT GGCTGACTGA GGCCAGAAAA GAGACTGTGA TGGGGCAGCC TACTCCGAAG    3480

ACCCCTCGAC AACTAAGGGA GTTCCTAGGG ACGGCAGGCT TCTGTCGCCT CTGGATCCCT    3540

GGGTTTGCAG AAATGGCAGC CCCCTTGTAC CCTCTCACCA AAACGGGGAC TCTGTTTGAG    3600

TGGGGCCCAG ACCAGCAAAA GGCCTACCAA GAGATCAAGC AGGCTCTCTT AACTGCCCCT    3660

GCCCTGGGAT TGCCAGACTT GACTAAGCCC TTCGAACTTT TTGTTGACGA GAAGCAGGGC    3720

TACGCCAAAG GTGTCCTAAC GCAAAAACTG GGGCCTTGGC GTCGGCCGGT GGCCTACCTG    3780

TCCAAAAAGC TAGACCCAGT GGCAGCTGGG TGGCCCCCTT GCCTACGGAT GGTAGCAGCC    3840

ATCGCCGTTC TGACCAAAGA CGCTGGCAAG CTCACCATGG GACAGCCACT AGTCATTCTG    3900

GCCCCCCATG CAGTAGAGGC ACTAGTTAAG CAACCCCCTG ATCGCTGGCT CTCCAACGCC    3960

CGAATGACCC ACTACCAGGC TCTGCTTCTG GACACGGACC GAGTCCAGTT CGGACCAATA    4020

GTGGCCCTAA ACCCAGCTAC GCTGCTCCCT CTACCTGAGG AGGGGCTGCA ACATGACTGC    4080

CTTGACATCT TGGCTGAAGC CCACGGAACT AGACCAGATC TTACGGACCA GCCTCTCCCA    4140

GACGCTGACC ACACCTGGTA CACAGATGGG AGCAGCTTCC TGCAAGAGGG GCAGCGCAAG    4200

GCCGGAGCAG CAGTAACCAC CGAGACCGAG GTAGTCTGGG CCAAAGCACT GCCAGCCGGG    4260

ACATCGGCCC AAAGAGCTGA GTTGATAGCG CTCACCCAAG CCTTAAAAAT GGCAGAAGGT    4320

AAGAAGCTGA ATGTTTACAC CGATAGCCGT TATGCTTTTG CCACTGCCCA TATTCACGGA    4380

GAAATATATA GAAGGCGCGG GTTGCTCACA TCAGAAGGAA AAGAAATCAA AAATAAGGAC    4440

GAGATCTTGG CCCTACTGAA GGCTCTCTTC CTGCCCAAAA GACTTAGCAT AATTCATTGC    4500

CCGGGACATC AGAAGGGAAA CCGCGCGGAG GCAAGGGGCA ACAGGATGGC CGACCAAGCG    4560

GCCCGAGAAG TAGCCACTAG AGAAACTCCA GAGACTTCCA CACTTCTGAT AGAAAATTCA    4620

GCCCCCTATA CTCATGAACA TTTTCACTAT ACGGTGACTG ACATAAAAGA TCTGACTAAA    4680

CTAGGGGCCA CTTATGACGA TGCAAAGAAG TGTTGGGTTT ATCAGGGAAA GCCTGTAATG    4740
```

-continued

```
CCTGATCAAT TCACCTTTGA ACTATTAGAT TTTCTTCATC AATTGACCCA CCTCAGTTTC    4800

TCAAAAACAA AGGCTCTTCT AGAAAGGAAC TACTGTCCTT ATTACATGCT GAACCGGGAT    4860

CGAACGCTCA AAGACATCAC TGAGACTTGC CAAGCCTGTG CACAGGTCAA TGCCAGCAAG    4920

TCTGCCGTCA AACAAGGGAC TAGAGTTCGA GGGCACCGAC CCGGCACCCA CTGGGAAATT    4980

GATTTCACTG AGGTAAAACC TGGCCTGTAT GGGTATAAAT ATCTTTTAGT TTTCATAGAC    5040

ACTTTCTCTG GATGGGTAGA AGCTTTCCCA ACCAAGAAAG AAACTGCCAA AGTTGTAACC    5100

AAGAAGCTAC TAGAAGAAAT CTTCCCCAGA TTCGGCATGC CACAGGTATT GGGAACCGAC    5160

AATGGGCCTG CCTTCGTCTC CAAGGTAAGT CAGACAGTAG CCGATTTACT GGGGGTTGAT    5220

TGGAAACTAC ATTGTGCTTA CAGACCCCAG AGTTCAGGTC AGGTAGAAAG AATGAATAGG    5280

ACAATCAAGG AGACTTTAAC TAAATTGACG CTTGCAACTG GCTCTAGGGA CTGGGTGCTC    5340

CTGCTTCCCC TAGCCCTGTA TCGAGCCCGC AACACGCCGG GCCCCATGG TCTCACCCCA    5400

TATGAAATCT TATATGGGGC ACCCCCGCCC CTTGTAAACT TCCCTGATCC TGACATGGCA    5460

AAGGTTACTC ATAACCCCTC TCTCCAAGCC CATTTACAGG CACTCTACCT GGTCCAGCAC    5520

GAAGTCTGGA GACCGTTGGC GGCAGCTTAC CAAGAACAAC TGGACCGGCC GGTAGTGCCT    5580

CACCCTTTCC GAGTCGGTGA CACAGTGTGG GTCCGCAGAC ACCAAACTAA AAATCTAGAA    5640

CCCCGCTGGA AAGGACCTTA TACCGTCCTA CTGACTACCC CCACCGCTCT CAAAGTGGAC    5700

GGCATTGCAG CGTGGATCCA CGCTGCCCAC GTAAAGGCTG CCGACACCAG GATTGAGCCA    5760

CCATCGGAAT CGACATGGCG TGTTAACGC TCTCAAAATC CCCTAAAGAT AAGATTGACC    5820

CGCGGGACCT CCTAATCCCC TTAATTCTCT TCCTGTCTCT CAAAGGGGCC AGATCCGCAG    5880

CACCCGGCTC CAGCCCTCAC CAGGTCTACA ACATTACCTG GGAAGTGACC AATGGGGATC    5940

GGGAGACAGT ATGGGCAATA TCAGGCAACC ACCCTCTGTG GACTTGGTGG CCAGTCCTCA    6000

CCCCAGATTT GTGTATGTTA GCTCTCAGTG GGCCGCCCCA CTGGGGGCTA GAGTATCAGG    6060

CCCCCTATTC CTCGCCCCCG GGGCCCCCTT GTTGCTCAGG GAGCAGCGGG AACGTTGCAG    6120

GCTGTGCCAG AGACTGCAAC GAGCCCTTGA CCTCCCTCAC CCCTCGGTGC AACACTGCCT    6180

GGAACAGACT TAAGCTGGAC CAGGTAACTC ATAAATCAAG TGAGGGATTT TATGTCTGCC    6240

CCGGGTCACA TCGCCCCCGG GAAGCCAAGT CCTGTGGGGG TCCAGACTCC TTCTACTGTG    6300

CCTCTTGGGG CTGCGAGACA ACCGGTAGAG TATACTGGAA GCCCTCCTCT TCTTGGGACT    6360

ACATCACAGT AGACAACAAT CTCACCTCTA ACCAGGCTGT TCAGGTATGC AAAGACAATA    6420

AGTGGTGCAA TCCCTTGGCT ATCCGGTTTA CAAACGCCGG GAAACAGGTC ACCTCATGGA    6480

CAACTGGACA CTATTGGGGT CTACGTCTTT ATGTCTCTGG ACAGGACCCA GGGCTTACTT    6540

TCGGGATCCG ACTCAGTTAT CAAAATCTAG GACCTCGGAT CCCAATAGGA CCAAACCCCG    6600

TCCTGGCAGA CCAACTTTCG TTCCCGCTAC CTAATCCCCT ACCCAAACCT GCCAAGTCTC    6660

CCCCCGCCTC TAGTTCGACT CCCACATTGA TTTCCCCGTC CCCCACTCCC ACTCAGCCCC    6720

CGCCAGCAGG AACGGGAGAC AGATTACTAA ATCTAGTACA GGGAGCTTAC CAGGCACTCA    6780

ACCTTACCAA CCCTGATAAA ACTCAAGAGT GCTGGTTATG CCTAGTGTCT GGACCCCCCT    6840

ATTACGAGGG GGTTGCCGTC CTAGGTACTT ATTCCAACCA TACCTCTGCC CCAGCTAACT    6900

GCTCCGTGGC CTCCCAACAC AAGCTGACCC TGTCCGAAGT GACTGGACGG GGACTCTGCA    6960

TAGGAACAGT CCCAAAAACT CACCAGGCCC TGTGCAACAC TACCCTTAAG GCAGGCAAAG    7020

GGTCTTACTA TCTAGTTGCC CCCACAGGAA CTATGTGGGC ATGTAACACT GGACTCACTC    7080

CATGCCTATC TGCCACCGTG CTTAATCGCA CCACTGACTA TTGCGTTCTC GTGGAATTAT    7140
```

```
GGCCCAGGGT CACCTACCAT CCTCCCAGTT ACGTCTATAG CCAGTTTGAA AAATCCCATA      7200

GACATAAAAG AGAACCAGTG TCCTTAACCT TGGCCTTATT ATTAGGTGGG CTAACTATGG      7260

GTGGCATCGC CGCGGGAGTA GGGACAGGAA CTACCGCCCT GGTCGCCACC CAGCAGTTTC      7320

AGCAGCTCCA TGCTGCCGTA CAAGATGATC TCAAAGAAGT CGAAAAGTCA ATTACTAACC      7380

TAGAAAAGTC TCTTACTTCG TTGTCTGAGG TTGTACTGCA GAATCGACGA GGCCTAGACC      7440

TGTTGTTCCT AAAAGAGGGA GGACTGTGTG CTGCCCTAAA AGAAGAATGT TGTTTCTATG      7500

CTGACCATAC AGGCCTAGTA AGAGATAGTA TGGCCAAATT AAGAGAGAGA CTCTCTCAGA      7560

GACAAAAACT ATTTGAGTCG AGCCAAGGAT GGTTCGAAGG ATGGTTTAAC AGATCCCCCT      7620

GGTTTACCAC GTTGATATCC ACCATCATGG GGCCTCTCAT TATACTCCTA CTAATTCTGC      7680

TTTTTGGACC CTGCATTCTT AATCGATTAG TTCAATTTGT TAAAGACAGG ATCTCAGTAG      7740

TCCAGGCTTT AGTCCTGACT CAACAATACC ACCAGCTAAA ACCACTAGAA TACGAGCCAC      7800

AATAAATAAA AGATTTTATT TAGTTTCCAG AAAAAGGGGG GAATGAAAGA CCCCACCAAA      7860

TTGCTTAGCC TGATAGCCGC AGTAACGCCA TTTTGCAAGG CATGGAAAAA TACCAAACCA      7920

AGAATAGAGA AGTTCAGATC AAGGGCGGGT ACACGAAAAC AGCTAACGTT GGGCCAAACA      7980

GGATATCTGC GGTGAGCAGT TTCGGCCCCG GCCCGGGGCC AAGAACAGAT GGTCACCGCG      8040

GTTCGGCCCC GGCCCGGGGC CAAGAACAGA TGGTCCCCAG ATATGGCCCA ACCCTCAGCA      8100

GTTTCTTAAG ACCCATCAGA TGTTTCCAGG CTCCCCAAG GACCTGAAAT GACCCTGTGC       8160

CTTATTTGAA TTAACCAATC AGCCTGCTTC TCGCTTCTGT TCGCGCGCTT CTGCTTCCCG      8220

AGCTCTATAA AAGAGCTCAC AACCCCTCAC TCGGCGCGCC AGTCCTCCGA TAGACTGAGT      8280

CGCCCGGGTA CCCGTGTATC CAATAAATCC TCTTGCTGTT GCA                       8323
```

(2) INFORMATION FOR SEQ ID NO:9:

(i) SEQUENCE CHARACTERISTICS:
        (A) LENGTH: 10367 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:9:

```
GAACTCGAGC AGGGCTAGTA CAGACACAGG CGCATAAAAT CAATCAAAGA CACAGGACAA        60

TGGACAGACA CAGAACAATT GCTGGCCAGC TTACCTCCCG GTGGTGGGTC GGTGGTCCCT       120

GGGCAGGGGT CTCCAGATCC CGGACGAGCC CCCAAATGAA AGACCCCCGA GACGGGTAGT       180

CAATCACTCT GAGGAGACCC TCCCAAGGAA CAGCGAGACC ACGAGTCGGA TGCAACAGCA       240

AGAGGATTTA TTGGATACAC GGGTACCCGG GCGACTCAGT CTATCGGAGG ACTGGCGCGC       300

CGAGTGAGGG GTTGTGAGCT CTTTTATAGA GCTCGGGAAG CAGAAGCGCG CGAACAGAAG       360

CGAGAAGCAG GCTGATTGGT TAATTCAAAT AAGGCACAGG GTCATTTCAG GTCCTTGGGG       420

GAGCCTGGAA ACATCTGATG GGTCTTAAGA AACTGCTGAG GGTTGGGCCA TATCTGGGGA       480

CCATCTGTTC TTGGCCCCGG GCCGGGGCCG AACCGCGGTG ACCATCTGTT CTTGGCCCCG       540

GGCCGGGGCC GAAACTGCTC ACCGCAGATA TCCTGTTTGG CCCAACGTTA GCTGTTTTCG       600

TGTACCCGCC CTTGATCTGA ACTTCTCTAT TCTTGGTTTG GTATTTTTCC ATGCCTTGCA       660

AAATGGCGTT ACTGCGGCTA TCAGGCTAAG CAACTTGGTG GGGTCTTTCA TTCCCCCCTT       720

TTTCTGGAAA CTAAATAAAA TCTTTTATTT ATCATGGCTC GTATTCTAGT GGTTTTAGCT       780

GGTGGTATTG TTGAGTCAGG ACTAAAGCCT GGACTACTGA GATCCTGTCT TTAACAAATT       840
```

-continued

```
GAACTAATCG ATTCATTAGC TAGCTCCTGC TGGCGGGGGC TGAGTGGGAG TGGGGGACGG      900
GGAAATCAAT GTGGGAGTCG AATTAGAGGC GGGGGGAGAC TTGGCAGGTT TGGGTAGGGG      960
ATTAGGTCGC GGGAGCGAAA GTTGGTCTGC CAGGACGGGG TTCGGTCCTA TCGGGACCCG     1020
AGGTCCTAGA TTTTGATATC TGAGTCGGAT CCCGAAAGTA AGCCCGGGT CCCGCCCAGA     1080
GACATAAAGA CGTAGACCCC AATAGTGTCC AGTTGTCCAT GAGGTGACCT GTTTCCCGGC     1140
GTTTGTAAAC TGGATAGCCA AGGGATTGCA CCACTTATTG TCTTTGCATA CCTGGACAGC     1200
CTGGCTAGTG GTGAGATTGT TGTCCACTGT GATGTAGTCC CAAGAGGAGG AGGGCTTCCA     1260
GTATACTCTA CCGGTTGTCT CGCAGCCCCA AGAGGCACAG TAGAAGGAGT CTGGACCTCC     1320
ACAGGACTTG GCTTCCCGGG GGCGATGTGA CCCGGGGCAG ACATAAAATC CCTCACTTGA     1380
TTTATGAGTT ACCTGGTCTA GCTTAAGTCT GTTCCAGGCA GTGTTGCACC GAGGGGTGAG     1440
GGAGGTCAAG GGCTCGTCGC AGTCTCTGGA ACAGCCTGCA CTGCTCCCGC TGCTCCCTGA     1500
GCAACAAGGG GGCCCCGGGG GCGAGGAATA GGGGGCCTGA TACTCTAGCC CCCAGTGGGG     1560
CGGCCCACTG AGAGCTAACA TACACAAATC TGGGGTGAGG ACTGGCCACC AAGTCCACAG     1620
AGGGTGGTTG CCTGATATTG CCCATACTGT CTCCCGATCC CCATTGGTCA CTTCCCAGGT     1680
AATGTTGTAG ACCTGGTGAG GGCTGGAGCC GGGTGCTGCG GATCTGGCCC CTTTGAGAGA     1740
CAGGAAGAGA ATTAAGGGGA TTAGGAGGTC CCGCGGGTCA ATCTTATCTT TAGGGGATTT     1800
TGGGAGCGTT GAACACGCCA TGTCGATTCT GCTGGTGGCT CAATCCTGGT GTCGGCAGCC     1860
TTTACGTGGG CAGCGTGGAT CCACGCTGCA ATGCCGTCTA CTTTGAGAGC GGTGGGGGTA     1920
GTCAGTAGGA CGGTATAGGG TCCTTTCCAG CGGGGTTCTA GATTTTTAGT TTGGTGTCTG     1980
CGGACCCACA CTGTGTCACC GACCCGGAAA GGGTGAGGTA CTACCGGCCG GTCTAGTTGC     2040
TCTTGGTAAG CTGCCGCCAA CGGTCTCCAG ACTTCGTGCT GGACCAGGTA GAGTGCCTGT     2100
AAATGAGCTT GGAGAGAGGG GTTATGAGTA ACCTTTGCCA TGTCAGGATC AGGGAAGTTT     2160
ACAAGGGGCG GGGGTGCCCC ATATAAGATT TCATATGGGG TGAGACCGTG GGGGCCCGGC     2220
GTGTTGCGGG CTCGATACAG GGCAAGGGGA AGCAGGAGCA CCCAGTCCCT AGAGCCAGTT     2280
GCAAGCGTCA ATTTAGTTAA AGTCTCCTTG ATTGTCCTAT TCATTCTTTC TACCTGACCT     2340
GAACTCTGGG GTCTGTAAGC ACAATGTAGT TTCCAATCAA CCCCCAATAA ATCGGCTACT     2400
GTCTGACTTA CCTTGGAGAC GAAGGCAGGC CCATTGTCGG TTCCCAATAC CTGTGGCATG     2460
CCGAATCTGG GGAAGATTTC TTCTAGTAGC TTCTTGGTTA CAACTTTGGC AGTTTCTTTC     2520
TTGGTTGGGA AAGCTTCTAC CCATCCAGAG AAAGTGTCTA TGAAAACTAA AGATATTTA     2580
TACCCATACA GGCCAGGTTT TACCTCAGTG AAATCAATTT CCCAGTGGGT GCCGGGTCGG     2640
TGCCCTCGAA CTCTAGTCCC TTGTTTGACG GCAGACTTGC TGGCATTGAC CTGTGCACAG     2700
GCTTGGCAAG TCTCAGTGAT GTCTTTGAGC GTTCGATCCC GGTTCAGCAT GTAATAAGGA     2760
CAGTAGTTCC TTTCTAGAAG AGCCTTTGTT TTTGAGAAAC TGAGGTGGGT CAATTGATGA     2820
AGAAAATCTA ATAGTTCAAA GGTGAATTGA TCAGGCATTA CAGGCTTTCC CTGATAAACC     2880
CAACACTTCT TTGCATCGTC ATAAGTGGCC CCTAGTTTAG TCAGATCTTT TATGTCAGTC     2940
ACCGTATAGT GAAAATGTTC ATGAGTATAG GGGGCTGAAT TTTCTATCAG AAGTGTGGAA     3000
GTCTCTGGAG TTTCTCTAGT GGCTACTTCT CGGGCCGCTT GGTCGGCCAT CCTGTTGCCC     3060
CTTGCCTCCG CGCGGTTTCC CTTCTGTGT CCCGGGCAAT GAATTATGCT AAGTCTTTTG     3120
GGCAGGAAGA GAGCCTTCAG TAGGGCCAAG ATCTCGTCCT TATTTTTGAT TTCTTTTCCT     3180
TCTGATGTGA GCAACCCGCG CCTTCTATAT ATTTCTCCGT GAATATGGGC AGTGGCAAAA     3240
```

```
GCATAACGGC TATCGGTGTA AACATTCAGC TTCTTACCTT CTGCCATTTT TAAGGCTTGG    3300

GTGAGCGCTA TCAACTCAGC TCTTTGGGCC GATGTCCCGG CTGGCAGTGC TTTGGCCCAG    3360

ACTACCTCGG TCTCGGTGGT TACTGCTGCT CCGGCCTTGC GCTGCCCCTC TTGCAGGAAG    3420

CTGCTCCCAT CTGTGTACCA GGTGTGGTCA GCGTCTGGGA GAGGCTGGTC CGTAAGATCT    3480

GGTCTAGTTC CGTGGGCTTC AGCCAAGATG TCAAGGCAGT CATGTTGCAG CCCCTCCTCA    3540

GGTAGAGGGA GCAGCGTAGC TGGGTTTAGG GCCACTATTG GTCCGAACTG GACTCGGTCC    3600

GTGTCCAGAA GCAGAGCCTG GTAGTGGGTC ATTCGGGCGT TGGAGAGCCA GCGATCAGGG    3660

GGTTGCTTAA CTAGTGCCTC TACTGCATGG GGGGCCAGAA TGACTAGTGG CTGTCCCATG    3720

GTGAGCTTGC CAGCGTCTTT GGTCAGAACG GCGATGGCTG CTACCATCCG TAGGCAAGGG    3780

GGCCACCCAG CTGCCACTGG GTCTAGCTTT TTGGACAGGT AGGCCACCGG CCGACGCCAA    3840

GGCCCCAGTT TTTGCGTTAG GACACCTTTG GCGTAGCCCT GCTTCTCGTC AACAAAAAGT    3900

TCGAAGGGCT TAGTCAAGTC TGGCAATCCC AGGGCAGGGG CAGTTAAGAG AGCCTGCTTG    3960

ATCTCTTGGT AGGCCTTTTG CTGGTCTGGG CCCCACTCAA ACAGAGTCCC CGTTTTGGTG    4020

AGAGGGTACA AGGGGCTGC CATTTCTGCA AACCCAGGGA TCCAGAGGCG ACAGAAGCCT    4080

GCCGTCCCTA GGAACTCCCT TAGTTGTCGA GGGGTCTTCG GAGTAGGCTG CCCCATCACA    4140

GTCTCTTTTC TGGCCTCAGT CAGCCATCTC TGACCCTCTT TTAGAAGATA CCCCAGATAC    4200

TTGACCTGTT TCTGGCAAAT TTGGGCTTTC TTGGCCGAGG CCCGATATCC GAGGTCCCCT    4260

AGGGTTTGTA ACAGGGCCCG CGTACCTTGT TGACAGTCAA GCTCAGAAGT GGCGGCCAGC    4320

AGTAAGTCAT CTACATACTG GAGCAGAATC AGGTCTGGGT GCTGGATCCG GAAGTCTGCG    4380

AGGTCCCTGT GCAGGGCTTC ATCAAACAGG GTGGGACTGT TTTTGAAACC CTGCGGGAGT    4440

CTGGTCCAGG TTAATTGTCC TGAGATTCCC ATCTCTGGAT CTCTCCACTC AAAGGCGAAG    4500

AGAGACTGAC TGGTGGGGTG GAGTCTCAGG CAGAAAAAAG CATCTTTTAA GTCAAGCACA    4560

GTGTACCACT GGTGGGACGG TGGGAGCCCG CTCAAGAGGT TGTAAGGGTT GGGCACGGTG    4620

GGGTGGATGT CTTCCACCCG CTTGTTGACT TCTCTCAGAT CCTGGACAGG CCTATAATCA    4680

TTAGTCCCCG GTTTCTTAAC GGGTAGCAGG GGCGTGTTCC AGGGGGACTG GCAGGGTACC    4740

AGAATTCCCT GATCCAGCAG TCTCTGTATG TGGGGCTTGA TCCCCAGTCT GGCTTCTTGT    4800

GACATGGGGT ATTGTTTTAT GGACACGGGG GTAGAGGTTG CCTTCAGAGG TATGATCAGA    4860

GGAGCTTGGC GAACGGCCAG CCCCATGCCC CCGGTTTCTG CCCAGGCCTG GGGAAAATCA    4920

GAGAGCCATG TGGACCCTAG AGGCACATCT GGCCCTTTTG AGGTCTCATG TAGCCGATAC    4980

TCATCTTCTA TGTTTAGGGT CAGCACTTGC AGGGGCTGTC CCATTGGTCC CACAACCTGA    5040

GCTCCTGATC CCTCAAAGTG AATTTGGGCT TTTAGTTTAG TCAGCAAATC TCTTCCTAGC    5100

AGAGGATAGG GGCAATCTGG TACATGGAGG AAAGAATGGG TGACCTTACC GGTGGCTAGG    5160

TGCACTCGGC GATCCGTGGT CCAGCGATAC CGCTTCCCTC CAGTAGCCCC TTGGACCCAG    5220

GCAGACTTGT CACTTAGGGG TCCAGGATTT TGGGTCAGCA CGGAGTGTTG GCCCCAGTA    5280

TCCACTAGGA AGGTGACGGG TTGCCCCCCG ACTCTGAGGG TTATCCTGGG TTCAGGGGGG    5340

GGCTCCTGAC CCTGACCTCC CTAATCGTCT AAGGTCAGGA GGGAGGCCTG GGGTCGTGGT    5400

CCCCGGGGTC CTCTTGGCTT CTTGGGGCAA TCTCTAGCCC AATGTCCCTT TTCTTTGCAG    5460

TAGGCACACT GGTCGTGGTC GAGTTGGGGC CTCCTTCGCT CTCCTCCCTG TCTATCCTGT    5520

CTCTGCCCGC TAACGACAGT AGCCAGCAAC TTACTCATTT CTCTATGTCT TCTGCGGTCC    5580

CTCTCCTTCT CTCTCTGCAC ATCCTCTGCC CTACGGCGTT CTTCCTTTTC CTCTGTTTCT    5640
```

```
CTCCTAATAC GTTCCTCTCT TTCTTCCGGG GTTTCTCGTT TATTAAAGAT CTTTTCAGCT     5700

TCCCTCACTA AGTCTCCTAA GGTCTTACTC TTCAAATCTT CTAACCGCTC TAACTTTCGC     5760

CCGATATCCG GGGCGGACTG CCAGATGAAT GACATGGCCA CATTGGTTTC TTGCCCTGGG     5820

TCCTCAGGGT CATAAGGAGT GTATCTGCGA TAGGCCTCCT TGAGTCTCTC TAAAAAGGCT     5880

GAGGGAGACT CATTAGGTCC CTGGGTTATC CCTTTTACCT TGGCCAAATT GGTGGGGCTT     5940

CTGCCCGCGT TTTGGAGACC CGCTAGGAGC AACTGGCGAT AGTGGACTAG GTGGTTCCTA     6000

CCTCGTTGGG TGTTGTAGTC CCAGTCGGGA CGTTCCAAGG GAAAAGCATC ATTAATGTCA     6060

TTGGGCAGCT GAGTTGGGCG TCCGTCCTCC CCTCGAACCG CCTTTCGGGC CTCTAGGAGC     6120

ACTCGCTGTT TTTCTTCTCC CGTCAGCAGG GTCCCTAATA GCTGTTGGCA GTCATCCCAA     6180

GTGGGCTGAT GAGTAAGGAG AACGGACTCG ATCAAAGCTG TCAATTTAGC TGGGTCCTCG     6240

GAGAAAGAGG GGTTGTTATT TTTCCAGTTA TAGAGGTCAG AGGAGGAAAA TGGCCAGTAT     6300

TGATACTGTC CATTCCCTCC CAGGCGAAGG GGGAACGCCT GAGAGGTAGT AGAATCCGCC     6360

ACGGGGGTT CTTTTCTTCC CCGCAGGCGG GATACCATTG GGGAAGGGTC AGGGGCTCCT     6420

TCTGTAGGGG CCACTTCTCC GCTATCGCCG TTCCCGTCAG GAGAGGGTGG CCCTGGGTCC     6480

CGGTAAGGCG GAGGGTCCTC CGTGAGTAGA TCAATGAGTG GTCCTCCGCT ATCAGGAAGG     6540

ACTTGAGGCC TAGGTTTGGT GTTTAAAGGA GAAGTGAGAG CCGGATAGAG GGAGGACTGG     6600

GGCGGGGTCG AGAGTGGGGG TTCAGGTGGG AGAGAGGGGG CTGAAGGGGG AAGAGAGAGG     6660

GGAGGTTTAG GGTGCACGAA GGGTCTGACC CAGGGAGGGG GGTCTACTGC TATAGCTTCC     6720

CAGGTCACGA TGTAGGGGAC CTGATCCGGA TGTCCATGTG GGCCAGGTGA GAAGACCTTG     6780

ATCTTAACCT GTGTAATAAT GTCTGGGTTA AAAGTGCCGT CTCGTGGCCA TCCGACGTTG     6840

AAGGTTGGCC ATTCTGCAGA GCAGAATGTA ACCCAGCGCC TTTTTCTAAC CTCTACCGAC     6900

AGGTTGTGGG CTGTCCGTTC GACATCCTTC CAGTGGTCTA AAGTCAAACT TAAGGGGGTG     6960

GTAACAGCCT GGCCCATGTT TTCAGACAAA TACAGAAAAA CAGTCAAACA GAGACAACAC     7020

AGAACGATGC TGCAGCAGAC AAGACGCGCG GCGCGGCTTC GGTTCCAAAC CGAAAGCAAA     7080

AACTCAGACG GGGGCGGAAA CCGTTTTAGC CCTCTGTCTC CTACCAGAAC CACATACCCC     7140

TCCTCTAAGG GGGGTGCACC AAAGAGTCCA AAACGATCGG GATGGTTGGA CTCTGGCCGG     7200

GCCACAAAAA TGGCCCCCGA AGTCCCTGGG ACGTCTCCCA GGGTTGCGGC CGGGTGTCTC     7260

GAACTCGTCA GTTCCACCAC GGATCCGCCA GATACCAATC TAGTCGGCCA ACTAGTACAG     7320

ACACAGGCGC ATAAAATCAA TCAAAGACAC AGGACAATGG ACAGACACAG AACAATTGCT     7380

GGCCAGCTTA CCTCCCGGTG GTGGGTCGGT GGTCCCTGGG CAGGGGTCTC CAGATCCCGG     7440

ACGAGCCCCC AAATGAAAGA CCCCCGAGAC GGGTAGTCAA TCACTCTGAG GAGACCCTCC     7500

CAAGGAACAG CGAGACCACG AGTCGGATGC AACAGCAAGA GGATTATTG GATACACGGG     7560

TACCCGGGCG ACTCAGTCTA TCGGAGGACT GGCGCGCCGA GTGAGGGGTT GTGAGCTCTT     7620

TTATAGAGCT CGGGAAGCAG AAGCGCGCGA ACAGAAGCGA GAAGCAGGCT GATTGGTTAA     7680

TTCAAATAAG GCACAGGGTC ATTTCAGGTC CTTGGGGGAG CCTGGAAACA TCTGATGGGT     7740

CTTAAGAAAC TGCTGAGGGT TGGGCCATAT CTGGGGACCA TCTGTTCTTG GCCCCGGGCC     7800

GGGGCCGAAC CGCGGTGACC ATCTGTTCTT GGCCCCGGGC CGGGGCCGAA ACTGCTCACC     7860

GCAGATATCC TGTTTGGCCC AACGTTAGCT GTTTTCGTGT ACCCGCCCTT GATCTGAACT     7920

TCTCTATTCT TGGTTTGGTA TTTTTCCATG CCTTGCAAAA TGGCGTTACT GCGGCTATCA     7980

GGCTAAATCA GATCTGCCGG TCTCCCTATA GTGAGTCGTA TTAATTTCGA TAAGCCAGGT     8040
```

```
TAACCTGCAT TAATGAATCG GCCAACGCGC GGGGAGAGGC GGTTTGCGTA TTGGGCGCTC    8100

TTCCGCTTCC TCGCTCACTG ACTCGCTGCG CTCGGTCGTT CGGCTGCGGC GAGCGGTATC    8160

AGCTCACTCA AAGGCGGTAA TACGGTTATC CACAGAATCA GGGGATAACG CAGGAAAGAA    8220

CATGTGAGCA AAAGGCCAGC AAAAGGCCAG GAACCGTAAA AAGGCCGCGT TGCTGGCGTT    8280

TTTCCATAGG CTCCGCCCCC CTGACGAGCA TCACAAAAAT CGACGCTCAA GTCAGAGGTG    8340

GCGAAACCCG ACAGGACTAT AAAGATACCA GGCGTTTCCC CCTGGAAGCT CCCTCGTGCG    8400

CTCTCCTGTT CCGACCCTGC CGCTTACCGG ATACCTGTCC GCCTTTCTCC CTTCGGGAAG    8460

CGTGGCGCTT TCTCAATGCT CACGCTGTAG GTATCTCAGT TCGGTGTAGG TCGTTCGCTC    8520

CAAGCTGGGC TGTGTGCACG AACCCCCCGT TCAGCCCGAC CGCTGCGCCT TATCCGGTAA    8580

CTATCGTCTT GAGTCCAACC CGGTAAGACA CGACTTATCG CCACTGGCAG CAGCCACTGG    8640

TAACAGGATT AGCAGAGCGA GGTATGTAGG CGGTGCTACA GAGTTCTTGA AGTGGTGGCC    8700

TAACTACGGC TACACTAGAA GGACAGTATT TGGTATCTGC GCTCTGCTGA AGCCAGTTAC    8760

CTTCGGAAAA AGAGTTGGTA GCTCTTGATC CGGCAAACAA ACCACCGCTG GTAGCGGTGG    8820

TTTTTTTGTT TGCAAGCAGC AGATTACGCG CAGAAAAAAA GGATCTCAAG AAGATCCTTT    8880

GATCTTTTCT ACGGGGTCTG ACGCTCAGTG GAACGAAAAC TCACGTTAAG GGATTTTGGT    8940

CATGAGATTA TCAAAAAGGA TCTTCACCTA GATCCTTTTA AATTAAAAAT GAAGTTTTAA    9000

ATCAATCTAA AGTATATATG AGTAAACTTG GTCTGACAGT TACCAATGCT TAATCAGTGA    9060

GGCACCTATC TCAGCGATCT GTCTATTTCG TTCATCCATA GTTGCCTGAC TCCCCGTCGT    9120

GTAGATAACT ACGATACGGG AGGGCTTACC ATCTGGCCCC AGTGCTGCAA TGATACCGCG    9180

AGACCCACGC TCACCGGCTC CAGATTTATC AGCAATAAAC CAGCCAGCCG GAAGGGCCGA    9240

GCGCAGAAGT GGTCCTGCAA CTTTATCCGC CTCCATCCAG TCTATTAATT GTTGCCGGGA    9300

AGCTAGAGTA AGTAGTTCGC CAGTTAATAG TTTGCGCAAC GTTGTTGCCA TTGCTACAGG    9360

CATCGTGGTG TCACGCTCGT CGTTTGGTAT GGCTTCATTC AGCTCCGGTT CCCAACGATC    9420

AAGGCGAGTT ACATGATCCC CCATGTTGTG CAAAAAAGCG GTTAGCTCCT TCGGTCCTCC    9480

GATCGTTGTC AGAAGTAAGT TGGCCGCAGT GTTATCACTC ATGGTTATGG CAGCACTGCA    9540

TAATTCTCTT ACTGTCATGC CATCCGTAAG ATGCTTTTCT GTGACTGGTG AGTACTCAAC    9600

CAAGTCATTC TGAGAATAGT GTATGCGGCG ACCGAGTTGC TCTTGCCCGG CGTCAATACG    9660

GGATAATACC GCGCCACATA GCAGAACTTT AAAAGTGCTC ATCATTGGAA AACGTTCTTC    9720

GGGGCGAAAA CTCTCAAGGA TCTTACCGCT GTTGAGATCC AGTTCGATGT AACCCACTCG    9780

TGCACCCAAC TGATCTTCAG CATCTTTTAC TTTCACCAGC GTTTCTGGGT GAGCAAAAAC    9840

AGGAAGGCAA AATGCCGCAA AAAAGGGAAT AAGGGCGACA CGGAAATGTT GAATACTCAT    9900

ACTCTTCCTT TTTCAATATT ATTGAAGCAT TTATCAGGGT TATTGTCTCA TGAGCGGATA    9960

CATATTTGAA TGTATTTAGA AAAATAAACA AATAGGGGTT CCGCGCACAT TTCCCCGAAA   10020

AGTGCCACCT GACGTCTAAG AAACCATTAT TATCATGACA TTAACCTATA AAAATAGGCG   10080

TATCACGAGG CCCTTTCGTC TCGCGCGTTT CGGTGATGAC GGTGAAAACC TCTGACACAT   10140

GCAGCTCCCG GAGACGGTCA CAGCTTGTCT GTAAGCGGAT GCCGGGAGCA GACAAGCCCG   10200

TCAGGGCGCG TCAGCGGGTG TTGGCGGGTG TCGGGCTGG CTTAACTATG CGGCATCAGA   10260

GCAGATTGTA CTGAGAGTGC ACCATATGGA CATATTGTCG TTAGAACGCG GCTACAATTA   10320

ATACATAACC TTATGTATCA TACACATACG ATTTAGGTGA CACTATA                 10367
```

(2) INFORMATION FOR SEQ ID NO:10:

(i) SEQUENCE CHARACTERISTICS:
        (A) LENGTH: 323 amino acids
        (B) TYPE: amino acid
        (D) TOPOLOGY: linear (ii) MOLECULE TYPE: peptide (xi) SEQUENCE DESCRIPTION: SEQ ID NO:10:

```
Met Ala Cys Ser Thr Leu Pro Lys Ser Pro Lys Asp Lys Ile Asp Pro
 1               5                  10                  15

Arg Asp Leu Leu Ile Pro Leu Ile Leu Phe Leu Ser Leu Lys Gly Ala
             20                  25                  30

Arg Ser Ala Ala Pro Gly Ser Ser Pro His Gln Val Tyr Asn Ile Thr
         35                  40                  45

Trp Glu Val Thr Asn Gly Asp Arg Glu Thr Val Trp Ala Ile Ser Gly
     50                  55                  60

Asn His Pro Leu Trp Thr Trp Trp Pro Val Leu Thr Pro Asp Leu Cys
 65                  70                  75                  80

Met Leu Ala Leu Ser Gly Pro Pro His Trp Gly Leu Glu Tyr Gln Ala
                 85                  90                  95

Pro Tyr Ser Ser Pro Pro Gly Pro Pro Cys Cys Ser Gly Ser Ser Gly
                100                 105                 110

Ser Ser Ala Gly Cys Ser Arg Asp Cys Asp Glu Pro Leu Thr Ser Leu
            115                 120                 125

Thr Pro Arg Cys Asn Thr Ala Trp Asn Arg Leu Lys Leu Asp Gln Val
        130                 135                 140

Thr His Lys Ser Ser Glu Gly Phe Tyr Val Cys Pro Gly Ser His Arg
145                 150                 155                 160

Pro Arg Glu Ala Lys Ser Cys Gly Gly Pro Asp Ser Phe Tyr Cys Ala
                165                 170                 175

Ser Trp Gly Cys Glu Thr Thr Gly Arg Val Tyr Trp Lys Pro Ser Ser
                180                 185                 190

Ser Trp Asp Tyr Ile Thr Val Asp Asn Asn Leu Thr Thr Ser Gln Ala
            195                 200                 205

Val Gln Val Cys Lys Asp Asn Lys Trp Cys Asn Pro Leu Ala Ile Gln
        210                 215                 220

Phe Thr Asn Ala Gly Lys Gln Val Thr Ser Trp Thr Thr Gly His Tyr
225                 230                 235                 240

Trp Gly Leu Arg Leu Tyr Val Ser Gly Arg Asp Pro Gly Leu Thr Phe
                245                 250                 255

Gly Ile Arg Leu Arg Tyr Gln Asn Leu Gly Pro Arg Val Pro Ile Gly
                260                 265                 270

Pro Asn Pro Val Leu Ala Asp Gln Leu Ser Leu Pro Arg Pro Asn Pro
            275                 280                 285

Leu Pro Lys Pro Ala Lys Ser Pro Ala Ser Asn Ser Thr Pro Thr
        290                 295                 300

Leu Ile Ser Pro Ser Pro Thr Pro Thr Gln Pro Pro Ala Gly Ala
305                 310                 315                 320

Ser Glx Glx
```

(2) INFORMATION FOR SEQ ID NO:11:

(i) SEQUENCE CHARACTERISTICS:
        (A) LENGTH: 289 amino acids
        (B) TYPE: amino acid
        (D) TOPOLOGY: linear (ii) MOLECULE TYPE: peptide (xi) SEQUENCE DESCRIPTION: SEQ ID NO:11:

| Ala | Ala | Pro | Gly | Ser | Ser | Pro | His | Gln | Val | Tyr | Asn | Ile | Thr | Trp | Glu |
|---|---|---|---|---|---|---|---|---|---|---|---|---|---|---|---|
| 1 | | | | 5 | | | | | 10 | | | | | 15 | |

| Val | Thr | Asn | Gly | Asp | Arg | Glu | Thr | Val | Trp | Ala | Ile | Ser | Gly | Asn | His |
|---|---|---|---|---|---|---|---|---|---|---|---|---|---|---|---|
| | | | 20 | | | | | 25 | | | | | 30 | | |

| Pro | Leu | Trp | Thr | Trp | Trp | Pro | Val | Leu | Thr | Pro | Asp | Leu | Cys | Met | Leu |
|---|---|---|---|---|---|---|---|---|---|---|---|---|---|---|---|
| | | | 35 | | | | | 40 | | | | | 45 | | |

| Ala | Leu | Ser | Gly | Pro | Pro | His | Trp | Gly | Leu | Glu | Tyr | Gln | Ala | Pro | Tyr |
|---|---|---|---|---|---|---|---|---|---|---|---|---|---|---|---|
| | 50 | | | | | 55 | | | | | 60 | | | | |

| Ser | Ser | Pro | Pro | Gly | Pro | Pro | Cys | Cys | Ser | Gly | Ser | Ser | Gly | Ser | Ser |
|---|---|---|---|---|---|---|---|---|---|---|---|---|---|---|---|
| 65 | | | | | 70 | | | | | 75 | | | | | 80 |

| Ala | Gly | Cys | Ser | Arg | Asp | Cys | Asp | Glu | Pro | Leu | Thr | Ser | Leu | Thr | Pro |
|---|---|---|---|---|---|---|---|---|---|---|---|---|---|---|---|
| | | | | 85 | | | | | 90 | | | | | 95 | |

| Arg | Cys | Asn | Thr | Ala | Trp | Asn | Arg | Leu | Lys | Leu | Asp | Gln | Val | Thr | His |
|---|---|---|---|---|---|---|---|---|---|---|---|---|---|---|---|
| | | | | 100 | | | | | 105 | | | | | 110 | |

| Lys | Ser | Ser | Glu | Gly | Phe | Tyr | Val | Cys | Pro | Gly | Ser | His | Arg | Pro | Arg |
|---|---|---|---|---|---|---|---|---|---|---|---|---|---|---|---|
| | | 115 | | | | | 120 | | | | | 125 | | | |

| Glu | Ala | Lys | Ser | Cys | Gly | Gly | Pro | Asp | Ser | Phe | Tyr | Cys | Ala | Ser | Trp |
|---|---|---|---|---|---|---|---|---|---|---|---|---|---|---|---|
| | 130 | | | | | 135 | | | | | 140 | | | | |

| Gly | Cys | Glu | Thr | Thr | Gly | Arg | Val | Tyr | Trp | Lys | Pro | Ser | Ser | Ser | Trp |
|---|---|---|---|---|---|---|---|---|---|---|---|---|---|---|---|
| 145 | | | | | 150 | | | | | 155 | | | | | 160 |

| Asp | Tyr | Ile | Thr | Val | Asp | Asn | Asn | Leu | Thr | Thr | Ser | Gln | Ala | Val | Gln |
|---|---|---|---|---|---|---|---|---|---|---|---|---|---|---|---|
| | | | | 165 | | | | | 170 | | | | | 175 | |

| Val | Cys | Lys | Asp | Asn | Lys | Trp | Cys | Asn | Pro | Leu | Ala | Ile | Gln | Phe | Thr |
|---|---|---|---|---|---|---|---|---|---|---|---|---|---|---|---|
| | | | 180 | | | | | 185 | | | | | 190 | | |

| Asn | Ala | Gly | Lys | Gln | Val | Thr | Ser | Trp | Thr | Thr | Gly | His | Tyr | Trp | Gly |
|---|---|---|---|---|---|---|---|---|---|---|---|---|---|---|---|
| | | 195 | | | | | 200 | | | | | 205 | | | |

| Leu | Arg | Leu | Tyr | Val | Ser | Gly | Arg | Asp | Pro | Gly | Leu | Thr | Phe | Gly | Ile |
|---|---|---|---|---|---|---|---|---|---|---|---|---|---|---|---|
| | 210 | | | | | 215 | | | | | 220 | | | | |

| Arg | Leu | Arg | Tyr | Gln | Asn | Leu | Gly | Pro | Arg | Val | Pro | Ile | Gly | Pro | Asn |
|---|---|---|---|---|---|---|---|---|---|---|---|---|---|---|---|
| 225 | | | | | 230 | | | | | 235 | | | | | 240 |

| Pro | Val | Leu | Ala | Asp | Gln | Leu | Ser | Leu | Pro | Arg | Pro | Asn | Pro | Leu | Pro |
|---|---|---|---|---|---|---|---|---|---|---|---|---|---|---|---|
| | | | | 245 | | | | | 250 | | | | | 255 | |

| Lys | Pro | Ala | Lys | Ser | Pro | Pro | Ala | Ser | Asn | Ser | Thr | Pro | Thr | Leu | Ile |
|---|---|---|---|---|---|---|---|---|---|---|---|---|---|---|---|
| | | | 260 | | | | | 265 | | | | | 270 | | |

| Ser | Pro | Ser | Pro | Thr | Pro | Thr | Gln | Pro | Pro | Ala | Gly | Ala | Ser | Glx |
|---|---|---|---|---|---|---|---|---|---|---|---|---|---|---|
| | | 275 | | | | | 280 | | | | | 285 | | |

Glx (2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:12:

TCCTGGCGCC TCTAATTCGA CTCCCACATT    30

(2) INFORMATION FOR SEQ ID NO:13:

(i) SEQUENCE CHARACTERISTICS:

(A) LENGTH: 32 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:13:

TTGCGGCGCC ACGGGAGACA GGTTACTAAA TC                                   32

(2) INFORMATION FOR SEQ ID NO:14:

(i) SEQUENCE CHARACTERISTICS:
          (A) LENGTH: 41 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:14:

ACTGATCGAT TCATTAGGCG CCGGATACCT TTGGACAGGC C                         41

(2) INFORMATION FOR SEQ ID NO:15:

(i) SEQUENCE CHARACTERISTICS:
          (A) LENGTH: 34 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:15:

CATCGCTAGC GTAACGCACA GTTTTAATTG TGGA                                 34

(2) INFORMATION FOR SEQ ID NO:16:

(i) SEQUENCE CHARACTERISTICS:
          (A) LENGTH: 41 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:16:

ACTGATCGAT CTATTAGGCG CCCCCTGTAA TATTTGAACA T                         41

(2) INFORMATION FOR SEQ ID NO:17:

(i) SEQUENCE CHARACTERISTICS:
          (A) LENGTH: 35 base pairs
          (B) TYPE: nucleic acid
          (C) STRANDEDNESS: single
          (D) TOPOLOGY: linear (ii) MOLECULE TYPE: Genomic DNA (xi) SEQUENCE DESCRIPTION: SEQ ID NO:17:

ACTGTCTAGA AAGCGCGCGA ACAGAAGCGA GAAGC                                35

(2) INFORMATION FOR SEQ ID NO:18:

(i) SEQUENCE CHARACTERISTICS:
          (A) LENGTH: 4 amino acids
          (B) TYPE: amino acid
          (D) TOPOLOGY: linear (ii) MOLECULE TYPE: peptide (xi) SEQUENCE DESCRIPTION: SEQ ID NO:18:

Cys Trp Leu Cys
 1

(2) INFORMATION FOR SEQ ID NO:19:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (vii) FEATURE:
        (B) LOCATION: 2...7
        (D) OTHER INFORMATION: where Xaa at positions 1-7 is any
            amino acid (xi) SEQUENCE DESCRIPTION: SEQ ID NO:19:

Cys Xaa Xaa Xaa Xaa Xaa Xaa Cys Cys
 1               5

(2) INFORMATION FOR SEQ ID NO:20:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:20:

Ile Glu Gly Arg
 1

(2) INFORMATION FOR SEQ ID NO:21:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (vii) FEATURE:
        (B) LOCATION: 3...3
        (D) OTHER INFORMATION: where Xaa at position 3 is a
            heterologous sequence (xi) SEQUENCE DESCRIPTION: SEQ ID NO:21:

Ala Ser Xaa Gly Ala
 1               5

(2) INFORMATION FOR SEQ ID NO:22:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (vii) FEATURE:
        (B) LOCATION: 1...16
        (D) OTHER INFORMATION: /note= "An analogous peptide matching
            the consensus sequence for HXB2d V2 domain and homologs
            with an additional C-terminal (Cys) as defined in the
            Los Alamos Human Retrovirus and AIDS database
            (ADP 794.1)."

(xi) SEQUENCE DESCRIPTION: SEQ ID NO:22:

```
Ile Arg Asp Lys Val Gln Lys Glu Tyr Ala Leu Phe Tyr Lys Leu Cys
 1               5                  10                  15
```

(2) INFORMATION FOR SEQ ID NO:23:

(i) SEQUENCE CHARACTERISTICS:
        (A) LENGTH: 33 amino acids
        (B) TYPE: amino acid
        (D) TOPOLOGY: linear (ii) MOLECULE TYPE: peptide (xi) SEQUENCE DESCRIPTION: SEQ ID NO:23:

```
Thr Arg Pro Asn Asn Thr Arg Lys Ser Ile Arg Ile Gln Arg Gly Pro
 1               5                  10                  15
Gly Arg Ala Phe Val Thr Ile Gly Lys Ile Gly Asn Met Arg Gln Ala
             20                  25                  30
His
```

(2) INFORMATION FOR SEQ ID NO:24:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (xi) SEQUENCE DESCRIPTION: SEQ ID NO:24:

```
Arg Lys Arg Ile His Ile Gly Pro Gly Arg Ala Phe Tyr Thr Thr Lys
 1               5                  10                  15
Asn
```

(2) INFORMATION FOR SEQ ID NO:25:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:25:

```
Leu Val Pro Arg Gly Ser
 1               5
```

FUSION GLYCOPROTEINS

This is a divisional of application Ser. No. 08/110,300 filed on Aug. 20, 1993 now U.S. Pat. No. 5,643,756, which is a continuation in part of Ser. No. 07/938,100, filed Aug. 28, 1992 now abandoned.

BACKGROUND OF THE INVENTION

It has been shown for retroviral, influenza, and herpes viral glycoproteins that removal of N-linked glycans dramatically reduces immune reactivity (Alexander and Elder, 1984, Science, 226:1328–1330; Sjobloom et al., 1987, J. Gen. Virol. 68:549–554; Olofsson et al., 1990, J. Virol. 71:889–895). Considerable evidence has also accumulated suggesting that N-linked glycosylation is necessary for proper immunoreactivity or immunogenicity of human immuno-deficiency virus (HIV) gp120. For example, an extensive study comparing the immunogenicity of native glycosylated gp120 to that of env 2–3, a nonglycosylated form of the protein produced in yeast, was performed in baboons (Haigwood et al, 1992, J. Virol. 66:172–182). In this study, glycosylated gp120 induced high titers of neutralizing antibodies against the homologous and related viruses, and weak neutralizing titers against more distant viruses, while the nonglycosylated protein yielded only low neutralizing titers directed solely against the homologous virus. In addition, whereas the glycosylated protein was able to bind to CD4, the nonglycosylated protein was not. Other studies have shown that removal of N-linked glycans from native or recombinant gp120 reduces or abolishes binding activity of gp120 to CD4 and diminishes infectivity of HIV-1 (Matthews et al, 1987, PNAS 84:5424–5428; Fenouillet et al, 1989, J. Exp. Med. 169:807–821; Fenouillet et al, 1990, J. Virol. 64:2841–2848). Recent data show that removal of specific carbohydrates from recombinant gp160 reduced both its immunoreactivity with hyperimmune antisera and its immunogenicity in rabbits (Benjouad et al, 1992, J. Virol. 66:2473–2483). Finally, the epitopes of strongly neutralizing MAbs that have been isolated are destroyed by removal of N-linked glycans from the viral proteins (Fung et al, 1992, J. Virol. 66:848–856). These results demonstrate an important role for N-linked glycans in gp120 immunoreactivity and immunogenicity. These glycans may be acting either indirectly, by achieving the correct conformation of gp120, or directly by determining the formation of immunoreactive or immunogenic sites.

A major difficulty in the production of isolated gp120 domains is the fact that all of these domains are highly glycosylated. Considerable evidence suggests that glycans are needed either to achieve correct conformations or for the formation of the epitopes themselves.

The invention described here is intended to address this problem, but can also be used for the expression of non-gp120 glycopeptides whose immunogenicities or biological activities are dependent on correct glycosylation or conformation.

SUMMARY OF THE INVENTION

The present invention relates to vectors for expressing a glycosylated protein in cells, wherein the vector is adapted to express a fusion glycoprotein. The fusion glycoprotein contains an N-terminal fragment of env surface protein of a retrovirus, the surface protein containing a hydrophobic glycosylation signal located about seven residues N-terminal to a Cys-trp-leu-cys sequence (SEQ ID NO:18) located approximately centrally in the surface protein. The N-terminal fragment includes the N-terminal globular domain of the env surface protein. A selected glycopeptide is fused to the C-terminus of that N-terminal fragment. The selected glycopeptide preferably includes a domain that is glycosylation dependent, a domain that is conformationally dependent, or both. The domain may contain, for example, an immunoreactive or immunogenic epitope, or have another biological activity, such as receptor binding or hormone binding activity.

Also included in the invention are plasmids that encode the above vectors. These plasmids can be used to engineer and express the vectors.

Mammalian cell cultures that produce the novel fusion glycoproteins, the novel fusion glycoproteins, and viral particles incorporating those glycoproteins in their envelope moieties are also included in the invention.

BRIEF DESCRIPTION OF THE DRAWINGS

FIG. 1 shows the DNA and amino acid sequence (SEQ ID NO:8) of the FB29 isolate of Friend ecotropic MuLV.

FIG. 2 shows a restriction map of a FB29/clone 57 hybrid.

FIGS. 3A—F shows the DNA sequence (SEQ ID NO:9) of pLRB332. MuLV sequences (non-coding strand) are shown in upper case; non-MuLV sequences are shown in lower case. The NheI site and stop codons at 864, the first codon of gp70 at 1719, and the env initiation codon at 1821, are underlined.

FIGS. 3G—H shows the amino acid sequence (SEQ ID NO:10–11) of amino acid 1-285 truncation fragment of gp70 expressed by pLRB332. The terminal ASZZ is the amino acid sequence encoded by the NheI site and two stop codons. The top sequence (SEQ ID NO:10) includes the signal peptide, and the bottom sequence (SEQ ID NO:11) does not.

FIG. 4A shows a restriction map of the MuLV regions of pLRB332.

FIG. 4B shows a diagram of truncation and insertion fusion glycoproteins described in the examples.

FIG. 5 shows autoradiograms of an SDS-PAGE analysis of immunoprecipitated gp(1-263) and gp(1-285) truncation glycoproteins described in the Examples.

FIG. 6A shows the disulfide bonded structure of gp(1-263) V1/V2 fusion glycoprotein described in the Examples.

FIG. 6B shows an autoradiogram of an SDS PAGE analysis of immunoprecipitated gp(1-263) V1/V2 fusion glycoprotein described in the Examples.

FIG. 7 shows an autoradiogram of an SDS PAGE analysis of immunoprecipitated gp(1-263) V1/V2 fusion glycoprotein described in the Examples.

FIG. 8 shows an autoradiogram of an SDS PAGE analysis of immunoprecipitated gp(1-263) V1/V2 fusion glycoprotein described in the Examples.

FIG. 9 shows an autoradiogram of an SDS PAGE analysis of immunoprecipitated glycosylation site mutant gp(1-263) V1/V2 fusion glycoprotein described in the Examples.

FIG. 10A shows the disulfide bonded structure of gp(1-263) V3 fusion glycoprotein described in the Examples.

FIG. 10B shows autoradiogram of an SDS PAGE analysis of immunoprecipitated gp(1-263) V3 fusion glycoprotein described in the Examples.

DETAILED DESCRIPTION OF THE INVENTION

The env-based expression system of this invention allows glycopeptides and viral particles incorporating those glycopeptides to be made by mammalian cells in an efficient manner. We have determined that expressed glycopeptides retain glycosylation dependent (such as N-glycan dependent) and conformationally dependent structures. Such expression is particularly important for viral glycopeptides to make them useful for immunoreactive purposes, such as immunoassays or affinity purifications, or for immunogenic purposes, such as the production of monoclonal antibodies or for inducing protective immunity.

It will normally be most desirable to use the invention to express a glycopeptide that corresponds to (i.e., has an amino acid sequence that is the same as, or is derived from, the sequence of) a naturally occurring glycopeptide. We have found that the env expression system of the invention is useful, for example, in efficiently expressing N-glycan dependent epitopes contained in the V2 region of HIV-1 gp120. As described in U.S. application Ser. No. 07/860,889, incorporated by reference herein, the V2 region is recognized by a powerfully neutralizing antibody against an N-glycan dependent epitope. In particular, the antibodies are capable of neutralizing HIV-1 infection at a concentration lower than that of previously described neutralizing antibodies. An example of such an antibody, a monoclonal antibody derived from peripheral mononuclear B-cells of an HIV-immunized chimpanzee, is produced by EBV transformed chimp peripheral blood mononuclear cells deposited at the ATCC, Parklawn Drive, Rockville, Md. on Mar. 10, 1992, and accorded accession no. CRL 10983. New glycopeptides that include the V2 region of gp120 are made according to the invention. They contain an N-glycan-dependent epitope that is reactive with antibodies against N-glycan dependent epitopes of native gp120 but do not contain the immunodominant V3 region. Thus they are especially useful to induce (or measure in an immunoassay) a specific anti-V2 response. Such immunoreactive V2 glycopeptides have not been expressed by others.

The vector of the invention is advantageously used to efficiently express complex conformational epitopes, i.e., those involving several disulfide bonds. For example, we have correctly expressed the V1/V2 region of gp120, perhaps the most complicated portion of that molecule, which in addition to six glycosylation sites, includes six cysteines, all of which are believed to be involved in specific disulfide bonds (Leonard et al., 1990, J. Biol. Chem. 265:10373–10382). The V1/V2 region expressed using the vector has the capability of reacting with antibodies against N-glycosylation dependent epitopes (as described above) and/or with antibodies against conformational epitopes of that region.

This invention allows for the expression of fragments of glycoproteins, or glycopeptides, in such a way as to maximize their synthesis, glycosylation, folding, stability, and secretion. Expression of the fusion glycoprotein on the surface of cells or virus particles is also accomplished. The invention can also provide a "tag" for the detection and purification of glycopeptides that is independent of their own properties. The expression system can also advantageously be used to express glycopeptides in immunogenic form, for example fused to the N-terminal carrier portion of the env surface protein. Thus, the vectors are particularly useful in the expression of glycopeptides containing glycan-dependent or conformationally dependent epitopes, fused to the N-terminal surface protein fragment. If desired, the vector may be used to express a fusion protein as a secreted molecule. Alternatively, sequences can be included in the vector that code for the remaining C-terminal part of the env gene. We have determined that fusion proteins can then be functionally expressed in the envelope of infectious or non-infectious particles of the particular retroviral env used in this invention. In this application, "truncation chimeric (or fusion) glycoprotein" is used to refer to those glycoproteins that are expressed by vectors which do not include sequences coding for the remaining env glycoprotein (in particular the C-terminal globular domain of these env surface protein and the trans-membrane protein). The term "insertion chimeric (or fusion) glycoprotein" is used wherein foreign protein fragments are inserted into the region of the surface protein of these particular env types that links the N-terminal and C-terminal globular domains without loss of sequences of either globular domain, and including the transmembrane protein.

The N-terminal fragment of the surface protein used is a carrier for the glycopeptide or glycoprotein that is to be expressed. Retroviral env is normally expressed as a membrane-associated precursor protein which is processed during transport through the ER (endoplasmic reticulum) and Golgi system by proteolytic cleavage and glycan maturation to form a complex consisting of SU (surface protein), disulfide-linked to the TM (transmembrane) protein. For example, MuLV (surface protein) gp70 is a soluble glycoprotein containing several domains, and is linked to transmembrane protein p15E. (Although the molecular weights vary somewhat, the term "gp70" is used herein to refer to the surface protein of all MuLV virus strains, as well as the highly similar surface protein of the FeLV (Feline Leukemia virus) strains.) The receptor binding domain of gp70 is comprised of the N-terminal region, which is believed to be a structurally independent globular region. This domain contains at least two N-linked glycans. The secondary structure of an ecotropic gp70 has recently been determined, and shows that the twelve cysteines in this region are joined in six internal disulfide bonds. The C-terminal domain of MuLV surface protein is also a globular region that contains 4–5 N-linked glycans and includes the disulfide linkage to p15E.

To make a vector for expressing fusion glycoprotein, a recombinant gene is constructed in which the coding sequence for a selected glycopeptide is fused in frame to the C-terminus of a truncation fragment of the retroviral env surface protein. This fragment codes for the N-terminal domain of the protein that is glycosylated normally and folds into a globular structure. In one embodiment of the invention, the globular structure includes the receptor binding domain of the surface protein, i.e., the domain that binds to its cell surface receptor. In another embodiment of the invention, the globular domain includes the first twelve cysteines of gp70, which are all believed to be involved in intra-domain disulfide bonding.

In a preferred embodiment, the truncation (or insertion) site is selected to be in a region of env surface protein that is believed to be in an extended conformation and to function as a linker between the two globular domains of the surface protein. This region is known to be immunogenic in the FeLV and MuLV viruses. For example, in Friend clone 57 of MuLV, this linker region of gp70 is believed to maximally extend from the Cys-free sequence from residue 185 up to but not including the conserved N-glycan attachment site at residue 302. In other surface proteins, the linker is believed to maximally include the entire cysteine free sequence immediately N-terminal to the conserved N-linked glycosylation site homologous to the conserved N-linked glycosylation site at residue 302 of Friend clone 57 gp70.

In another preferred embodiment of the invention, sequences coding for the C-terminal domain of the surface protein and for the trans-membrane domain of the env precursor glycoprotein are added at the C-terminus of the fusion protein. These additional sequence can generate membrane bound fusion proteins that are efficiently expressed at the cell surface and on virus particles. The additional sequences can allow expression of the fusion glycoprotein from infectious virus. Coexpression of at least the gag gene from any vector allows incorporation into retroviral particles. This can be advantageous, because, for example, particulate immunogens are believed to generally be more immunogenic than their soluble counterparts.

A particular class of retroviral env proteins that share a specific sequence motif defines those env proteins that are used in the fusion glycoproteins, and coded for by the vectors, of this invention. In particular, the retroviral env proteins are defined by the presence of a hydrophobic glycosylation signal located about seven residues N-terminal to a Cys-trp-leu-cys sequence (SEQ ID NO:18) located centrally in the SU domain of the env polyprotein. This glycosylation signal and sequence have been described by Kayman et al., 1991, J. Virol. 65:5323. These sequences are invariably associated with the presence of a Cys-x-x-x-x-x-x-cys-cys sequence (SEQ ID NO:19) within the ectodomain of the transmembrane protein. Preferred are those env proteins of this type that also display an extensive Cys-free region N-terminal to the hydrophobic glycosylation signal. This cys-free region preferably is at least 40 amino acids long. These include env proteins of the REV-A avian virus (Wilhelmsen, Eggleton and Temin 1984 J. Virol. 52:172–182) and Mason-Pfizer Monkey Virus (Sonigo et al.1986 Cell 45:375–385). More preferred are those in which this Cys-free region is Pro-rich, i.e., contains several Pro residues. This includes the SU of Gibbon Ape Leukemia Virus (Delassus, Sonigo and Wain-Hobson 1989 Virol. 173:205–213). Most preferred for use in this invention are the env genes of MuLV and of Feline Leukemia Virus (e.g. Donahue et al.1988 J. Virol. 62:722–731), which have a very high degree of sequence similarity to each other and also share the above mentioned defining characteristics. These surface proteins have N-terminal and C-terminal globular domains joined by a linker region into which the selected peptide is placed to form a truncation or an insertion glycoprotein.

The sequences encoding the fusion glycoprotein (whether as a secretable separate moiety, an internal protein, a cell surface protein, or associated with retroviral particles) can be expressed using conventional vectors for expression of proteins in mammalian cells. Retroviral expression vectors can be used, such as those developed from Rous sarcoma virus (Sorge et al., 1982, J. Mol. Appl. Gen., 1:547), murine mammary tumor virus (Gunzberg et al., 1986, Virology, 155:236) and murine leukemia virus (MuLV), such as the Moloney MuLV (McLachlin et al., 1990, in Progress in Nucleic Acid Research and Molecular Biology, 38:91) or the Friend MuLV. Secreted fusion glycoproteins or glycoproteins associated with viral particles are produced from a preferred retroviral vector described below. The preferred vector allows easy and rapid manipulation of new constructs, and high level expression.

Alternatively, conventional non-retroviral viral vectors can be conventionally constructed to express the fusion glycoproteins of the invention, including vaccinia (for example, see Vijaya et al., 1988, Vaccines 88, CSH pp.211–214) and herpes virus (for example, see Kit et al., 1991, Vaccine 9:564–572).

In addition to viral vectors, conventional plasmid vector expression systems that do not employ viral particle intermediates can be employed to express the fusion glycoproteins of the invention in mammalian cells. These systems are either transient expression systems (i.e., those that result in death of the mammalian cells producing the expressed product) or those that allow stable producing mammalian cell lines to be established (i.e., do not result in death of the cells).

The systems described above are known in the art and are made using well-established techniques. Conventional cloning vehicles are used to make plasmids encoding the desired vectors using techniques such as described in *Current Protocols in Molecular Biology* (Ausubel et al.eds, John Wiley and Sons, New York, N.Y.) and *Molecular Cloning: A Laboratory Manual* (Sambrook et al. eds, Second Edition, 1989, Cold Spring Harbor Laboratory Press, Cold Spring Harbor, N.Y.). Conventional cell lines, such as mammalian insect, yeast and other glycosylating cell lines, are transformed, transfected, or infected, to generate the fusion glycoproteins of the invention. Cells are also transformed, transfected, or infected in vivo to generate the fusion glycoproteins.

The vectors used in any of these systems for expressing the fusion glycoprotein, i.e. that include a sequence coding for the fusion glycoprotein of the invention operably linked to a promotor, are included in the invention.

The invention also includes the process of infecting mammalian cells with viral vectors, or transfecting the cells with plasmid vectors, of the invention. Mammalian cell lines may be infected when it is desired to purify the fusion glycoprotein for use in an immunoreactive or immunogenic composition. Producer cell lines are made to express secreted fusion glycoprotein or fusion glycoproteins associated with viral particles. It may be preferable to express the fusion glycoprotein in viral particles rather than in soluble form to make recovery easier. Also, infectious or noninfectious particles incorporating the desired glycoprotein in their envelope can be obtained in this manner for immunizing mammals.

Alternately, the vectors can be used to infect or transfect mammalian or other glycosylating cells in vivo in order to cause expression of the soluble glycoprotein, or glycoprotein expressed on the cell surface, or associated with viral particles.

Fusion glycoproteins can be conventionally purified from lysates or supernatants of producing mammalian cell cultures. Soluble glycoproteins are advantageously purified using monoclonal or polyclonal antibodies against the surface protein. If desired, the selected glycopeptide can be cleaved from the env fragment by including a conventional cleavable linker between the N-terminal globular domain and the inserted glycopeptide. If the selected glycopeptide is recovered on a retroviral particle, a cleavable linker can also be included between the selected glycopeptide and the C-terminal env region. The term "fusion glycoprotein," as used herein, refers to products wherein the env sequence is directly fused to the selected glycopeptide as well as wherein there is an additional sequence or sequences in the fusion product. The product may contain the cleavable linker referred to above, and/or other sequences.

For example, a cleavage site for a specific protease could be inserted between the surface protein fragment(s) and the selected glycopeptide in order to allow eventual release of the selected glycopeptide from the env sequence. Incorporation of an Ile-glu-gly-arg sequence (SEQ ID NO:20) allows specific cleavage with blood coagulation factor Xa and has been used successfully to separate (i.e., cleave)

domains of interest from carrier domains in recombinant fusion proteins (Nagai and Thogersen, 1987, Meth. Enzym. 153:461–481).

Also a non-immunological affinity tag can be included at the N-terminus of the surface protein fragment. For example, addition of a sequence of six histidine residues allows rapid purification on an $Ni^{2+}$-nitrilotriacetic affinity column under native conditions using imidazole buffers (Janknecht et al., 1991, PNAS 88:8972–8976 and Examples below).

T-helper epitopes from the source of the heterologous gene fragment being expressed can also be inserted into the fusion gene at the N-terminus, the C-terminus, or elsewhere, to enhance the immunogenicity of the fusion protein and the probability of a rapid and intense immune response of animals immunized with fusion glycoprotein, following exposure to the pathogen. For purposes of HIV-1 glycopeptide expression, a number of T-helper epitopes with broad MHC reactivity have been characterized, such as amino acids 791–823 from the C-terminus of gp41 or amino acids 391–414 from the C4 region of gp120 (Berzofsky et al, 1991, J. Clin. Invest. 88:876–884).

For expressing certain HIV sequences in fusion glycoproteins of this invention, it may be necessary to include RRE (rev responsive element) sequences in the vector such that they will be retained in the mRNA encoding the fusion glycoprotein and to provide rev activity in cells expressing the fusion glycoprotein. These elements are not required for expressing the V1/V2, V3, or V4/C4 fusion glycoproteins described herein.

It is also possible to express multiple selected glycopeptides in a single fusion glycoprotein. This can be done with either truncation or insertion glycoproteins. For example, the selected glycopeptides can be different fragments of a single protein, fragments from different proteins, or homologous fragments from different alleles of the same protein (e.g. the V1/V2 domain of gp120 from the HXB2d and MN isolates of HIV-1), or any combination of such fragments. The multiple inserts can be placed at different locations within the interdomain linker of an SU. Alternatively, multiple selected glycopeptides can be inserted in concatenated arrays at a single site in the SU. Such inserted multiple glycopeptides can be separated from each other by a spacer peptide.

The N-terminal fragment of the env glycoprotein preferably forms a receptor binding domain, as it is believed that proper autonomous folding and glycosylation of that region during expression may aid independent proper folding and glycosylation of the selected glycopeptide. It may also aid in efficient secretion of the fusion glycoprotein. Examples of such env fragments are amino acids 1–263 and 1–285 of Friend ecotropic clone 57 gp70. An env fragment containing amino acids 1–227 is also described below. These gp70 fragments terminate in or near a proline-rich region that is believed to form an extended linker between N-terminal and C-terminal globular domains of gp70 and is known to be an immunogenic region of gp70. The region carries epitopes recognized by polyclonal hyperimmune sera and monoclonal antibodies. The gp70 domain can therefore serve as a tag for the identification and purification of the fusion glycoprotein. Truncation at amino acid 227 removes the entire proline-rich linker region and some of the previously assigned N-terminal domain but retains all of the N-terminal Cys residues and results in a fragment that possesses receptor-binding activity. Truncation at amino acid 263 retains a large fraction of the proline-rich linker but eliminates the section of this linker region that is known to carry O-linked glycans in gp70 as well as the third N-linked glycan of Friend MuLV gp70. The resultant protein fragment is efficiently expressed and secreted more rapidly than the 227 amino acid fragment. Truncation at amino acid 285 retains the entire proline-rich linker region, including the O-linked glycosylation sites and the additional N-linked glycosylation site, and the resultant fragment is also efficiently expressed and secreted. The optimal truncation site in gp70 may depend on the particular glycopeptide being expressed.

The expression vector of the invention should encode a signal sequence 5' to the surface protein sequence. In the examples below, the native env signal sequence is encoded in the vectors but other signal sequences can be substituted.

It has been determined that if the C-terminal portion of the env gene sequence is also incorporated in the vectors, i.e., where a foreign sequence is inserted into the surface protein between the N-terminal globular domain and the C-terminal domain, many resulting hybrid env proteins are processed, incorporated into cellular membranes and viral particles, and retain the ability to mediate virus infection. Foreign sequences are exposed on intact virions in an area that is highly immunogenic. Inserted sequences can be used to obtain an infectious particle, a non-infectious particle, or an env protein that is processed and expressed at the cell surface, but not incorporated into virus particle.

The processing of a retroviral env product begin with the folding of the glycosylated precursor protein in the endoplasmic reticulum and culminate with the mature SU and TM proteins on the surface of the virus particle. Those proteins mediate binding to the host cell and effect membrane fusion between the viral and host cell membranes, delivering the viral core into the cytoplasm. Insertion chimeric glycoproteins such as those described in the examples below are able to act as SU for infectious virus. Such fully functional chimeric glycoproteins are believed to be more versatile than non-functional glycoproteins. Particular insertion chimeric glycoproteins may be blocked at different stages of this processing or blocked in one or more functions. However, insertion chimeric glycoproteins that do not retain full function are also useful.

An insertion chimeric glycoprotein that is synthesized but that does not fold properly into a compact globular structure with native env disulfide bonds would be expected to be retained in the endoplasmic reticulum until it was degraded intracellularly. Such an insertion chimeric glycoprotein might not be useful for production of purified glycopeptides or as an immunogen for induction of humoral responses, but would likely be most useful for induction of MHC class I-mediated cellular immune responses. For example, it may be desirable to avoid competition between induction of humoral and cellular immune response, as has been suggested for tuberculosis and AIDS. In this case, use of expression vectors encoding insertion chimeric glycoproteins that do not fold and are not transported out of the endoplasmic reticulum would be particularly appropriate. Vectors encoding insertion chimeric glycoproteins that are processed from the endoplasmic reticulum to the Golgi apparatus but do not continue to the cell surface would be useful in the same ways.

Insertion chimeric glycoproteins that are processed to the cell surface are capable of eliciting humoral responses as well as cellular responses. An insertion chimeric glycoprotein that is destabilized in its interaction with the transmembrane protein is rapidly released from the cell surface (i.e. it is functionally similar to a secreted protein). An insertion chimeric glycoprotein that interacts normally with the transmembrane protein is likely to be present at significant levels on the cell surface. An insertion chimeric glycoprotein that is present on the cell surface would normally be more immunogenic than one that is rapidly released.

Insertion chimeric glycoproteins that are incorporated into viral particles present the selected glycopeptide on a multivalent particulate immunogen. This is a particularly potent method of antigen presentation. It also allows for particle based purification methods for the insertion chimeric glycoprotein and the selected glycopeptide. Such insertion chimeric glycoproteins do not need to be capable of mediating viral infection.

To obtain expression of chimeric glycoproteins that cannot mediate viral infection, pseudotyped retroviral vectors, other viral vectors (see above) or direct DNA transfection can be used. Any insertion chimeric glycoprotein that is processed to the cell surface can be obtained as a purified protein, and used for its desired purpose, e.g., whether used for binding to a receptor, for immunoreacting, or for inducing an immune response. Non-functional insertion chimeric glycoproteins that are incorporated into viral particles can also be used as inactivated particles for the desired purpose.

The fully functional insertion chimeric glycoprotein can be encoded in an infectious retroviral vector, i.e., a retrovirus that causes a spreading infection of retrovirus expressing the insertion glycoprotein. In the appropriate host such a retrovirus establishes viremia in the infected animal, thereby exposing the animal to an increasing dose of the selected glycopeptide of the insertion glycoprotein for an extended time. Infectious retrovirus incorporating the insertion glycoprotein in its envelope can also be expressed in a species that the virus cannot infect. For example, human cells can be transformed or transfected with a vector for expressing infectious ecotropic MuLV that contains the insertion glycoprotein in its envelope. Since ecotropic viruses do not infect humans, this method is equivalent to using a defective virus. In that case, particle associated, cell surface, and soluble forms of the insertion glycoprotein are presented for (if immunogenicity is desired) induction of humoral responses, and intracellular expression for cellular immune response. Alternatively, deletion of substantial parts of the pol gene from the expression vector genome leads to the expression of non-infectious virus particles bearing the insertion glycoprotein, regardless of host. In addition, incorporating the recombinant env gene into the expression vector genome in the absence of the gag gene allows processing to the cell surface, but not particle formation. Also, expressing the surface protein domain of the chimeric env without the transmembrane domain produces a secreted insertion chimeric glycoprotein.

Chimeric surface proteins that function in virus replication can be used to generate hyperimmune sera and MAbs using live virus instead of adjuvants. Chimeric surface proteins that are incorporated into virus particles but are defective for viral replication can also be used. The inoculated animal is exposed to a multivalent, particulate immunogen rather than a soluble protein, which is potent way of presenting many antigens. Preparation of virus for inoculating animals such as mice and rats to prepare MAbs is extremely easy and inexpensive compared with use of purified proteins. Non-infectious, pseudotyped virus particles can be used in any animals, including humans, and are inexpensive and easy to produce. MuLVs, in particular, have a wide host range that allows use of live virus inoculations in a wide range of mammals. Examples described below utilize an ecotropic SU, which allows infection of rats and mice. Use of amphotropic SUs allows retroviral infection of other mammals as well, including humans. Dualtropic and xenotropic SUs allow infection of certain mammals as well. These SUs are well characterized and known to those skilled in the art.

Where fusion glycoproteins are incorporated into viral particles, the size of the particle can be used as a basis for the purification of the fusion glycoprotein and the selected glycopeptide. Because of this particle association, separation from almost all other proteins found in cell supernatants is easily accomplished by ultracentrifugation of the particles.

An inserted protein that is expressed in infectious or non-infectious particles can be used in inactivated particle compositions used, for example, for immunogenic purposes. The infectious or non-infectious particles can also be expressed by inoculating with retrovirus vectors, or with other vectors such as those mentioned above. In the case of immunogenic compositions, preparation of live virus is easier and less expensive than preparation of subunit compositions. Inactivated virus particles are also relatively inexpensive and easy to produce, and often highly immunogenic. It is also possible to purify viral particles of the invention to a higher yield and purity than certain viruses from which the inserted glycoprotein can be derived, e.g., HIV. With respect to HIV, this is due in part to the fact that the surface protein in the present invention is covalently linked to the transmembrane protein whereas in HIV that linkage is non-covalent. Also, nonhazardous particles can be obtained using the invention, whereas HIV is highly pathogenic and therefore difficult to obtain in large quantities. Also, by using multiple allelic antigenic sequences of a virus from which the inserted polypeptide is derived, a broader (i.e., less type-specific) anti-virus response might be induced than by using the virus itself as an immunogen.

DNA compositions such as plasmid DNA vectors can also be used for inoculation. An example of such a vector is described below. Retroviral vectors can also be used in DNA compositions as well as in viral particles.

Expression of the chimeric env gene without the gag gene would produce proteins expressed on the cell surface. The gag gene can be co-expressed with the chimeric env gene in the absence of a functional pol gene to produce defective retroviral particles which present the chimeric retroviral particles on their surface. Such use retains the advantage of cell surface and/or particle presentation of humoral response epitopes and presentation of cellular response epitopes while avoiding potential risks of live retrovirus infection.

The expression vector of the invention can be created from available materials using a shuttle vector for manipulating constructs in, e.g., E. coli. Assembly of expression vectors is described in detail in the Examples below. Alternatively, expression vector pLRB332, described in the Examples, can be obtained and is adapted for insertion of a sequence encoding a selected glycopeptide to make an expression vector encoding a fusion product.

Vectors described in the Examples below have a number of advantages:
1) All DNA construction steps can be carried out in bacteria. If desired, resulting plasmids can be used directly to construct mammalian cell lines expressing a recombinant fusion glycoprotein without the need to generate recombinant viruses within infected cells, as is required for other common systems such as vaccinia virus, herpes virus, and baculovirus. This allows large numbers of constructs to be prepared and analyzed quickly and efficiently.

2) The vector system is non-lytic and thus generates stable cell lines, so that continuously producing cultures can be isolated and used to produce fusion glycoproteins.

3) Cultures in which essentially all cells are expressing the recombinant protein can be prepared quickly, without using selectable markers, by using retroviral vector packaging cell lines.

4) The constructs can be easily expressed in a wide variety of cells, including those of human origin, using amphotropic pseudotypes of the MuLV vector, or by constructing the chimeras in an amphotropic surface protein.

5) The level of expressed protein in mammalian cell culture is quite high, allowing analyses to be carried out easily and quickly during the experimental stages of vaccine development, as shown in the Examples below.

The MuLV vector embodiment of the invention can be manufactured in packaging cell lines such as those that are described in the Examples or any other suitable lines. Such cell lines are well known and available. The producer cell line used, i.e., that which is infected and produces the fusion glycoprotein, can be a conventional mammalian cell line that can be infected with either ecotropic or amphotropic MuLVs. Ecotropic retroviruses infect and replicate only in mouse and rat cells. Amphotropic retroviruses infect mouse as well as other mammalian species. The MuLV virus can also be used to infect mammals to cause in vivo expression of the fusion glycoprotein.

As noted above, the purified products of the expression system can be used as immunogens, either for production of monoclonal or polyclonal antibodies or induction of protective immunity. The products can be mixed with appropriate adjuvants in order to enhance immune response. If the selected glycopeptide is cleaved from the carrier (or the entire envelope, where expressed in particle form), it can be chemically joined to a conventional carrier, such as bovine serum albumen. The fusion glycoprotein, however, when used separately from virus particle as an immunogen, preferably has a molecular weight greater than 20,000 daltons, so that it is likely to be immunogenic by itself Immunogenic compositions can be administered intradermally or subcutaneously or orally. For a vaccine, several inoculations are preferably administered, with follow-up booster administrations.

Conventional assays can be performed with products made using the invention to detect antibodies, receptors, or other binding partners for the expressed glycopeptide. Truncation and insertion chimeric glycoproteins, as well as glycopeptides cleaved from these glycoproteins, are used in these methods. Lower levels of mature insertion chimeric glycoprotein are obtained as compared with truncation chimeric glycoprotein; thus it may be preferable to use the truncation chimeric glycoprotein. A selected insertion chimeric glycoprotein, however, may present epitopes not presented by the corresponding truncation chimeric glycoprotein. The ability to use particle association as the basis for insertion chimeric glycoprotein purification can also make these preferable to truncation glycoproteins. If desired, the insertion chimeric glycoproteins can be separated from the particle and the other viral proteins.

An immunoassay such as an ELISA might employ a soluble fusion product including, for example, the V1/V2 glycopeptide, and also include means for the detection of an immune complex formed between anti-HIV antibody and the fusion product. For example, a "sandwich" might be formed using a solid phase coated with HIV-1 lysate, anti-HIV antibody, and the fusion product, followed by detection of the "sandwich" by a labelled anti-gp70 antibody. Alternatively, a solid phase might be coated with the fusion glycoprotein (or glycopeptide cleaved from the glycoprotein), the solid phase exposed to sera containing anti-HIV antibody, and the presence of the anti-V1/V2 antibody detected with a subsequent labelled anti-human antibody. In another method, radiolabelled fusion glycoprotein is used as a substrate for immunoprecipitation, followed by separation of proteins according to molecular mass on SDS polyacrylamide gels and detection by exposure to photographic film. This is a sensitive method, but it is more labor intensive than ELISA methods. Fusion glycoproteins can also be used in Western Blot methods. Alternatively, a receptor ligand expressed according to the invention can be used in a assay for the receptor. Other diagnostic uses for various expressed glycoproteins made using the invention will be apparent to one skilled in the art.

As noted above, the expression vector is preferably used to express short glycopeptides, for example, less than 150 amino acids, most preferably shorter than 100 amino acids. Often the glycopeptide expressed will be greater than 20 amino acids, embodiments of the examples being greater than 40 amino acids. The invention, however, may also be used for expressing larger fragments or even complete glycoproteins.

Fragments of any of the glycopeptides described herein can also be advantageously expressed as fusion products of the invention.

The invention is further illustrated by the following examples.

EXAMPLES
CONSTRUCTION OF GLYCOPEPTIDE EXPRESSION FUSION VECTORS

Standard recombinant DNA techniques are used throughout, as can be found in manuals such as *Current Protocols in Molecular Biology* (Ausubel et al.eds, John Wiley and Sons, New York, N.Y.) and *Molecular Cloning: A Laboratory Manual* (Sambrook et al. eds, Second Edition, 1989, Cold Spring Harbor Laboratory Press, Cold Spring Harbor, N.Y.). All relevant work was done using the *E. coli* Strain DH5Alpha (BRL) [Bethesda Research Labs] and the Hanahan (Hanahan, 1983, J. Mol. Biol. 166:557–580) method was used for transformation. Enzymes were from Boehringer-Mannheim and New England Biolabs and were used as recommended by the manufacturers; agarose was from BRL and FMC Bioproducts. All references cited either in the Examples section or in the rest of this application are hereby incorporated by reference.

The MuLV retroviral vector described below has a typical retroviral vector structure, except that gap and pol expression have not been eliminated. Not eliminating gag and pol expression may be desirable for some purposes. The vector uses the natural splice donor and acceptor sequences involved in normal expression of MuLV env in the expression of the fusion glycoprotein.

A one LTR clone of the FB29 isolate of Friend ecotropic MuLV permuted at the unique HindIII site (5060) (Sitbon et al. Cell 47:851, 1986) was used to make a MuLV expression vector. The sequence of this isolate is shown as FIG. 1 (SEQ ID NO:8). Restriction site numbering below refers to the first base of the enzyme recognition site in this FB29 sequence, which begins at the 5' end of the genomic RNA. The entire envelope gene sequence and a portion of the pol gene and the 3' LTR from the clone 57 Friend ecotropic MuLV (Oliff et al. J. Virol. 33:475, 1980; complete sequence shown in Koch, Nunsmann and Friedrich, 1983, J. Virol. 45:1–9) were substituted for those of the FB29 isolate using the shared, unique restriction sites SphI (5135) and EspI (7863), resulting in an FB29/clone 57 hybrid permuted viral genome. A collinear, two LTR clone was constructed from this isolate as follows.

The unique PvuII site in pSP72 (Promega), a high copy number E. coli vector, was converted to an NheI site by insertion of an 8-basepair linker (GGCTAGCC). The EspI (7863) to HindIII (5060) fragment carrying the LTR and the gag gene and part of the pol gene from the FB29 permuted clone was then inserted into HindIII/EcoRV cut plasmid, following E. coli DNA polymerase Klenow fragment-filling of the EspI overhang. Then the HindIII (5060) to SpeI (280) (SpeI generates NheI compatible overhangs) fragment from the permuted FB29/clone 57 hybrid clone carrying the rest of the pol gene and the envelope gene and the LTR was inserted into NheI/HindIII cut plasmid. This resulted in a hybrid colinear viral genome, with the 5' LTR beginning at the (destroyed) EspI site and the 3' LTR terminating at the (destroyed) SpeI site, in which all sequences derive from the FB29 clone except those between the SphI and EspI sites. The total plasmid, pLRB303, is 11.32 kb, with unique viral sequences of 8.93 kb (a restriction map of the MuLV sequences is shown in FIG. 2).

Figure 4A:
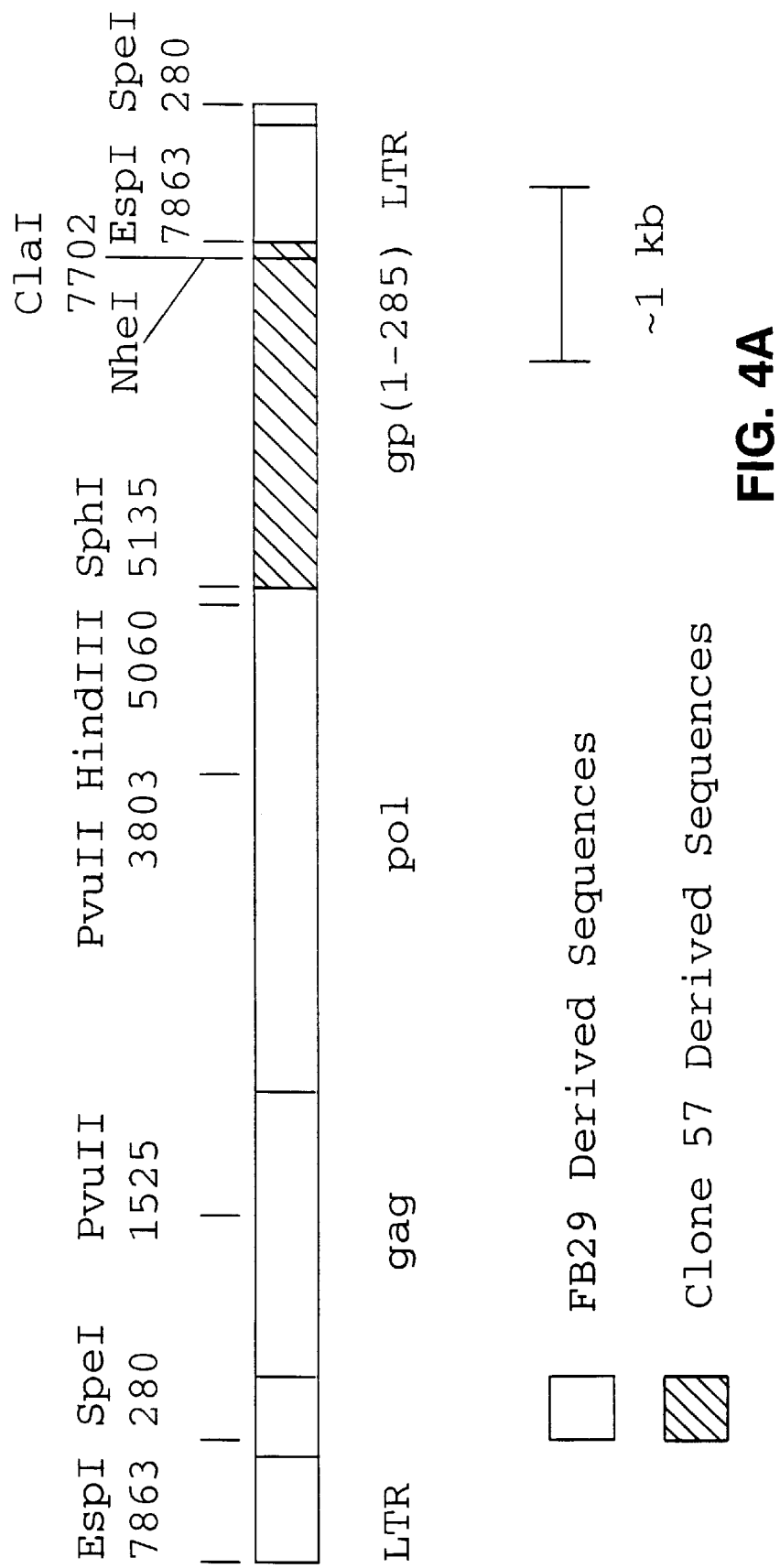

Glycopeptide expression fusion vectors were derived from pLRB303 as follows. Clone 57 sequences containing the SphI site near the 5' end and modified at the 3' end were generated by polymerase chain reaction (PCR). In these modified sequences, the selected fusion sites in the hypervariable region of gp70 are followed by an in-frame NheI site that adds an ala-ser dipeptide to the end of the gp70 fragment, two stop codons (UAA-UGA), and a ClaI site. The 5' primer was 5'-CCAAGAAGCTTCTAGAAGAAA-3' (SEQ ID NO:3), the 3' primer for the gp(1-263) construct was 5'-GGTTATCGATTCATTAGCTAGCGGGGGGA GACTTGGCAGGTT-3' (SEQ ID NO:2) and the 3' primer for the gp(1-285) construct was 5'-CTCAGCCC CCGCCAGCAGGAGCTAGCTAATGAATCGATAACC-3' (SEQ ID NO:1). PCR was carried out using Vent® polymerase (New England Biolabs) in supplied Vent® buffer plus 4 mM MgSO$_4$ and the recommended BSA with 0.5 microM primers, 400 microM each dNTP, 100 ng of pLRB140 (a HindIII (5063) to KpnI (8323) fragment of clone 57 in plasmid pTZ18R (US BIOCHEMICALS) containing the 3' end of the pol gene, all of the env gene, and most of the 3' LTR) in a Perkin Elmer Cetus DNA Thermal Cycler 9810 for 25 cycles of 960 for 1.5 min, 52° for 1.5 min, 72° for 1.5 min. Polymerase was added last to reaction mixtures that were pre-incubated and held at 96°. Following extraction with phenol:chloroform and ethanol precipitation, PCR products were digested with SphI and ClaI and the desired SphI/ClaI fragments purified from agarose gels with Qiaex® Resin (Qiagen) according to the manufacturer's directions. These fragments were then inserted into pLRB303 that had been digested with SphI and ClaI and gel purified. This resulted in the deletion of viral envelope sequences between the desired fusion point and the ClaI (7702) site present near the 3' end of the envelope gene. The gp(1-263) fusion vector was designated pLRB333; the gp(1-285) fusion vector was designated pLRB332. FIG. 3A shows the complete DNA sequence of pLRB332 (SEQ ID NO:1), and FIG. 3B shows the amino acid sequence (SEQ ID NO:10–11) of the encoded truncation fragment. FIG. 4A is a restriction map of the MuLV sequences of pLRB332. The NheI and ClaI sites are used for the insertion of sequences coding for the glycopeptide that is to be expressed. The structures of these plasmids were confirmed using NdeI, BamHI, SphI/NheI, SphI/ClaI, and NheI/ClaI restriction digests.

pLRB332 (SEQ ID NO:9) was deposited at the ATCC, Parklawn Drive, Rockville, Md. on Aug. 25, 1992 and assigned accession no. 69057. pLRB332 can be converted to the sequence of pLRB333 (i.e., encoding gp(1-263)) by taking a PCR-generated SphI/ClaI fragment made from pLRB332 (SEQ ID NO:9) using the primers described for construction of pLRB333 and substituting this fragment for the SphI/ClaI fragment carried by pLRB332 (SEQ ID NO:9).

CONSTRUCTION OF GENES EXPRESSING TRUNCATION FUSION GLYCOPROTEINS

For insertion of gene fragments into pLRB332 (SEQ ID NO:9) or pLRB333, PCR is used to generate DNA fragments containing an in-frame restriction site for NheI (results in an ala-ser linker between the gp70 fragment and the inserted glycopeptide) 5' to the sequence encoding the glycopeptide to be expressed and following this sequence two in-frame stop codons followed by a ClaI restriction site. If the desired gene fragment contains an NheI site, an AvrII site (results in an arg-arg linker) or SpeI site (results in an thr-ser linker) or XbaI site (results in an ser-arg linker), each of which result in NheI compatible ends, can be used instead; if the desired gene fragment contains a ClaI site, a BstBI or AccI site could be substituted. These restriction sites are used to insert the gene fragment into the expression vector, generating a gene that can express the fusion glycoprotein. A NarI or other appropriate restriction site (i.e., one not present in pLRB332 (SEQ ID NO:9) or pLRB333 or the gene fragment to be expressed and, if possible, coding for amino acids such as ala, gly, pro, ser, or thr, that are unlikely to constrain the conformation taken by the fusion glycoproteins) can be included between the gene fragment and the stop codons to allow the subsequent insertion of additional sequences at the 3' end of the fusion protein.

If all of the restriction enzymes having either NheI or ClaI compatible overhangs have at least one recognition site in the desired sequence, a new fusion vector can be generated using restriction sites for insertion that are not present in the gene fragment of interest. One can also mutate undesired restriction sites in the sequences coding for selected glycopeptides to facilitate construction. Alternatively, one can use DNA fragments from partial digests for constructions.

For construction of genes to express fusion glycoproteins containing the V1/V2 domain of HIV-1 HXB2d (amino acids 86–179 of the mature gp120) NheI and ClaI sites were used. The 5' primer was 5'-CATCGCTA GCCTAAAGCCATGTGTAAAATTA-3' (SEQ ID NO:4) and the 3' primer was 5'-ACTGATCGATTCATT AGGATACCTTTGGACAGGCC-3' (SEQ ID NO:5). The DNA substrate was 100 ng of HXB2-env (Page et al, 1990, J. Virol. 64:5270–5276) but any other source of HXB2d envelope sequences is equivalent. PCR conditions were as described above for generation of pLRB332 (SEQ ID NO:9) and pLRB333 except for using dNTPs at 200 microM. NheI/ClaI digested PCR-generated fragments were gel purified and ligated to pLRB332 (SEQ ID NO:9) and pLRB333 that had been NheI/ClaI digested and gel purified, generating pLRB335 and pLRB336, respectively. The structures of these plasmids were confirmed with NdeI, NheI/ClaI, and NsiI/NdeI restriction digests.

For construction of genes to express fusion glycoproteins containing the V3 domain of HIV-1 HXB2d (amino acids 261–306) NheI and ClaI sites were used and a NarI site was included between the HIV sequences and the stop codon, adding gly-ala to the C-terminus of the fusion protein. The 5' primer was 5'-CGGTGCTAGCTCTGTAGAAATTAA TTGT-3' (SEQ ID NO:6) and the 3' primer was 5'-CTAGATCGATCTATTAGGCGCCTGCTCTACTAAT GTTACA-3' (SEQ ID NO:7). Other components and conditions were as described above for the V1/V2 constructions except that MgSO$_4$ was not added. Insertion of PCR-generated fragments into expression vectors was as described for V1/V2 constructions. The gp(1-263)-V3 construct was designated pLRB350 (this construct has also been referred to as pLRB346). The gp(1-285)-V3 construct was designated pLRB349. Plasmid structures were characterized with NdeI, AseI, and NheI/XbaI restriction digests. The ClaI sites were not characterized because in these constructs there is C residue 3' to the ClaI site, resulting in Dam methylation that blocks cleavage by ClaI.

The produced truncation fusion glycoprotein is diagrammed in FIG. 4B.

CONSTRUCTION OF GENES EXPRESSING INSERTION FUSION GLYCOPROTEINS

Two sites within the inter-domain spacer sequence of gp70 were used above as fusion points for soluble chimeric proteins (i.e., insertion sites for heterologous protein fragments). pLRB349 and pLRB350 contain genes for truncation chimeric glycoproteins with insertions of the HXB2 V3 loop sequence following residues 285 and 263 respectively. The insertions were made to include a NarI site adjacent to and in frame with the C-terminal sequence of the truncation fusion proteins. This unique NarI site was then used to replace the missing env gene sequences between the truncation point and the ClaI site near the 3' end of the env gene. The necessary env gene sequences beginning with a NarI site were generated by PCR from pLRB303. The 5' primer for the fragment beginning with residue 263 was 5'-TCCT GGC GCC TCT AAT TCG ACT CCC ACA TT-3' (SEQ ID NO:12) ; the 5' primer for the fragment beginning with residue 286 was 5'-TTGC GGC GCC ACG GGA GAC AGG TTA CTA AAT C-3' (SEQ ID NO:13) ; the 3' primer for both fragments was 5'-ACTG TCT AGA AAG CGC GCG AAC AGA AGC GAG AAG C-3' (SEQ ID NO:17). Genes for truncation chimeric fusion glycoproteins containing a selected glycopeptide other than V3 can be converted to insertion chimeras (containing the complete env protein) by the same process used to generate the V3 insertion chimeras provided they contain a NarI or other suitable site at the 3' end of the inserted gene fragment. Alternatively, other heterologous sequences can be incorporated into the V3 insertion chimeras directly by removal of the V3 gene fragment using the NheI and NarI sites and replacing it with the appropriate NheI-NarI bounded gene fragment generated by PCR or otherwise. Using these methods with NheI and NarI sites, the complete insert consists of Ala-Ser-Heterologous Sequence-Gly-Ala (SEQ ID NO:21).

To generate an insertion chimeric glycoprotein virus plasmid one can also begin with pLRB332 (SEQ ID NO:9). If a 263/264 insertion is desired, pLRB332 is first modified as described above for the generation of pLRB333. Next, a truncation chimeric glycoprotein plasmid is constructed that incorporates a NarI site at the 3' end of the inserted gene fragment, as described above for the construction of the V3 truncation chimeric glycoprotein genes in pLRB349 and pLRB350. Finally, the truncation chimeric glycoprotein gene is converted to an insertion chimeric glycoprotein gene as described in the preceding paragraph. Using this method, any source of the clone 57 env gene that includes the 3' LTR, in which the designated 3' primer is located, can serve as substrate. A shorter clone that includes the necessary sequences of the env gene, e.g. without unnecessary LTR sequences, can also be used as a source of the C-terminal env sequences by using a different 3' primer.

EXPRESSION OF TRUNCATION FUSION GLYCOPROTEIN VECTORS

Standard cell culture and retrovirological methods were used (see, e.g. Kayman et al, 1991, J. Virol. 65:5323 and references cited therein for general methods and co-culture methods for expression of defective viral genomes).

Column-purified, or boiling mini-prep, glycopeptide fusion vector plasmid DNA (Qiagen or Nest Group kits) is transfected into the amphotropic packaging cell line PA317 (Miller and Buttimore, 1986, Mol. Cell. Biol. 6:2895) by conventional calcium phosphate methods using CellPhect reagents (Pharmacia) (or by Lipofectamine (BRL) transfection according to manufacturer's specifications) and then cells of the ecotropic packaging line psi2 (Mann et al, 1983, Cell 33:153) were added. Amphotropic pseudotypes of the glycopeptide fusion vector from PA317 cells infect psi2 cells and ecotropic pseudotypes from psi2 cells infect PA317 cells, allowing the fusion vector to spread through the culture, resulting in high level expression of the fusion protein in the culture, as well as production of high titers of pseudotyped fusion vector virus particles, usually within three-four days of establishing the co-culture. These co-cultures of PA317 and psi2 cells expressing the fusion glycoprotein can be used directly to characterize the biochemical and immunoreactive properties of the fusion protein. To eliminate the presence of helper virus envelope proteins, the pseudotyped vector virus from these cultures was used to infect NIH 3T3 cells and clonal infected cell lines generated by limiting dilution.

The produced insertion fusion glycoprotein is diagrammed in FIG. 4B.

EXPRESSION OF INSERTION FUSION GLYCOPROTEIN VECTORS

Functional insertion chimeric glycoproteins are expressed by transfection into 3T3 cells. For preparing pseudotypes of infectious chimeras, virus from these cells can be infected into appropriate packaging cell lines. For example, a virus coding for an ecotropic MuLV can be used to infect an amphotropic packaging cell line, such as the PA317 line. This produces pseudotyped virus that will infect, e.g. humans, but will not cause a spreading viremia, except in mice and rats. For non-functional insertion chimeric glycoproteins or for functional insertion chimeric glycoproteins expressed from retroviral vectors without either a functional gag or pol genes, expression is carried out in packaging cocultures as described for truncation chimeric glycoproteins.

GENERAL METHODS FOR ANALYSIS

Characterization of the fusion proteins was done by radioimmunoprecipitation assay (RIPA) and sodium dodecyl sulfate polyacrylamide gel electrophoresis (SDS-PAGE), methods for which are referenced in Kayman et al, 1991, J. Virol. 65:5323, and by ELISA as described herein.

V1/V2 domain synthetic peptides ADP 740.9 through ADP 740.17, which are each 20 amino acids long and offset by 10 amino acids and match HXB2 gp120 sequences from amino acids 82 through 181, were obtained. Additional V2 domain 16 mer oligopeptides matching amino acids 135–149 of the HXB2d sequence (ADP 794.2) and the homologous sequences from MN (ADP 794.3) and RF (794.4), each containing an additional C-terminal cys residue, were also obtained. The analogous peptide matching the consensus sequence for this region as defined in the Los Alamos Human Retroviruses and AIDS database, Ile- Arg-Asp-Lys-Val-Gln-Lys-Glu-Tyr-Ala-Leu-Phe-Tyr-Lys-Leu-(Cys) (ADP 794.1), (SEQ ID NO:22) was also used. A linear V3 peptide corresponding to the complete sequence between the Cys residues defining the V3 loop of HXB2, Thr-Arg-Pro-Asn-Asn-Asn-Asn-Thr-Arg-Lys-Ser-Ile-Arg-Ile-Gln-Arg--Gly-Pro-Gly-Arg-Ala-Phe-Val-Thr-Ile-Gly-Lys-Ile-Gly-Asn-Met-Arg-Gln-Ala-His, (SEQ ID NO:23) was obtained. Peptide ADP 792.3 had the same sequence for the V3 loop and included the defining Cys residues and a C-terminal Asn. It was obtained as the "cyclic" form. An MN V3 peptide, ADP 715, Arg-Lys-Arg-Ile-His-Ile-Gly-Pro-Gly-Arg-Ala-Phe-Tyr-Thr-Thr-Lys-Asn (SEQ ID NO:24), corresponded to the tip of the V3 loop.

To facilitate purification of the gp(1-263):V3$_{HXB2}$ fusion glycoprotein, His$^8$Gln$^9$ of gp70 were replaced with a sequence of six His residues. PCR overlap mutagenesis (Ho et al., 1989, Gene 77:51–599) was used to construct the appropriate SphI to NheI gene fragment for insertion into the expression vector. Supernatants from 3T3 cells expressing the His$_6$ form of gp(1-263):V3$_{HXB2}$ were dialyzed against PBS (pH 8), NaCl was added to 0.5M, and protein was bound to Ni$^{2+}$-nitrilotriacetate Sepharose (Qiagen) in this buffer. gp(1-263):V3$_{HXB2}$ was eluted with 30 mM imidazole in PBS (pH 7.4) following a 20 mM imidazole wash, and constituted only a small fraction of the Coomassie-staining material in these preparations. Comparison with bovine serum albumin standards yielded an estimate of 3 μg of partially purified gp(1-263) :V3$_{HXB2}$ isolated per ml of culture supernatant.

ELISAs were performed in TiterTek Immuno-assay plates (Flow Laboratories). Antigens were adsorbed to wells for 60 min in 100 μl carbonate buffer (pH9.6) washed with PBS/0.05% Tween, blocked for 90 min with 2% BSA in PBS, and washed again with PBS/0.05% Tween. 100 μl of serum diluted in PBS was added for 60 min at RT, and wells were washed with PBS/0.05% Tween, incubated for 60 min with 100 μl alkaline phosphatase coupled goat anti-human IgG (Zymed) diluted in 2% BSA, washed in PBS/0.05% Tween, and 100 μl of 1 mg/ml p-nitrophenol phosphate in diethanolamine buffer (pH 9.8) was added. Absorbance at 405 nm was measured between 30 and 60 min after substrate addition. The amount of partially purified gp(1-263):V3$_{HXB2}$ used per assay was always sufficient to give at least 75% of the maximum achievable signal. Peptides were used at 100 ng per well; assays were insensitive to increased amounts of peptide. Background A$_{405}$ reaction in wells lacking antigen was subtracted from the data obtained.

ANALYSIS OF FUSION PRODUCTS a. Analysis of synthesis and secretion of the gp(1-263) and gp(1-285) truncated products 3T3 cells expressing either gp(1-263) (top) or gp(1-285 ) (bottom) were pulse labeled with 35 $^{35}$S-cysteine for 30 minutes (lanes p) and chased with unlabeled medium for 1, 2, 4 or 6 hrs. Cell lysates and supernatants were then immunoprecipitated with a polyclonal goat anti-gp70 serum (goat anti-Rauscher gp70 , Microbiological Associates), and analyzed by SDS-PAGE. Results are shown in FIG. 5.
Results This experiment documents the efficient synthesis and secretion of both the gp(1-263) and gp(1-285) truncated gp70 products. For the gp(1-263) construct, at the end of the 30 minute pulse a single band of about 38 kD was seen in the cell extract. After the 1 hr chase, greater than 90% of this material was found in the supernatant medium with less than 10% left in the cells. After 2 hrs of chase, a similar level of protein was detected in the medium, while at longer periods the amount recovered starts decreasing, presumably indicating degradation.

Similar results were found for the gp(1-285) construct. In this case two bands were seen in the cell extracts, a major 43 kD band representing the precursor form, and a 48 kD band representing O-glycosylated product. After a 1 hr chase period, almost all of the labeled material had been secreted into the extracellular medium in the form of a major 48 kD band and a minor 50 kD band. The small amount of material left in the cells seems stable, and presumably represents a fraction of misfolded protein which cannot be fully processed and secreted.

b. Analysis of immunoreactivity of gp(1-263)-V1/V2 fusion product.

Figure 6A:
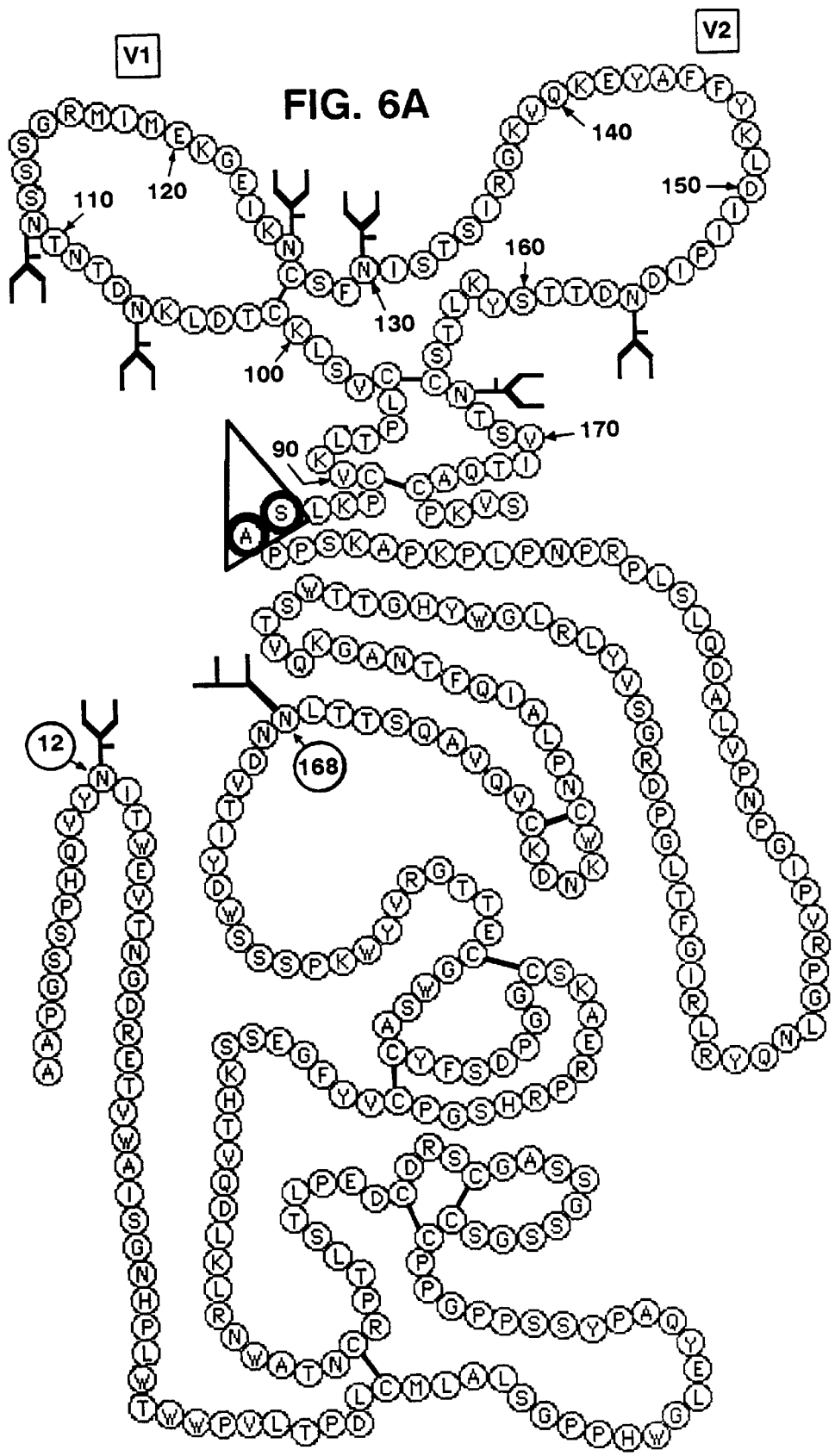

FIG. 6A shows the structure of the fusion protein, showing disulfide bonds and glycosylation sites of both the gp70-derived region and the gp120-derived region. The two regions are separated by an ala-ser dipeptide linker marked by a triangle. The two N-linked glycosylation sites in the gp70 region are residues 12 and 168 and are indicated by circled numbers. The glycosylation sites in the V1/V2 domains are indicated by the branched structures.

FIG. 6B shown an analysis of the immunoreactivity of the secreted gp(1-263)-V1/V2 fusion protein. Packaging cell cultures expressing the gp(1-263)-V1/V2 product were labeled with 100 uCi of 35$^{35}$S-cysteine overnight. Cell supernatants were immunoprecipitated with MAbs CRA-3 (lane 1), C810G (lane 2), G3–4 (lane 3), sera from chimp 087 (lane 4), anti-gp70 MAb 273 (lane 5), and goat anti-gp70 serum (lane 6). Preimmune chimp and goat sera were negative, as were a number of other monoclonals against different sites on gp120. The polyclonal anti-gp70 serum also precipitates a MuLV gp70 band that is derived from the helper virus in the packaging cell line.

Results

The structure of the gp(1-263)-V1/V2 fusion product is indicated in FIG. 6A. FIG. 6B shows that the expressed protein is recognized by anti V1/V2 MAbs that are dependent on glycosylation (CRA3, C108G and G3–4) and conformation (G3–4 and CRA3). This shows that proteins are expressed that are correctly folded and glycosylated.

c. Analysis of sera from HIV-1-seropositive hemophiliacs for antibodies reactive with the HXB2 V1/V2 fusion protein gp(1-263)-V1/V2.

Figure 7:
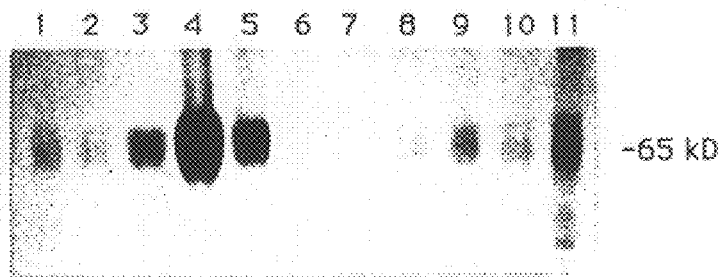

3T3 cultures expressing the gp(1-263)-V1/V2 fusion product were radiolabeled with 100 uCi of $^{35}$S-cysteine overnight, and supernatant medium was immunoprecipitated with a group of sera of HIV-1-infected hemophiliacs (lanes 1–11). Radioimmunoprecipitations were performed as described for FIG. 6. All sera were tested at a dilution of 1:50. Results are shown in FIG. 7.

Results

A reasonable percentage of HIV seropositive human sera contains low titers of antibodies that recognize the gp(1-263)-V1/V2 protein (lanes 1,3,5,9,11), and one patient serum (lane 4) possessed particularly potent precipitating activity against this construct. This suggests that most humans are capable of producing antibodies against the V1/V2 region. This result further suggests that the HXB2 V1/V2 sequence is either a fairly common component in the panoply of viruses seen by these patients, or it contains epitopes that are crossreactive with those seen in the V1/V2 domains of the viruses infecting these patients.

d. Quantitative immunoprecipitation of gp(1-263)-V1/V2 by goat anti-Rauscher gp70 serum.

Figure 8:
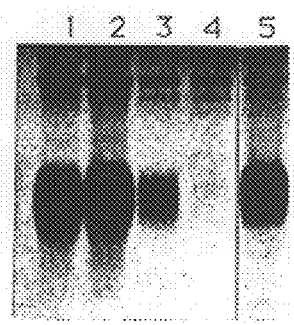

Supernatant medium containing radiolabeled gp(1-263)-V1/V2 protein was immunoprecipitated sequentially 3 times with a 1:40 dilution of goat anti-gp70 serum (lanes 1–3) and then with a 1:100 dilution of serum from a chimp with a high titer of anti-V/V2 antibody (lane 4). Results are shown in FIG. 8. Immunoprecipitation by the chimp serum without preclearing with the goat anti-gp70 serum is shown in lane 5.

Results

Figure 9:
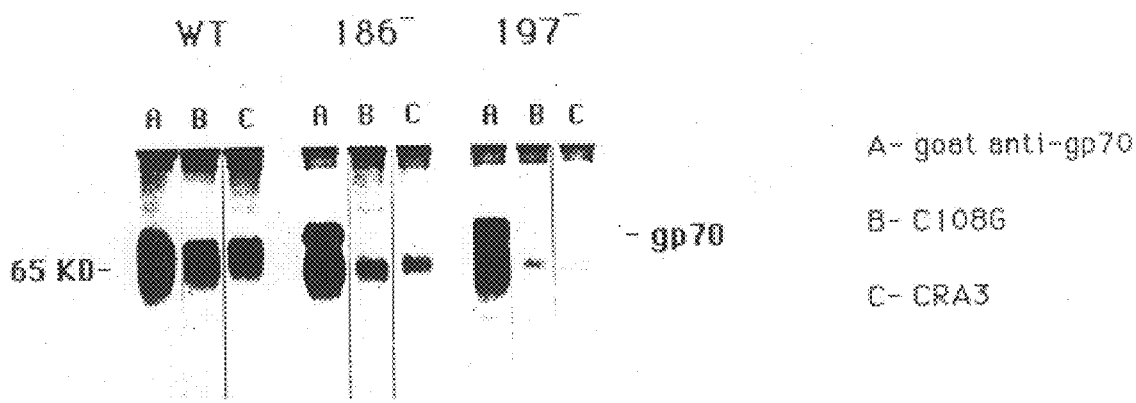

The complete removal of chimp serum immunoprecipitable material by the goat anti-gp70 serum (lane 4) shows that the goat anti-gp70 serum can quantitatively immunoprecipitate all of the gp(1-263)-V1/V2, including the fraction recognized by the chimp anti-V1/V2 antibodies. Goat serum can therefore be used to purify the fusion proteins by immunoaffinity methods.

e. Analysis of immunoreactivity of glycosylation site mutants of gp(1-263)-V1/V2 (FIG. 9).

Medium containing radiolabeled fusion proteins from cells expressing wild type gp(1-263)-V1/V2 (WT) and gp(1-263)-V1/V2 in which either the asn at position 186 (186⁻) or the one at 197 (197⁻) mutated to gln was immunoprecipitated with either goat anti-gp70 serum (lane A), MAb C108G (lane B), or MAb CRA3 (lane C). The wild type protein runs at a position corresponding to a molecular weight of 65 kD, while the mutant proteins are about 2 kD smaller. The two mutant proteins were grown in the packaging cell cultures, which contain a gp70 band contributed by the packaging virus, that is recognized by the goat anti-gp70 serum.

Results

The wild type gp(1-263)-V1/V2 and the two glycosylation mutants are recognized equally well by the goat anti-gp70 serum, but the mutants are recognized only poorly, if at all, by the two monoclonal antibodies. The 197 mutant was not recognized by CRA3 at all, while both mutants react only weakly with C108G. These results document the fact that both the 186 and 197 sites are glycosylated in the wild type fusion protein, and that both the CRA3 and C108G epitopes are dependent on N-linked glycans at these two positions for proper expression.

f. Structure, expression and immunogenicity of the gp(1-263)-V3 fusion protein (FIG. 10).

Figure 10A:
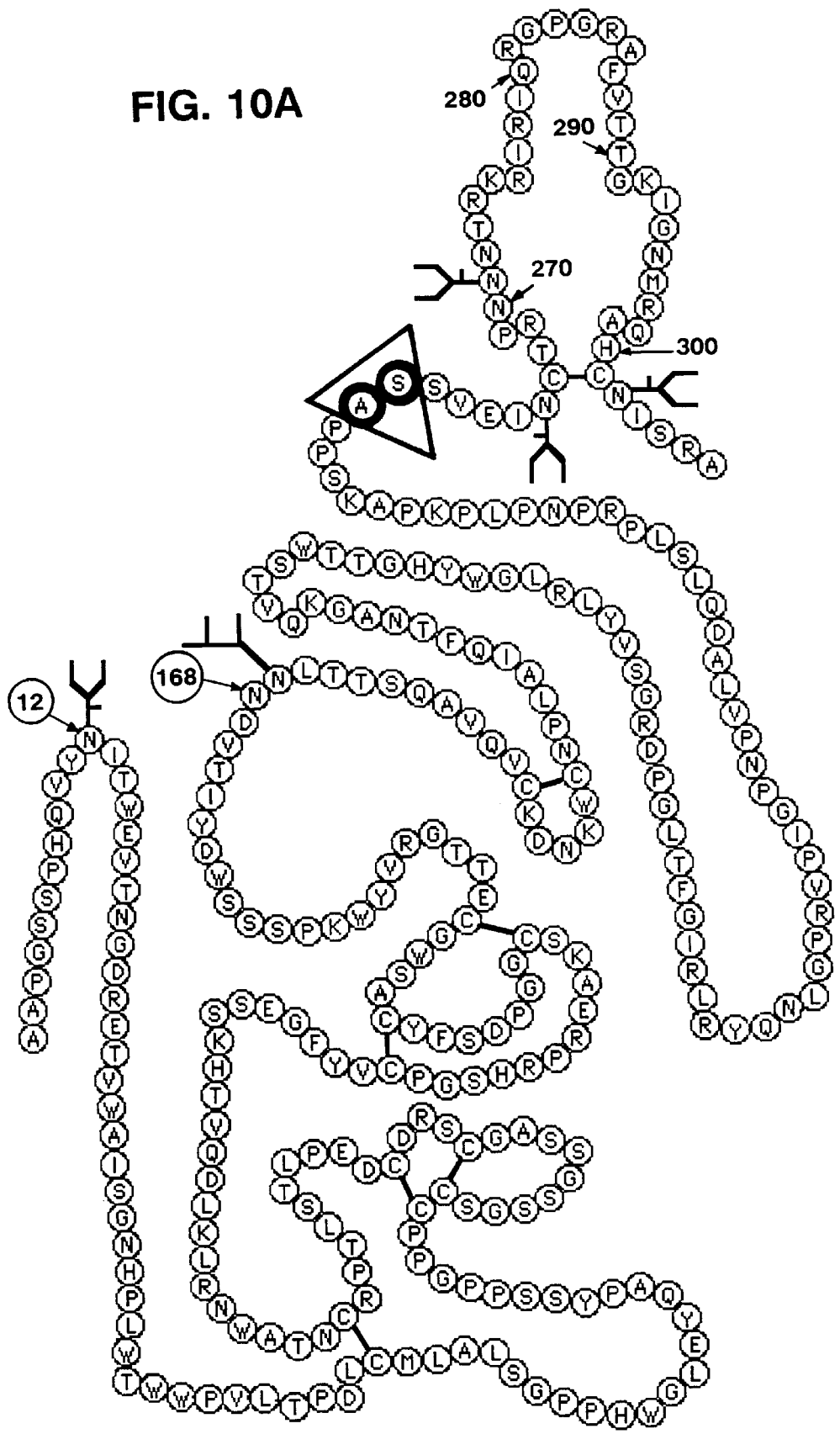

In FIG. 10A the sequence of the gp(1-263)-V3 fusion protein is shown, showing the gp70 domain, the ala-ser linker dipeptide (in triangle) and the fragment of HXB2 gp120 containing amino acids 261–306. This region includes the $Cys_{266}$–$Cys_{301}$ disulfide bond, the conserved N-linked glycosylation site inside the V3 loop at position 271, and the two conserved N-linked glycosylation sites immediately outside the V3 loop at positions 265 and 302. FIG. 10B shows an analysis of the structure and immunoreactivity of the expressed fusion product. Cells expressing the V3 fusion protein were labeled with $^{35}$S-cysteine and supernatant medium immunoprecipitated with sera obtained at different dates from an HIV$^{III}$-infected chimp (lanes 1–7) or with goat anti-gp70 serum (lane 8). A fusion product of ⁻52 kD was recognized by the chimp and goat sera but not by sera from normal chimp or goat sera (not shown).

Results

These experiments demonstrate the efficient synthesis and secretion of the gp(1-263)-V3 fusion construct in immunologically active form. The size of the expressed product suggests that the three glycosylation sites included in the V3 sequences are all utilized.

g. V3 chimeras pLRB386 carries the HXB2 V3 domain at the 263/264 site on the 46 amino acid insert that contains 3 N-linked glycans and forms an 36 amino acid disulfide-linked loop. The recombinant env for the insertion chimera was produced in an otherwise wild type MuLV genome. When pLRB386 was transfected into 3T3 cells a spreading viral infection resulted. The growth rate of the recombinant virus was similar to that of wild type virus. By immunofluorescence, the recombinant gp70 in the intact virion was shown to present HIV-I epitopes seen by human and chimpanzee type-specific sera and by a potent neutralizing monoclonal antibody, 41.1, that is specific for an epitope in V3 not presented by synthetic peptides. Anti-V3 sera and MAbs were found to also immunoprecipitate intact virions containing the hybrid protein, indicating that these epitopes are highly exposed on the surface of intact virions. Thus, the V3 chimeric virus retains normal infectivity, and expresses a conformational epitope in V3 (the epitope for MAb 41.1) that is a potent target for neutralizing antibodies.

The amount of mature V3 chimeric gp70 produced was similar to the amount of wild type gp70 produced. A large excess of secreted N-terminal protein fragments was cleaved at a site believed to be within the V3 loop from the precursor chimeric gPr80 present in the endoplasmic reticulum. The C-terminal fragment of the cleaved precursor was degraded intracellularly. A percentage of wild type gPr80 was also degraded intracellularly without secretion of detectable fragments.

This V3 insertion chimeric virus appeared to be infectious and immunogenic in rats. Following subcutaneous injection into rats, ELISA titers vs. gp160 were detectable within 4 weeks and rose continuously for at least 18 weeks. Such an extended response to a single exposure strongly suggests that viremia was established in these animals.

A series of V3 insertion chimeras was produced and partially characterized. These included insertion glycoproteins in which the HXB2 V3 peptide was inserted at the 263/264 (pLRB386) and 285/286 sites (pLRB396), between aa 263 and 286 (pLRB395) (i.e., deleting residues 264 through 285, really 265 through 285 since aa 264 is fortuitously restored by the NheI site), and between aa 285 and 264 (pLRB392) (i.e., between repeated sequences of aa 264–285). Also, a mutant sequence in which the Cys residues defining the V3 loop were changed to Ser residues was inserted at the 263/264 site (pLRB393). These constructs had close to normal or normal growth characteristics in tissue culture and expressed the native epitope for MAb 41.1. An infectious insertion chimera carrying the MN-like V3 domain from the Jr-CSF isolate inserted at 263/264 (pLRB410) of HIV-1 was also produced. All of the V3 insertion chimeras generate high levels of a proteolytic fragment cleaved within the V3 loop, as described above.

h. V1/V2 chimeras

The HXB2 V1/V2 domain is contained within the 94 amino acid fragment (amino acids 86–179 of mature gp120 ) that includes three disulfide bonds. Two of these disulfide bonds generate the V1 and V2 variable loops separated by a short stretch of conserved sequence and the third disulfide bond generates an arm of conserved flanking sequences. The expressed sequence includes six signals for N-linked glycosylation, all of which have been reported to be utilized and one of which (attached to $Asn^{156}$) was found to be necessary for viral growth in cell culture. The 5' primer for producing the V1/V2 fragment was the same as used to produce the fragment for the truncation chimeric glycoprotein. The 3' primer was 5'-ACTG ATC GAT TCA TTA GGC GCC GGA TAC CTT TGG ACA GGC C-3' (SEQ ID NO:14), which incorporated the NarI site needed for the insertion chimeric glycoprotein that was absent from the 3' primer used to generate the V1/V2 fragment for the truncation chimeric glycoprotein. This gp120 fragment was inserted into the 263/264 site by replacement of the NheI/

NarI V3 gene fragment of pLRB386 to produce pLRB401. This vector expresses a viable MuLV with a gp70 of appropriate size that is recognized by type specific chimpanzee sera, by rat anti-V2 MAb 10/76b, and by a human serum that has cross-reactive anti-V1/V2 antibodies.

i. V4/C4 chimeras

The V4/C4 domain of HXB2d is contained within an 80 amino acid fragment (residues 342–421) that includes two disulfide bonds, one of which generates the V4 loop, and both of which are involved in forming the majority of the C4 region into a loop. 21 amino acids of the C3 region are included in this construct, and the last 12 amino acids of the C4 region are not. The sequence includes 5 signals for N-linked glycosylation, all of which have been reported to be utilized and none of which was found to be necessary for viral growth in cell culture. The 5' primer for producing the V4/C4 fragment was 5'-CATC GCT AGC GTA ACG CAC AGT TTT AAT TGT GGA-3' (SEQ ID NO:15). The 3' primer was 5'-ACTG ATC GAT CTA TTA GGC GCC CCC TGT AAT ATT TGA ACA T-3' (SEQ ID NO:16). The vector expressing this insertion chimera, pLRB408, was constructed in the same manner as pLRB401. It expresses infectious MuLV with a gp70 of appropriate size that is recognized by rat anti-C4 MAb 38.1

The interdomain linker region of gp70 thus appears to be remarkably tolerant of both insertions and rearrangements.

USE OF CHIMERIC GLYCOPROTEINS TO ANALYZE IMMUNE SERA

A fusion glycoprotein containing the V3 domain of the IIIB strain of HIV-1, gp(1-263):V3$_{HXB2}$, was recognized by sera from a human and a chimpanzee that had been infected by HIV$_{IIIB}$ but not by sera from hemophiliac patients that had been infected with HIV-1 viruses of MN-like V3 serotype. The reactive sera had approximately five-fold higher ELISA titers when assayed on gp(1-263):V3$_{HXB2}$ than on matching V3 peptides. Immunoprecipitation of this fusion glycoprotein by the human serum was only partially blocked by V3 peptide, demonstrating that this infected individual produced antibodies against epitopes in V3 that were expressed on the fusion glycoprotein but not by synthetic peptides. A fusion protein containing the HXB2 V1/V2 domain was recognized by the HIV$_{IIIB}$-infected patient serum as well as by 17 out of 36 HIV-1 seropositive hemophiliac, gay male and intravenous drug user patient sera. Many of these HIV$^+$human sera reacted with V1/V2 domains from several HIV-1 clones expressed in fusion glycoproteins, (Jr-CSF, pLRB357; NL4-3, pLRB359; SF2, pLRB360; MN-ST, pLRB361; Jr-FL, pLRB362). These results indicate the presence of cross-reactive antibodies against epitopes in the V1/V2 domain. Recognition of gp(1-263):V1/V2$_{HXB2}$ by the HIV$_{IIIB}$-infected human patient serum was largely blocked by synthetic peptides matching V1 but not V2 sequences, while recognition of this construct by a broadly cross-reactive hemophiliac patient serum was not blocked by individual V1 or V2 peptides or by mixtures of these peptides. These data demonstrated that the chimeric glycoproteins described here effectively present native epitopes present in the V1/V2 and V3 domains of gp120 and provide efficient methods for detection of antibodies directed against native epitopes in these regions.

EXPRESSION OF FUSION GLYCOPROTEINS USING VACCINIA

One can express a fusion glycoprotein of this invention from a vaccinia virus vector. One such vector is the recently developed NYVAC vector, a highly attenuated strain of vaccinia virus that is able to elicit immune responses to foreign proteins inserted into the viral genome (Tartaglia et al., 1992, Virology 188:217–232). Although unable to replicate on human derived cells, NYVAC does infect various human cells and allows for the expression of foreign proteins in human cells. Virus can be grown, amplified, and manipulated in Vero cells (ATCC No. CCL81) or primary chick embryo fibroblasts. To insert a foreign gene into a vaccinia virus, an intermediate plasmid vector is constructed in which the selected gene is appropriately linked to the thymidine kinase gene (tk) promoter. Plasmids carrying a fragment of the vaccinia genome surrounding the tk gene in which tk gene sequences need to be replaced with a multiple cloning site, such as pSD460 (Tartaglia et al., 1992, Virology 188:217–232), are used for this purpose. Standard recombinant DNA techniques are used to insert the selected fusion glycoprotein gene into such a vector. If an insertion chimeric glycoprotein is to be expressed along with a gag gene to provide for defective particle formation, it is also incorporated into pSD460 or its equivalent between the flanking vaccinia sequences. It also needs to be associated with a promoter, which can be a second copy of the vaccinia tk promoter. Alternatively it can be associated with a heterologous promoter such as the enhancer/promoter sequences from the widely used immediate early gene of human cytomegalovirus. Following construction of the plasmid vector containing the selected gene or genes associated with promoters (and situated between flanking vaccinia sequences from the tk region of the virus genome), in vivo recombination is used to introduce the selected genes into the complete virus genome. This is accomplished by co-transfecting the plasmid vector DNA and NYVAC genomic DNA into a cell line, such as Vero, to allow recombinants to form. Recombinant virus is identified by plaque hybridization with radiolabelled DNA probes for the inserted genes. The recombinant virus is used for inoculation of mammals or infection of cells in culture for production of fusion glycoproteins.

PLASMID VECTORS FOR EXPRESSION OF FUSION GLYCOPROTEINS

One can express a fusion glycoprotein of the invention from a non-replicating vector such as pRc/CMV (Invitrogen, San Diego Calif.). Standard molecular biological techniques are used to insert the gene for the selected env fusion glycoprotein into the multiple cloning site adjacent to the enhancer/promoter sequences from the immediate early gene of the human cytomegalovirus. If it is desired to express a gag gene to allow particle formation, the gag gene could be substituted for the neomycin gene in this vector that is expressed from a Rous sarcoma virus LTR. Following insertion of the selected gene or genes into the plasmid vector, the plasmid DNA is transfected into appropriate mammalian cells, such as mouse 3T3 or Vero monkey, for expression of fusion glycoprotein in culture. If the neomycin gene of the vector has not been removed, transfectant lines are selected for G418 resistance and screened for appropriate production of the fusion glycoprotein. If the neomycin gene has been removed, the plasmid vector for expression of the fusion glycoprotein is co-transfected with ⅕ as much of another vector that carries a drug-selectable marker to allow selection of transfectant cell lines. To use a plasmid vector for expression of fusion glycoproteins in mammals, direct DNA immunization is used. Purified plasmid DNA is inoculated into the mammal by any of a number of methods, for example, by intramuscular injection of non-replicating expression vector DNA. This method has been shown to be effective for immunizing mice with influenza A nucleoprotein (Ulmer et al 1993 Science 259:1745–1749).

PARTICLE BASED PURIFICATION

This invention can be used as a method for the production and purification of specific glycopeptides. The amount of insertion chimeric glycoprotein produced is generally less than the amount of the corresponding truncation chimeric glycoprotein. This is due to the relatively inefficient processing of the precursor protein encoded by complete env genes with or without insertions. The lower amount produced, however, may be balanced by the fact that the insertion chimeric glycoproteins will, in general, be associated with virus particles rather than as soluble proteins like the truncation chimeric glycoproteins. The virus particles and associated insertion chimeric glycoproteins are separated from soluble proteins by, e.g., size exclusion chromatography (Pinter, Honnen and Tilley 1993 J. Virol. In Press) or filtration through substrates with appropriate pore sizes, as well as by sedimentation velocity or sedimentation density methods, methods that are used on preparative scales. Following separation from soluble components, the insertion chimeric glycoproteins are released from the particle by conventional methods such as: reduction of disulfide bonds; treatment with detergents such as octylglucoside, NP40, or Triton X-100; treatment with chaotropic agents such as guanidine hydrochloride, urea, or lithium chloride. Treatments that have a negative impact on the properties of the glycopeptide being produced are avoided. Following release of the insertion chimeric glycoproteins, the glycoproteins are purified away from the other viral proteins. If the viral membrane has not been disrupted, the methods used to separate the particles from soluble proteins can be used to separate the fusion glycoproteins from the other particle associated proteins. If the viral membrane has been solubilized but the viral core remains intact, the insertion chimeric glycoproteins can be separated from the core proteins as above, and the insertion chimeric glycoproteins purified away from the transmembrane viral protein by standard protein chemistry techniques. If the entire viral particle is disrupted and its component proteins solubilized, the insertion chimeric glycoproteins can be purified from the other viral protein by standard protein chemistry techniques. This is easier than purifying a soluble protein from cell supernatants. The fraction of the mixture that is fusion glycoprotein is greater and there are fewer contaminating proteins.

Following purification of the insertion chimeric glycoproteins, the selected glycopeptide can be cleaved from the carrier SU protein domains. To do so, cleavage sites for sequence specific proteases are incorporated into the insertion chimeric glycoproteins both immediately N-terminal and immediately C-terminal to the glycopeptide. Different cleavage targets can be used on either side of the glycopeptide. One site can be the blood coagulation factor Xa cleavage site (see above), and the other can be the Leu-val-pro-arg-gly-ser (SEQ ID NO:25) cleavage site of thrombin. The selected glycopeptide is then purified from the fragments of SU (and the proteases, unless immobilized proteases are used) by standard protein chemistry techniques.

We claim:

1. A fusion glycoprotein expressed by a vector, said fusion glycoprotein comprising (a) an amino acid sequence that has biological activity and is from a protein that lacks a hydrophobic glycosylation signal located about seven residues N-terminal to a Cys-Trp-Leu-Cys sequence (SEQ ID NO:18), said amino acid sequence being operably linked to the C-terminus of (b) a polypeptide sequence from a retroviral env surface protein, which polypeptide sequence comprises an N-terminal fragment of said retroviral env surface protein, wherein said fragment includes all the Cys residues of the N-terminal globular domain of said retroviral env surface protein, and wherein said retroviral env surface protein contains an N-glycan attachment site within a hydrophobic glycosylation signal located about seven residues N-terminal to a Cys-Trp-Leu-Cys sequence (SEQ ID NO:18).

2. The fusion protein of claim 1, wherein said polypeptide sequence comprises at least a portion of an interdomain linker region extending from the last Cys residue of said N-terminal globular domain to said N-glycan attachment site.

3. The fusion protein of claim 2, wherein said polypeptide sequence further comprises the C-terminal globular domain of said env surface protein operably linked to the C-terminus of said amino acid sequence.

4. The fusion glycoprotein of claim 3, wherein said polypeptide sequence comprises said retroviral env surface protein.

5. The fusion glycoprotein of claim 3, wherein said amino acid sequence is operably inserted within said at least a portion of the interdomain linker.

6. The fusion glycoprotein of claim 1, wherein said vector comprises a gene encoding a protein that functions as a retroviral env gene for virus infection.

7. The fusion glycoprotein of claim 1, wherein said amino acid sequence is less than 150 amino acids long.

8. The fusion glycoprotein of claim 1, wherein said amino acid sequence comprises the V2 region of gp120 of HIV-1 or a glycosylated fragment thereof.

9. The fusion glycoprotein of claim 1, wherein said amino acid sequence comprises the V1 region of gp120 of HIV-1 or a glycosylated fragment thereof.

10. The fusion glycoprotein of claim 1, wherein said amino acid sequence comprises the V3 region of gp120 of HIV-1 or a glycosylated fragment thereof.

11. The fusion glycoprotein of claim 1, wherein said amino acid sequence comprises the amino acid sequence of the V1/V2 domain of gp120 of HIV-1.

12. The fusion glycoprotein of claim 1, wherein said amino acid sequence comprises the V3 domain of gp120 of HIV-1.

13. The fusion glycoprotein of claim 1, wherein said amino acid sequence comprises the V2 domain of gp120 of HIV-1.

14. The fusion glycoprotein of claim 1, wherein said amino acid sequence is amino acid sequence 86–179 of gp120 of the HXB2d strain, or a corresponding sequence of another HIV-1 strain.

15. The fusion glycoprotein of claim 1, wherein said amino acid sequence is amino acid sequence 261–306 of gp120 of the HXB2d strain, or a corresponding sequence of another HIV-1 strain.

16. The fusion glycoprotein of claim 1, wherein said vector is a retroviral particle.

17. The fusion glycoprotein of claim 16, wherein said retroviral particle is a Murine Leukemia Virus (MuLV) particle.

18. A retroviral particle comprising a recombinant gene encoding the fusion glycoprotein of claim 1.

19. The retroviral particle of claim 18, wherein said retroviral particle is a MuLV particle.

* * * * *